United States Patent
Waller et al.

(10) Patent No.: US 11,059,835 B2
(45) Date of Patent: *Jul. 13, 2021

(54) SYNTHESIS OF CEPHALOSPORIN COMPOUNDS

(71) Applicant: Merck Sharp & Dohme Corp., Rahway, NJ (US)

(72) Inventors: David Waller, Somerville, MA (US); Gregory Gazda, Sudbury, MA (US); Zachary Minden, Watsonville, CA (US); Lisa Barton, Haverhill, MA (US); Clifton Leigh, Windham, NH (US)

(73) Assignee: Merck Sharp & Dohme Corp., Rahway, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 16/880,223

(22) Filed: May 21, 2020

(65) Prior Publication Data

US 2020/0385404 A1 Dec. 10, 2020

Related U.S. Application Data

(60) Continuation of application No. 16/181,884, filed on Nov. 6, 2018, now Pat. No. 10,662,202, which is a division of application No. 15/503,907, filed as application No. PCT/US2015/045287 on Aug. 14, 2015, now Pat. No. 10,125,149.

(60) Provisional application No. 62/111,840, filed on Feb. 4, 2015, provisional application No. 62/065,993, filed on Oct. 20, 2014, provisional application No. 62/037,676, filed on Aug. 15, 2014.

(51) Int. Cl.
*C07D 501/56* (2006.01)
*C07D 501/04* (2006.01)

(52) U.S. Cl.
CPC ......... *C07D 501/56* (2013.01); *C07D 501/04* (2013.01)

(58) Field of Classification Search
CPC .............................. C07D 501/56; C07D 501/04
USPC ......................................................... 544/47
See application file for complete search history.

(56) References Cited

U.S. PATENT DOCUMENTS

| | | | |
|---|---|---|---|
| 5,401,734 A | 3/1995 | Yamanaka et al. | |
| 7,129,232 B2 | 10/2006 | Ohki et al. | |
| 7,192,943 B2 | 3/2007 | Yamanaka et al. | |
| 10,125,149 B2 | 11/2018 | Waller et al. | |
| 10,662,202 B2 * | 5/2020 | Waller | C07D 501/56 |
| 2014/0274958 A1 | 9/2014 | Lai et al. | |

FOREIGN PATENT DOCUMENTS

| | | |
|---|---|---|
| CN | 100343260 | 10/2007 |
| WO | 2004039814 A1 | 5/2004 |
| WO | 2007119511 A1 | 10/2007 |
| WO | 2016025839 A1 | 2/2016 |

OTHER PUBLICATIONS

Ayoko Toda, et al., Synthesis and SAR of novel parenteral antipseudonmonal cephalosporins: Discovery of FR 264205, Bioorganic and Medicinal Chemistry Letters, 2008, pp. 4849-4852, vol. 18, WO.
Palmisano, Giovanni, Base-Modified pyrimidine nucleosides, Efficient entry to 6-derivatized uridines by sn-pd transmetallation-coupling process, Tetrahedron, Mar. 1, 1993, 2533-2542, 49-12, EP.
Kenji Murano, Structural Requirements for the stability of novel cephalosporins to AMPC B-lactamase based on 3D-structure, Bioorganic and Medicinal Chemistry, Nov. 22, 2007, 2261-2275, 16, WO.
Palmisano, Giovanni, et al., 2-(Tributylstannyl)-1-([2-(trimethysily)ethoxy]methy)-1H-indole . . . , Helvetica Chimica ACTA, 1993, 2356-2366, vol. 76 No. 6.
Vittorio Farina, et al., Palladium-catalyzed coupling between cephalosporin derivatives and unsaturated stannanes: A new ligand for palladium chemistry, Tetrahedron Letters, 1988, pp. 5739-5742., vol. 29, Issue 45.
PCT Search Report and Written Opinion for Patent Application PCT/US2015/045287 dated Jan. 11, 2016; 12 pages.
U.S. Appl. No. 15/503,907, filed Feb. 14, 2017.
U.S. Appl. No. 16/181,884, filed Nov. 6, 2018.

* cited by examiner

*Primary Examiner* — Kahsay Habte
(74) *Attorney, Agent, or Firm* — Patricia A. Shatynski; John C. Todaro

(57) ABSTRACT

Provided herein is a method for the synthesis of cephalosporin antibiotic compounds comprising a palladium-catalyzed coupling reaction.

28 Claims, 5 Drawing Sheets

SYNTHESIS OF CEPHALOSPORIN COMPOUNDS

1. CROSS REFERENCE TO RELATED APPLICATIONS

This application is a Division of U.S. Ser. No. 15/503,907, filed Feb. 14, 2017, now U.S. Pat. No. 10,125,149, which is a U.S. National Phase application under 35 U.S.C. § 371 of PCT Application No. PCT/US2015/045287, filed Aug. 14, 2015, which claims priority under 35 U.S.C. § 119(e) from U.S. Ser. No. 62/037,676, filed Aug. 15, 2014, U.S. Ser. No. 62/065,993, filed Oct. 20, 2014, and U.S. Ser. No. 62/111,840 filed Feb. 4, 2015, the contents of which are incorporated herein by reference in their entireties.

2. TECHNICAL FIELD

The present disclosure relates to the synthesis of cephalosporins via a palladium catalyzed coupling reaction.

3. BACKGROUND

Cephalosporin compounds containing the chemical substructure of formula (I) are important antibacterial therapeutic agents. The manufacture of several known cephalosporin compounds involves forming new bonds at an allylic carbon indicated by $C^1$ in the structure below:

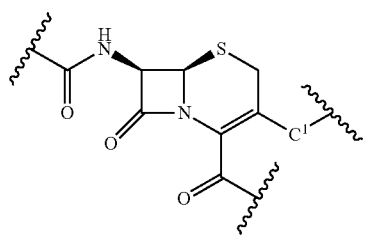

(I)

This allylic moiety is found, for example, in ceftolozane, a cephalosporin antibacterial agent, also referred to as CXA-101, FR264205, or by chemical names such as (6R,7R)-3-[(5-amino-4-([(2-aminoethyl)carbamoyl]amino)-1-methyl-1H-pyrazol-2-ium-2-yl)methyl]-7-({(2Z)-2-(5-amino-1,2,4-thiadiazol-3-yl)-2-[(1-carboxy-1-methylethoxy)imino]acetyl}amino)-8-oxo-5-thia-1-azabicyclo[4.2.0]oct-2-ene-2-carboxylate, and 7β-[(Z)-2-(5-min-1,24-thiadiazol-3-yl)-2-(1-carboxy-1-methylethoxyimino)acetamido]-3-{3-amino-4-[3-(2-aminoethyl)ureido]-2-methyl-1-pyrazolio}methyl-3-cephem-4-carboxylate. Ceftolozane sulfate is a pharmaceutically acceptable ceftolozane salt of compound (VII), that can be formulated for intravenous administration or infusion.

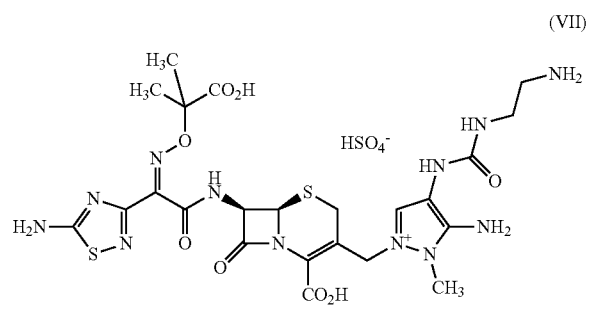 [SMILES: Cn1c(N)c(NC(=O)NCCN)c[n+]1CC1=C(C(=O)O)N2C(=O)[C@@H](NC(=O)/C(=N\OC(C)(C)C(=O)O)c3nsc(N)n3)[C@H]2SC1 ; "HSO4-"]

(VII)

Ceftolozane can be obtained using methods described in U.S. Pat. Nos. 7,129,232 and 7,192,943, as well as Toda et al., "Synthesis and SAR of novel parenteral anti-pseudomonal cephalosporin's: Discovery of FR264205." *Bioorganic & Medicinal Chemistry Letters,* 18, 4849-4852 (2008), each of which are incorporated herein by reference in their entirety. These methods are illustrated in FIGS. 1A and 1B.

There remains a need to identify novel manufacturing processes for synthesizing cephalosporin compounds comprising the chemical substructure of formula (I) such as, for example, ceftolozane.

4. SUMMARY

Provided herein are methods for the synthesis of cephalosporin compounds of formula (I) employing a palladium-catalyzed alkylation reaction, as well as compositions related to the same.

In an aspect, provided herein is a method for preparing a compound of formula (II), or a salt thereof.

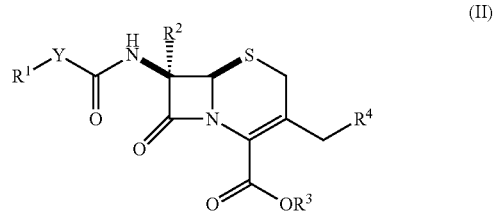

(II)

comprising the step of admixing. e.g., reacting, a compound of formula (III), or a salt thereof,

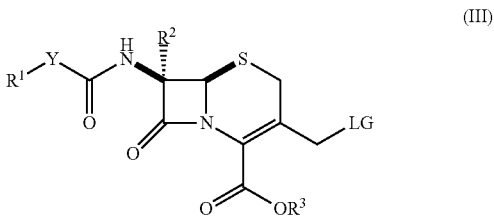

(III)

with a nucleophile (Nuc) in the presence of reagents comprising: (a) a palladium source; and (b) a palladium-binding ligand, to form a compound of formula (II), or a salt thereof.

In another aspect, provided herein is a composition comprising a compound of formula (Va) and palladium.

In another aspect, provided herein is a method for preparing a compound of formula (VII):

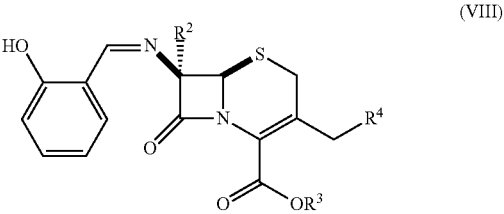

(VIII)

or a salt thereof, comprising the step of admixing, e.g., reacting, a compound of formula (IX)

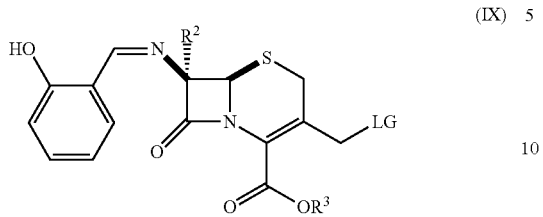
(IX)

or a salt thereof, with a nucleophile (Nuc)(e.g., $R^4$-M) in the presence of reagents comprising: (a) a palladium source and (b) a palladium-binding ligand, to form a compound of formula (VIII), or a salt thereof.

The nucleophile, palladium source, palladium-binding ligand, and variables of compounds of formulae (II), (III), (VIII) and (IX) are defined herein.

In some embodiments, the method comprises removal of palladium.

In some embodiments, the method comprises recovery of palladium.

5. BRIEF DESCRIPTION OF THE FIGURES

FIG. 1A is an example synthetic scheme showing known methods of ceftolozane synthesis (See. e.g., U.S. Pat. Nos. 7,129,232 and 7,192,943, as well as Toda et al., "Synthesis and SAR of novel parenteral anti-pseudomonal cephalosporins: Discovery of FR264205." Bioorganic & Medicinal Chemistry Letters, 18, 4849-4852 (2008)).

6. DETAILED DESCRIPTION

Provided herein are methods of using palladium catalysis for substitution of the $C^1$ position of compounds of formula (I), and related compositions.

Figure 1A:
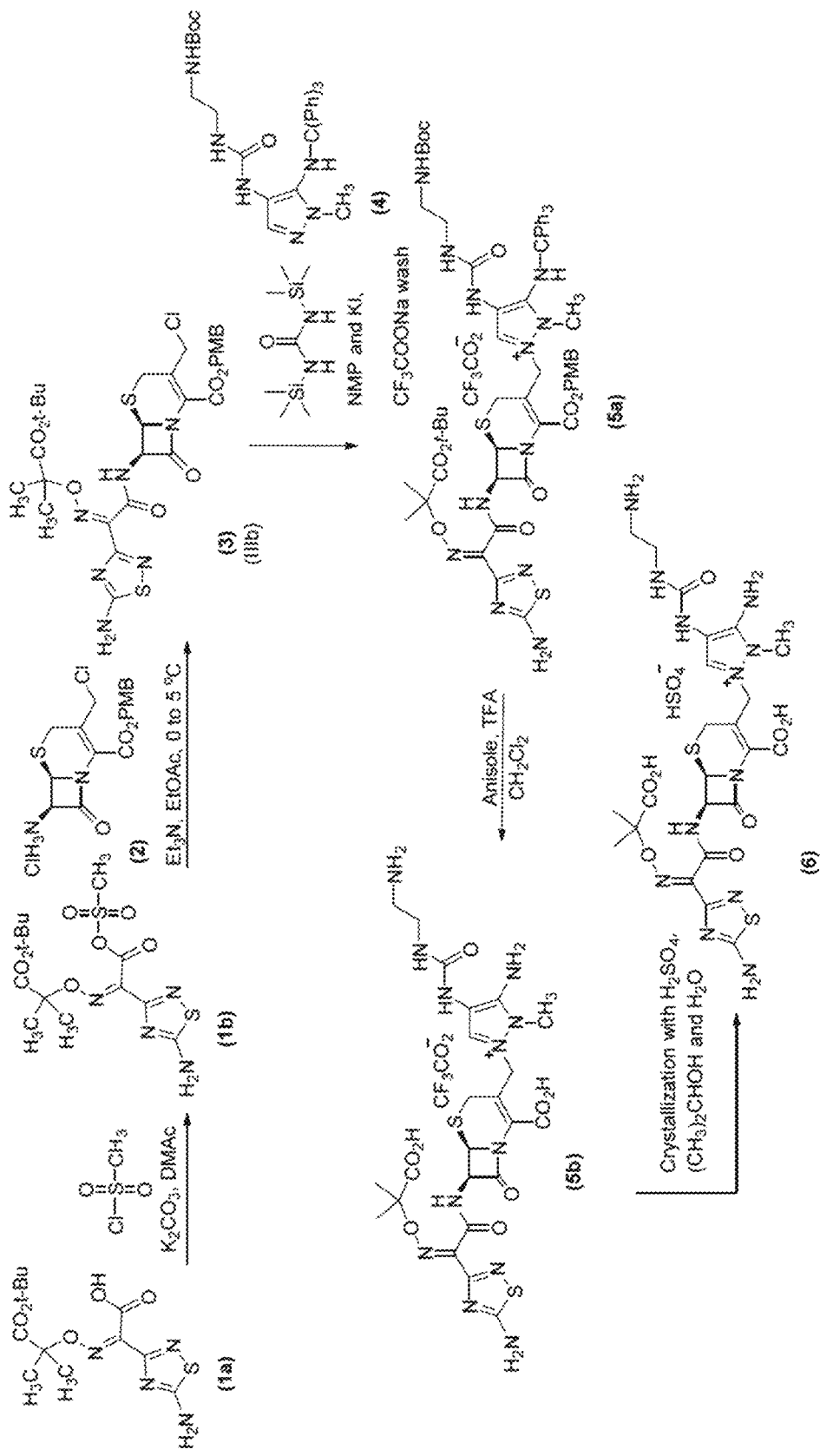
FIG. 1B is a synthetic scheme for preparing a ceftolozane starting material, a protected 5-amino-1-methylpyrazole. (See. e.g., Toda et al., "Synthesis and SAR of novel parenteral anti-pseudomonal cephalosporins: Discovery of FR264205," Bioorganic & Medicinal Chemistry Letters. 18, 4849-4852 (2008)).

The methods provided herein offer several advantages over the methods previously disclosed, including higher yields, higher purity, faster reaction time, and use of lower amounts of solid reagents compared to, for example, the analogous reaction for the conversion of compound 3 to compound 5a as shown in FIG. 1A.

In one aspect, provided herein is a method for preparing a compound of formula (II):

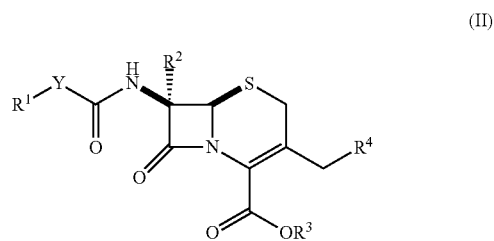
(II)

or a salt thereof comprising the step of admixing. e.g., reacting, a compound of formula (III)

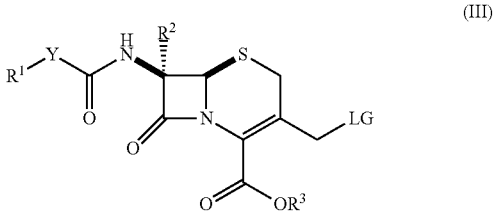
(III)

or a salt thereof, with a nucleophile (Nuc)(e.g., R-M) in the presence of reagents comprising:
  (a) a palladium source; and
  (b) a palladium-binding ligand;
to form a compound of formula (II), or a salt thereof.

The nucleophile, palladium source, palladium-binding ligand, and variables of compounds of formulae (II) and (III) are defined below.

Nucleophile (Nuc)

Nucleophiles include carboxylic acid, alcohols, water, amides, ureas, thiols, N-containing heteroaryls (e.g., optionally substituted pyrazoles) and N-containing heterocycles. These nucleophiles can be used in an anionic form, e.g. as carboxylates, hydroxides, and alkoxides.

In an embodiment, Nuc is $R^4$-M, wherein
M is H, a metal cation, a non-metal cation, or lone pair of electrons; and
$R^4$ is selected from the group consisting of carboxylates, hydroxides, alkoxides, ureas, N-containing heteroaryls and N-containing heterocycles, wherein said carboxylates, alkoxides, thiolates.
N-containing heteroaryls and N-containing heterocycles are optionally substituted.

M can be a metal selected from, for example, alkali metals, alkaline earth metals, transition metals, and main group metals. For metal cations having a formal charge greater than one (e.g., 2), more than one equivalent of $R^4$ will be present in the Nuc (e.g., $(R^4)_2M$).

One skilled in the art will recognize that the formal charge of R changes when a lone pair reacts to form a bond.

In one embodiment, M is H, a metal cation or a non-metal cation, and $R^4$ is selected from the group consisting of:

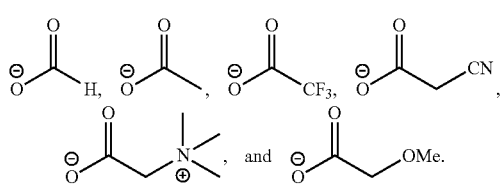

In another embodiment, M is H and R⁴-M is selected from the group consisting of

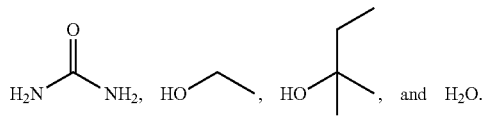

In another embodiment, M is a lone pair of electrons and R⁴-M is:

In still another embodiment. M is a lone pair of electrons and R⁴-M is a compound of formula (X):

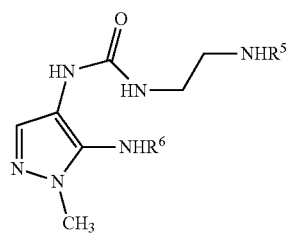
(X)

wherein R⁵ is a nitrogen protecting group; and R⁶ is a nitrogen protecting group.

In some embodiments, the compound of formula (X) has the structure of formula (UBT):

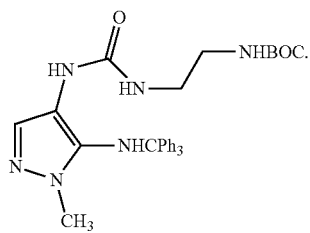
(UBT)

Figure 1B:
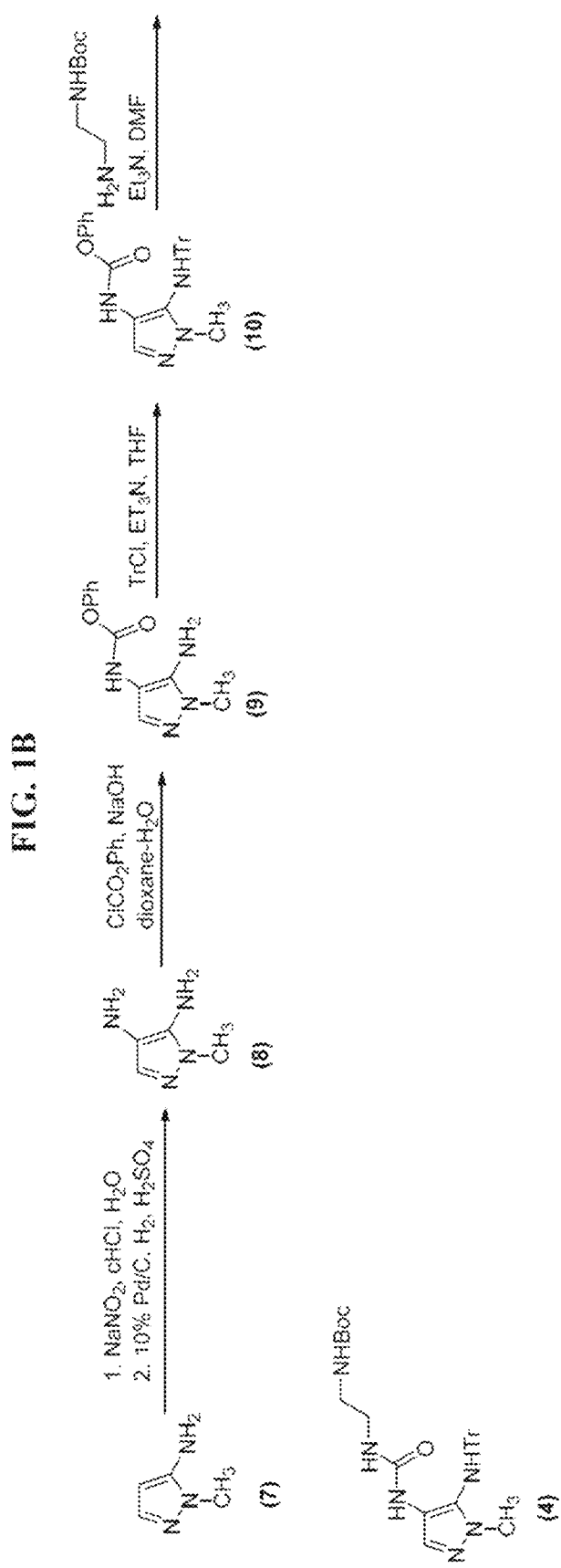
Figure 2:
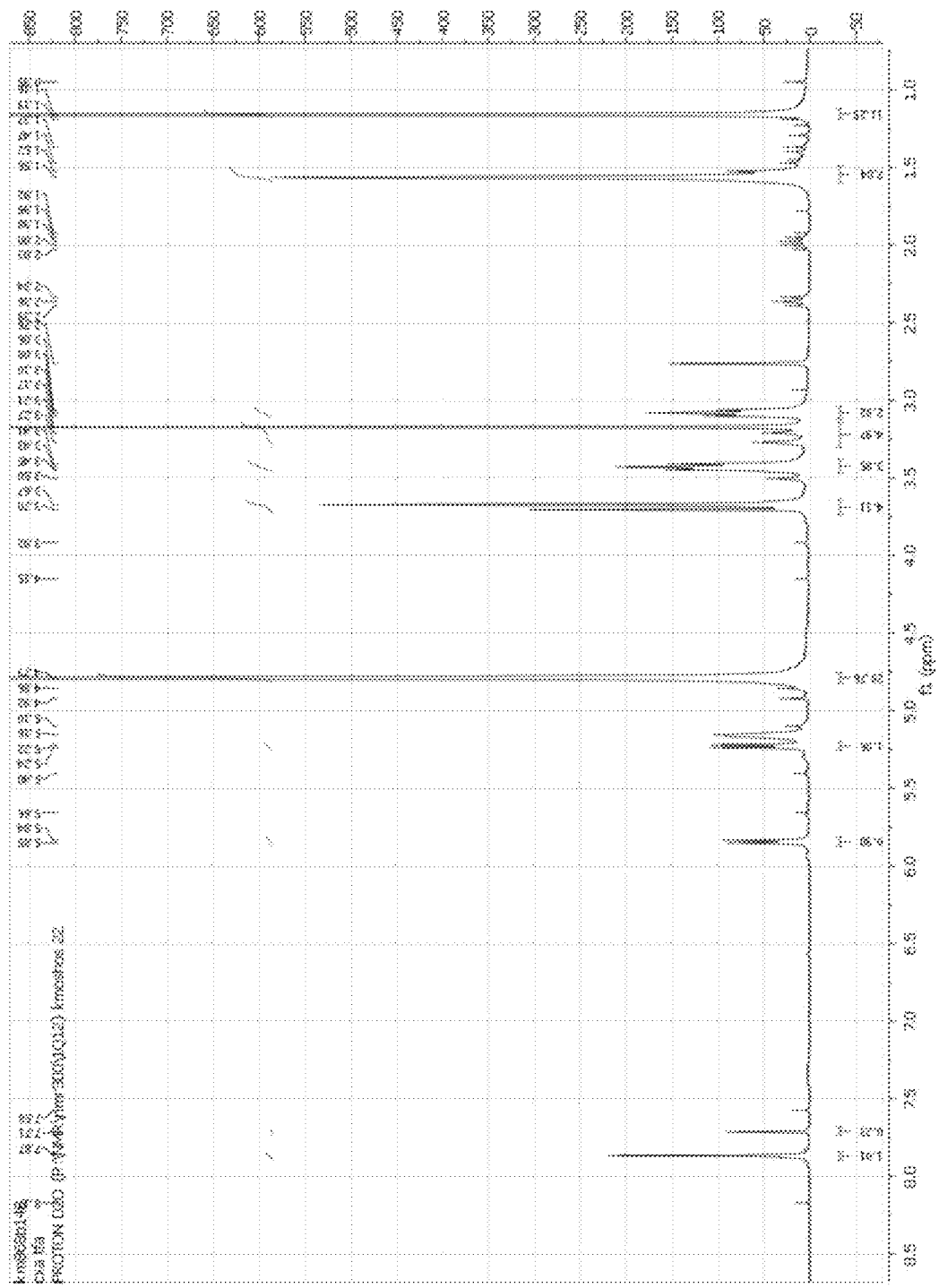
FIG. 2 is a reference $^1$H NMR spectrum of isolated ceftolozane TFA.

An example of the synthesis of this nucleophile, a protected 4-amino-5-amino-1-methylpyrazole, is found in FIG. 1B.

Variable LG

LG is a leaving group. In certain embodiments. LG is halo. —O(C=O)N(R¹⁸)₂. —O(C=O)OR¹⁸ and —OC(O)R¹⁸, wherein R¹⁸ is independently in each instance selected from the group consisting of $C_{1-6}$ alkyl and haloalkyl (e.g., —CF₃). In certain embodiments. LG is halo or —OC(O)R¹⁸, wherein R¹⁸ is selected from the group consisting of $C_{1-6}$ alkyl and haloalkyl (e.g., —CF₃). In a particular embodiment, LG is chloride or —OC(O)CF₃. In some embodiments, the haloalkyl is a $C_{1-6}$ haloalkyl.

Variable R¹

In certain embodiments. R¹ is R¹'—Z; wherein R¹' is selected from the group consisting of a bond, aryl, cycloalkyl, cycloalkenyl, heterocyclyl, and heteroaryl; wherein Z is 1-2 instances of a substituent that for each occurrence is independently selected from the group consisting of hydrogen, halogen, hydroxyl, hydroxyalkyl, aminoalkyl, alkyl, alkylidenyl, alkenyl, heteroalkyl, cyano and amino, wherein Z is optionally, independently substituted one or more times with amino, halogen, carboxyl, carboxamide, oxo, a nitrogen protecting group, an oxygen protecting group or —P(O)(OZ')₂; and wherein Z' is independently hydrogen or an oxygen protecting group.

In one embodiment. R¹ is selected from the group consisting of aryl and heteroaryl moieties. In certain embodiments. R¹ is a substituted or unsubstituted aryl or heteroaryl moiety selected from the group consisting of: thiophene, furan thiazole, tetrazole, thiadiazole, pyridyl, phenyl, phenol, cyclohexadiene and dithietane. In a particular embodiment, R¹ is selected from the group consisting of the following moieties:

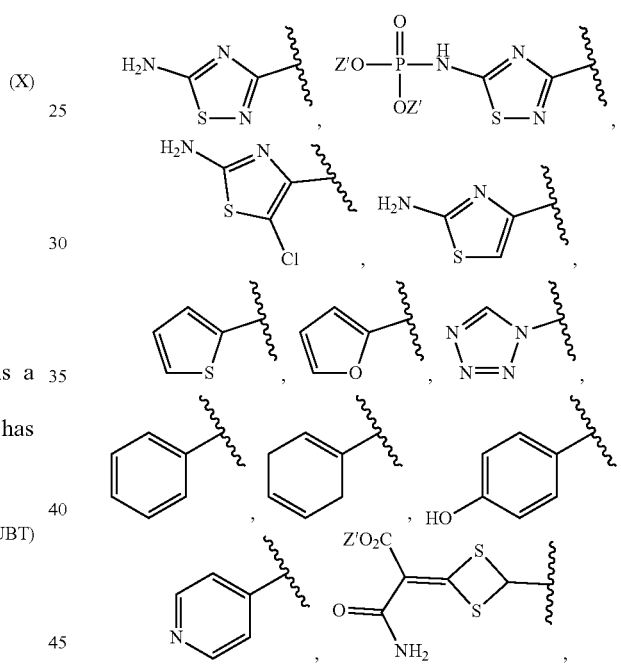

and salts thereof wherein Z' is as defined herein. In some embodiments, R¹ is selected from the group consisting of:

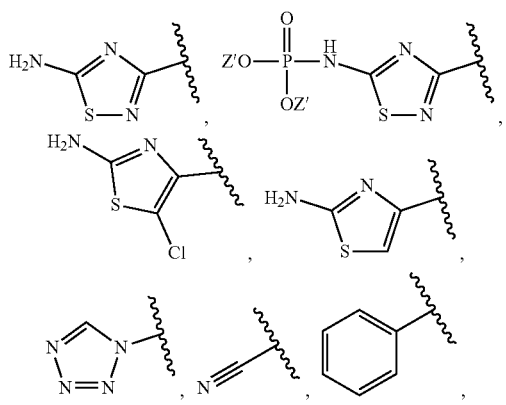

-continued

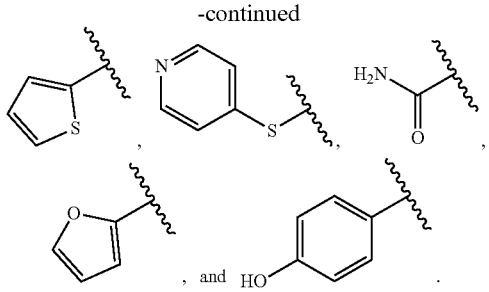

In some embodiments. R¹ is

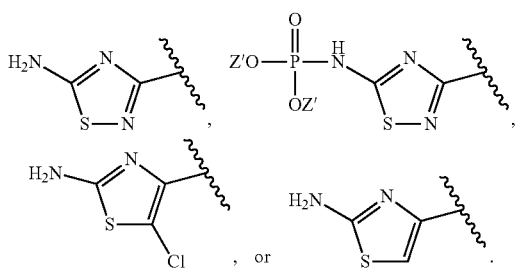

In a particular embodiment, R¹ is

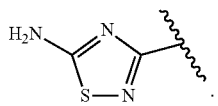

In another particular embodiment, R¹ is

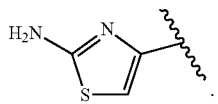

In some embodiments, Z' is a $C_{1-6}$ alkyl, such as Me, Et, or tert-butyl. In some embodiments. Z' is abase-labile oxygen protecting group, such as but not limited to —COMe, —COEt, and —(CO)-propyl. In some embodiments. Z' is an oxygen protecting group that is removed under reductive conditions. e.g., catalytic hydrogenation, such as benzyl. In some embodiments, Z' is an acid-labile oxygen protecting group, such as but not limited to tert-butyl 4-methoxybenzyl, 2-methoxybenzyl, or triphenylmethyl, preferably tert-butyl.

Variable R²

In certain embodiments. R² is selected from the group consisting of hydrogen and alkoxy. In a particular embodiment of the method, R² is hydrogen.

Variable Y

In certain embodiments. Y is selected from the group consisting of a bond, $CH_2$, $CH_2S$, $SCH_2$. C=C(H)$CH_2CO_2R'$. CH(OR'), C=N(OR'). CHN(R") and C=NR"; wherein R' is selected from the group consisting of hydrogen, an oxygen protecting group and alkyl, wherein the alkyl is optionally substituted one or more times with halogen, hydroxyl or —$CO_2R^{15}$; wherein R" is a substituent that for each occurrence is selected from hydrogen, alkyl, C(O) heterocyclyl, and a nitrogen protecting group, wherein any two R" substituens may combine to form a ring or a single nitrogen protecting group; and wherein $R^{15}$ is independently hydrogen or an oxygen protecting group.

In some embodiments. R' is a $C_{1-6}$ alkyl, such as Me. Et, or tert-butyl. In some embodiments R' is abase-labile oxygen protecting group, such as but not limited to —COMe, —COEt, and —(CO)-propyl. In some embodiments. R' is an oxygen protecting group that is removed under reductive conditions. e.g., catalytic hydrogenation, such as benzyl. In some embodiments. R' is an acid-labile oxygen protecting group, such as but not limited to tert-butyl, 4-methoxybenzyl, 2-methoxybenzyl, or triphenyhmethyl, preferably tert-butyl.

In some embodiments, Y is selected from the group consisting of —$CH_2$—,

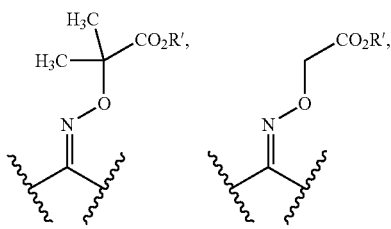

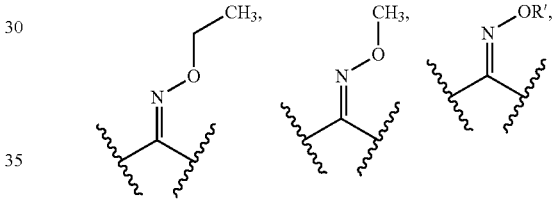

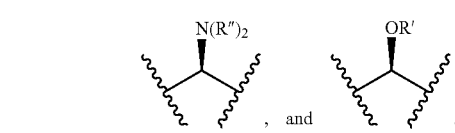

, and

In one embodiment of the method, Y is selected from a bond, $CH_2$, $CH_2S$ and C=C(H)$CH_2CO_2R'$, and R' is selected from the group consisting of hydrogen and an oxygen protecting group. In another embodiment, Y is C=N(OR') and R' is selected from the group consisting of an oxygen protecting group, hydrogen, methyl, ethyl. $CH_2CO_2R^{15}$ and $C(CH_3)_2CO_2R^{15}$. In yet another embodiment, Y is CH(OR') and R' is hydrogen or an oxygen protecting group. In still another embodiment Y is CHN (R")₂ and R", for each occurrence, is independently selected from hydrogen, a nitrogen protecting group and

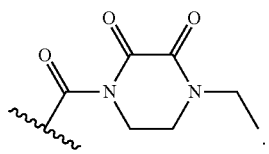 [SMILES: *C(=O)N1CCN(CC)C(=O)C1=O]

In a particular embodiment. Y is C=N(OR') and R' is $C(CH_3)_2CO_2{}^tBu$.

In some embodiments. Y is

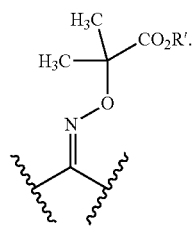

Variable $R^3$

In certain embodiments, $R^3$ is selected from the group consisting of hydrogen and an oxygen protecting group.

In some embodiments. $R^3$ is a $C_{1-6}$ alkyl, such as Me. Et, or tert-butyl. In some embodiments. $R^3$ is a base-labile oxygen protecting group (i.e., one that is removed under basic conditions), such as but not limited to Me. Et, and propyl. In some embodiments. $R^3$ is a protecting group that can be removed under hydrogenation conditions, such as benzyl. In some embodiments. $R^3$ is an acid-labile oxygen protecting group (i.e., one that is removed under acid conditions), such as but not limited to tert-butyldimethylsilyl, tert-butyl, 4-methoxybenzyl, 2-methoxybenzyl, or triphenylmethyl.

In another embodiment of the method, $R^3$ is an oxygen protecting group selected from benzyl ethers. Benzyl ethers may be substituted (e.g., with one or more alkoxy substituents) or unsubstituted. In a particular embodiment, $R^3$ is

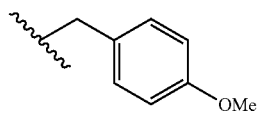 [SMILES: *Cc1ccc(OC)cc1]

(i.e., 4-methoxybenzyl, PMB, MPM).

Variable $R^4$ $R^4$ is the radical resulting from addition of the Nuc (e.g., $R^4$-M) as described below.

In an embodiment, $R^4$ is carboxyl, hydroxyl, alkoxy, urea, urea adduct, N-containing heteroaryl or N-containing heterocyclyl, wherein said carboxyl, alkoxy, N-containing heteroaryl and N-containing heterocyclyl are optionally substituted.

In some embodiments, $R^4$ is a N-containing heteroaryl (i.e., nitrogen-containing heteroaryl, or a heteroaryl containing at least one nitrogen in the ring). Nitrogen-containing heteroaryls include but are not limited to pyrazoles, pyrroles, triazoles, pyridines, pyrimidines, thiazoles, and thiadiazoles, each of which can be optionally substituted. In some embodiments, $R^4$ is a pyrazole, pyrrole, triazole, or pyridine, which are each optionally substituted. In some embodiments, $R^4$ is a pyrazole or a pyridine, which are each optionally substituted. In some embodiments, $R^4$ is an unsubstituted pyridine. In some embodiments, the N-containing heteroaryl is attached to the rest of the compound of formula (II) through the heteroaryl ring N atom (i.e., a ring N-linked nitrogen-containing heteroaryl).

In an embodiment, $R^4$ is selected from the group consisting of

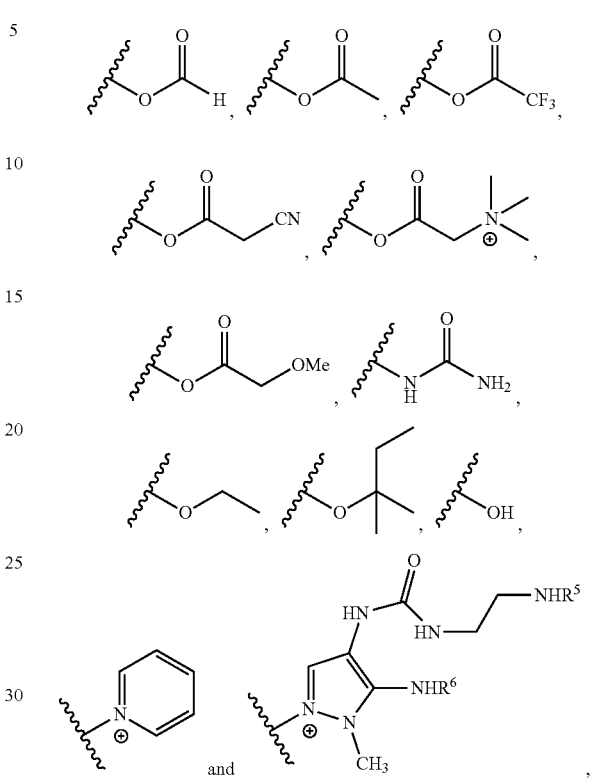

wherein $R^5$ is a nitrogen protecting group; and $R^6$ is a nitrogen protecting group.

In one embodiment, $R^4$ is:

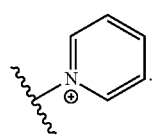 [SMILES: *[n+]1ccccc1]

In some embodiments. $R^4$ is a substituted pyrazole. In some embodiments. $R^4$ is a substituted pyrazole that has one, two, three, or four substituents. In some embodiments. $R^4$ is a pyrazole substituted with a $C_{1-6}$ alkyl. In some embodiments, $R^4$ is a pyrazole substituted with a urea. In some embodiments. $R^4$ is a pyrazole substituted with an amine.

In an embodiment. $R^4$ is

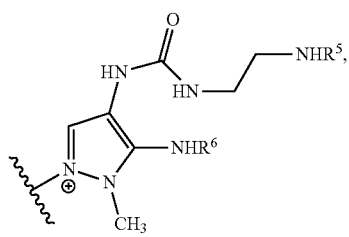

which is the result of addition of Nuc (i.e., $R^4$-M, wherein M is lone pair of electrons), e.g., a compound of formula (X):

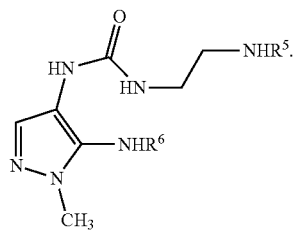

(X)

In some embodiments, $R^5$ is an acid-labile nitrogen protecting group. In some embodiments. $R^5$ is tert-butyloxycarbonyl.

In some embodiments, $R^6$ is an acid-labile nitrogen protecting group. In some embodiments, $R^6$ is triphenylmethyl.

In some embodiments. $R^5$ and $R^6$ are each independently an acid-labile nitrogen protecting group. In some embodiments. $R^5$ and $R^6$ are each independently triphenylmethyl, tert-butyl, tert-butoxycarbonyl, 2-trimethylsilylethoxycarbonyl, or 4-methoxybenzyloxycarbonyl. In an embodiment, $R^5$ is tert-butyloxycarbonyl and $R^6$ is triphenylmethyl.

In an embodiment, R' is tert-butyl; $R^3$ is 4-methoxy benzyl ether (i.e., 4-methoxybenzyl); $R^5$ is tert-butyloxycarbonyl; and $R^6$ is triphenyhoethyl.

In some embodiments, the compound of formula (II) has the structure of formula (II'):

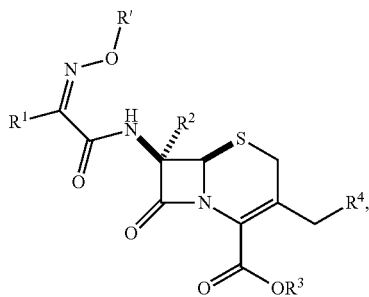

(II')

wherein $R^1$, $R^2$, $R^3$. $R^4$, and R' are as described herein.

Palladium Source

The term "palladium source" indicates a source of palladium. In some embodiments, the palladium source is any source that is known to facilitate palladium π-allyl chemistry, including but not limited to solvent-soluble palladium catalysts and palladium on solid support, such as palladium (0) on carbon black powder. Solvent-soluble palladium catalysts include palladium(II) catalysts, such as bis(acetonitrile)dichloropalladium(II), bis(acetylacetonate)palladium (II), bis(benzonitrile)palladium(II) chloride, bis(dibenzylideneacetone)palladium, palladium(II) acetate, palladium (II) trifluoroacetate, allylpalladium(II) chloride dimer, palladium(II) chloride, palladium(II) bromide, tetrakis(acetonitrile)palladium(II) tetrafluoroborate, [1,2-bis(diphenylphosphino)ethane] dichloropalladium(II), 1,1'-bis(diphenylphosphino)ferrocene-palladium(II)dichloride dichloromethane adduct, bis(tricyclohexylphosphine)palladium(0), bis(triethylphosphine)palladium(II) chloride, bis(triphenylphosphine)palladium(II) acetate, bis(triphenylphosphine)palladium(II) chloride, bis[tri(o-tolyl)phosphine]palladium(II) chloride, dichlorobis(tricyclohexylphosphine)palladium(II), and trans-benzyl(chloro)bis(triphenylphosphine)palladium(II), and palladium(0) catalysts, such as tetrakis(triphenylphosphine)palladium(0), bis[1,2-bis(diphenylphosphino)ethane]palladium(0), bis(tri-t-butylphosphine)palladium(0), bis(dibenzylideneacetone)palladium(0) and tris(dibenzylideneacetone)dipalladium(0) (i.e., $Pd_2dba_3$, in free and solvate form, e.g., as a chloroform adduct). For example, the palladium source can comprise tris(dibenzylideneacetone)dipalladium(0), e.g., consist or consist essentially of tris(dibenzylideneacetone)dipalladium(0).

In an embodiment, the palladium source comprises palladium(0) or a palladium(II) salt, optionally as complexes (e.g., further comprising ligands). A non-limiting list of palladium sources includes: allylpalladium(II) chloride dimer, bis(acetonitrile)dichloropalladium(II), bis(acetylacetonate)palladium(II), bis(benzonitrile)palladium(II) chloride, bis(dibenzylideneacetone)palladium, palladium(II) acetate, palladium(II) trifluoroacetate, palladium(II) chloride, palladium(II) bromide, tetrakis(acetonitrile)palladium (II) tetrafluoroborate, tris(dibenzylideneacetone)dipalladium(0), tris(dibenzylideneacetone) dipalladium(0)-chloroform adduct, [1,2-bis(diphenylpbosphino)ethane] dichloropalladium(II), 1,1'-bis(diphenylphosphino)ferrocene-palladium(II)dichloride dichloromethane adduct, bis(tricyclohexylphosphine)palladium(0), bis(triethylphosphine)palladium(II) chloride, bis(triphenylphosphine) palladium(II) acetate, bis(triphenylphosphine)palladium(II) chloride, bis(tri-t-butylphosphine)palladium(0), bis[1,2-bis(diphenylphosphino)ethane]palladium(0), bis[tri(o-tolyl)phosphine]palladium(II) chloride, dichlorobis(tricyclohexylphosphine)palladium(II), tetrakis(triphenylphosphine)palladium(0), tetrakis(triethylphosphine)palladium(0), and trans-benzyl(chloro)bis(triphenylphosphine)palladium(II).

In an embodiment, the palladium source is selected from the group consisting of allylpalladium(II) chloride dimer, tris(dibenzylideneacetone)dipalladium(0), tris(dibenzylideneacetone)dipalladium(0)-chloroform adduct, tetrakis(triphenylpbosphine)palladium, palladium(II) acetate, palladium (II) trifluoroacetate, palladium(II) chloride, palladium(II) bromide, and bis(acetonitrile)dichloropalladium(II).

In an embodiment, the palladium source is tris(dibenzylideneacetone)dipalladium(0).

In some embodiments, palladium-catalyzed reactions offer a metal-mediated reaction that as compared to a non-metal-catalyzed reaction result in higher yields and/or cleaner formation of desired product(s). Typically, palladium-catalyzed reactions occur with a substoichiometric amount of both a palladium source and one or more palladium-binding ligands to facilitate the catalytic cycle.

In some embodiments, palladium-catalysis facilitates the reaction of two reagents to provide a higher molecular weight product. In some embodiments, the amounts of the two reagents are the same. In some embodiments the amounts of the two reagents are different. In cases where the amounts of the two reagents are different, the less abundant reagent is referred to as the limiting reagent.

In some embodiments, the palladium source is present in an amount of from about 0.2 mole % to about 5 mole % with respect to the compound of formula (III). In some embodiments, the palladium source is present in an amount of from about 0.2 mole % to about 1.5 mole % with respect to the compound of formula (III). In an embodiment, the palladium source is present in an amount of from about 0.5 mole % to about 5 mole % with respect to the compound of formula (III). In a further embodiment, the palladium source is present in an amount of from about 0.5 mole % to about 1.5 mole % with respect to the compound of formula (III). In yet another embodiment, the palladium source is present in an amount of about 1.0 mole % with respect to the compound of formula (III).

In some embodiments, the palladium source is present in about 0.2%, about 0.5%, about 1%, about 2%, about 3%, about 4%, or about 5% palladium on a molar basis compared to the molar amount of the limiting reagent.

In an illustrative example, 2 mol % tetrakis(triphenylphosphine)palladium(0) is 0.02 moles of palladium(0) per mole of the limiting reagent (e.g., a compound of formula (III)). In another example, 1 mol % tris(dibenzylideneacetone)dipalladium is 0.02 moles of palladium(0) per mole of the limiting reagent.

Palladium-Binding Ligand

The role of the palladium-binding ligand serves to stabilize the intermediate species within the palladium catalysis cycle while facilitating the formation of the desired reaction product(s). The molar ratio of the ligand to the metal can be modified to optimize reaction conditions, such as rate or yield. In some embodiments the molar ratio of palladium-binding ligand to palladium is in a range of from about 1:1 to about 10:1, such as about 1.5:1 to about 5:1, about 1.5:1 to about 4:1, about 2:1 to about 4:1, or about 3:1 to about 4:1.

In some embodiments, the palladium-binding ligand is an arsenic-based ligand, such as triphenylarsine.

Ligands that can be used in the disclosed coupling are phosphites or phosphines. Appropriate phosphine ligands include triphenylphosphine, tri-tert-butylphosphine, 2-dicyclohexylphosphino-2',6'-diisopropoxybiphenyl (RuPhos), 2-dicyclohexylphosphino-2',4',6'-triisopropylbiphenyl (XPhos), 4,5-bis(diphenyphosphino)-9,9'-dimethylxanthine (Xantphos), 1,2-bis(diphenylphosphino)ethane (dppe), and 1,3-bis(diphenylphosphino)propane (dppp).

In a preferred embodiment, the ligand is a phosphite ligand.

The palladium-binding ligand can be a phosphite ligand of formula (VI):

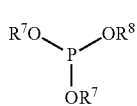
(VI)

wherein
$R^7$ is, at each occurrence, independently selected from phenyl heteroaryl, heterocycyl and $C_{1-6}$ alkyl, wherein said phenyl, heteroaryl, heterocyclyl, and $C_{1-6}$ alkyl are optionally substituted with one or more of halo. $C_{1-6}$ alkyl, $C_{1-6}$ alkoxy, or $N(R^9)_2$, and wherein said phenyl and heteroaryl are optionally further substituted with a fused $C_{3-6}$ cycloalkyl or $C_{3-6}$ heterocyclyl;
$R^8$ is selected from phenyl heteroaryl, heterocyclyl, and $C_{1-6}$ alkyl, wherein said phenyl, heteroaryl, heterocyclyl, and $C_{1-6}$ alkyl are optionally substituted with one or more of halo. $C_{1-6}$ alkyl, $C_{1-6}$ alkoxy, or $N(R^9)_2$, and wherein said phenyl and heteroaryl are optionally substituted with a fused $C_{3-6}$ cycloalkyl or $C_{3-6}$ heterocyclyl, or $R^8$ is

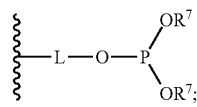

wherein
L is selected from the group consisting of —$(CH_2)_n$—,

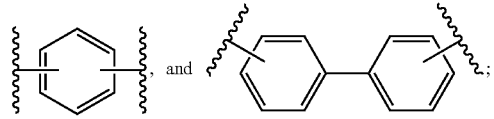

$R^8$ is optionally connected by a bond or —$(CH_2)_n$— to one $R^7$ to form a ring, or to each $R^7$ to form two rings;
each $R^9$ is $C_{1-6}$ alkyl, or two $R^9$ can combine to form a 3-10 membered heterocyclyl, wherein heterocyclyl comprises 1-3 nitrogen atoms and is optionally substituted by Ca alkyl or $C(O)$—$(C_{1-6}$ alkyl); and
n is 1, 2, or 3.

In another embodiment, $R^7$ is, at each occurrence, independently selected from phenyl and $C_{1-6}$ alkyl, wherein said phenyl and $C_{1-6}$ alkyl are optionally substituted with one or more of halo. $C_{1-6}$ alkyl, $C_{1-6}$ alkoxy, or $N(R^9)_2$ and wherein said phenyl is optionally further substituted with a fused cycloalkyl; and
$R^8$ is selected from phenyl and $C_{1-6}$ alkyl wherein said phenyl and $C_{1-6}$ alkyl are optionally substituted with one or more of halo, $C_{1-6}$ alkyl, $C_{1-6}$ alkoxy, or $N(R^9)_2$, and wherein said phenyl is optionally substituted with a fused cycloalkyl, or
$R^8$ is

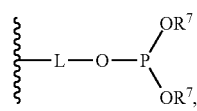

wherein
L is selected from the group consisting of —$(CH_2)_n$—,

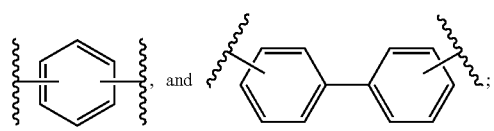

$R^8$ is optionally connected by a bond or —$(CH_2)_n$— to one $R^7$ to fort a ring, or to each $R^7$ to form two rings;
each $R^9$ is $C_{1-6}$ alkyl, or two $R^9$ can combine to form a 3-10 membered heterocyclyl, wherein heterocyclyl comprises 1-3 nitrogen atoms and is optionally substituted by $C_{1-6}$ alkyl or $C(O)$—$(C_{1-6}$ alkyl).

In another embodiment, $R^7$ is, at each occurrence, independently phenyl, optionally substituted with one or more of halo, $C_{1-6}$ alkyl. $C_{1-6}$ alkoxy, or $N(R^9)_2$ and wherein said phenyl is optionally further substituted with a fused cycloalkyl; and
$R^8$ is phenyl, optionally substituted with one or more of halo. $C_{1-6}$ alkyl, $C_{1-6}$ alkoxy, or $N(R^9)_2$, and wherein said phenyl is optionally substituted with a fused cycloalkyl, or R⁸ is

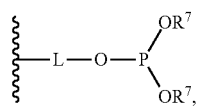

wherein

L is selected from the group consisting of —(CH₂)ₙ—,

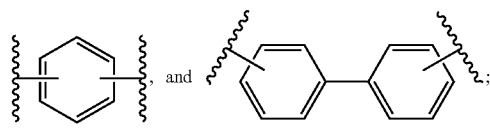

R⁸ is optionally connected by a bond or —(CH₂)ₙ— to one R⁷ to form a ring, or to each R⁷ to form two rings;

each R⁹ is $C_{1-6}$ alkyl, or two R⁹ can combine to form a 3-10 membered heterocyclyl, wherein heterocyclyl comprises 1-3 nitrogen atoms and is optionally substituted by $C_{1-6}$ alkyl or C(O)—($C_{1-6}$ alkyl).

In another embodiment, the palladium-binding ligand is a phosphite ligand selected from the group consisting of:

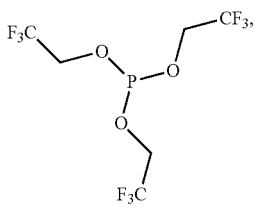

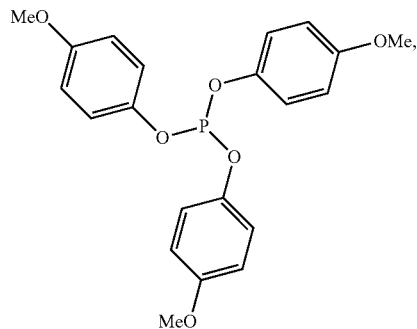

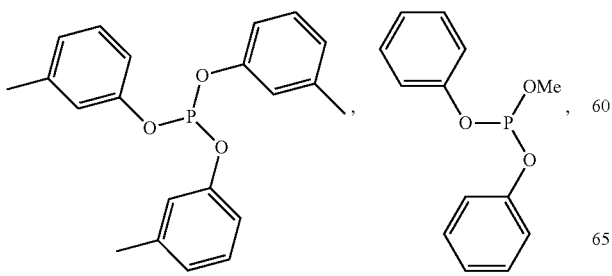

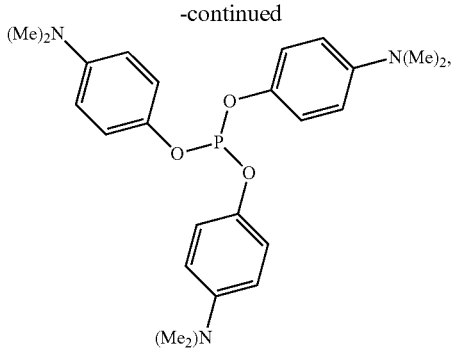

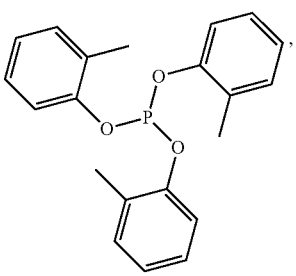

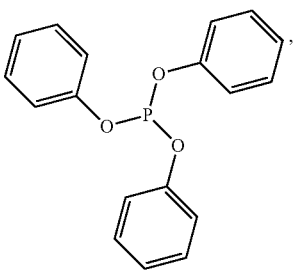

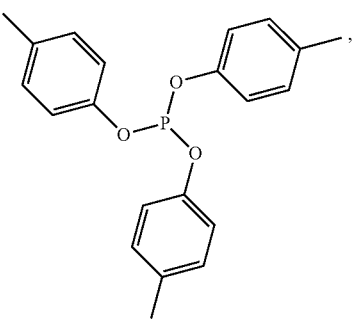

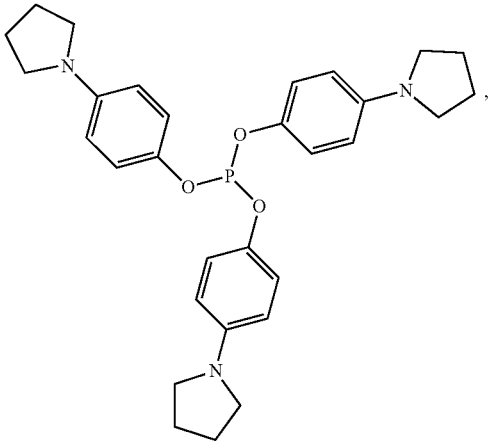

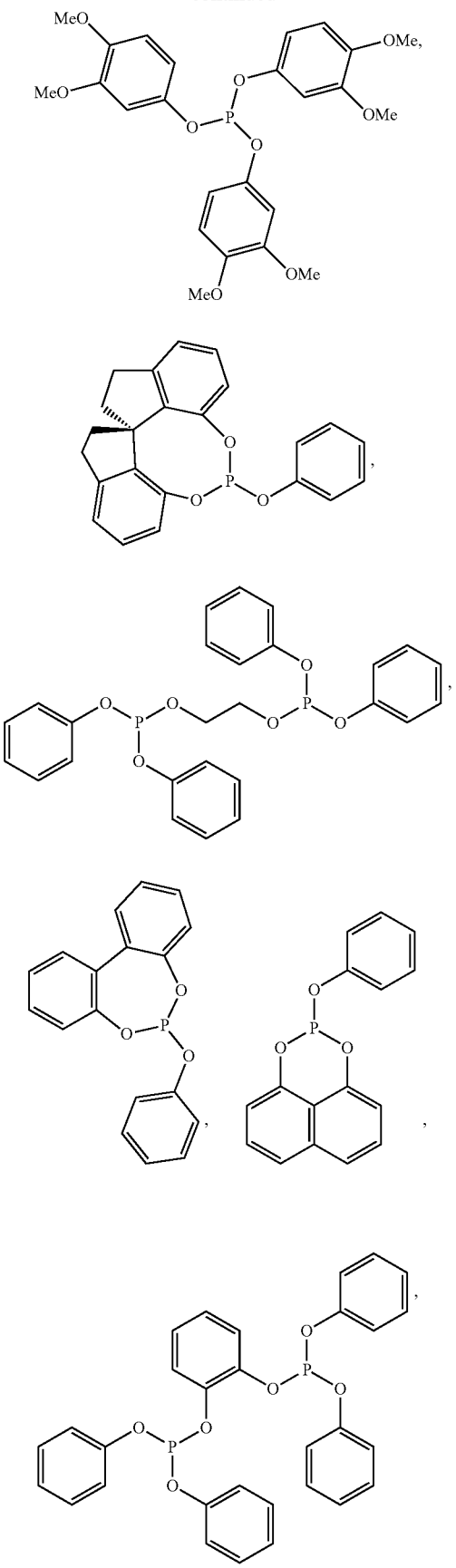
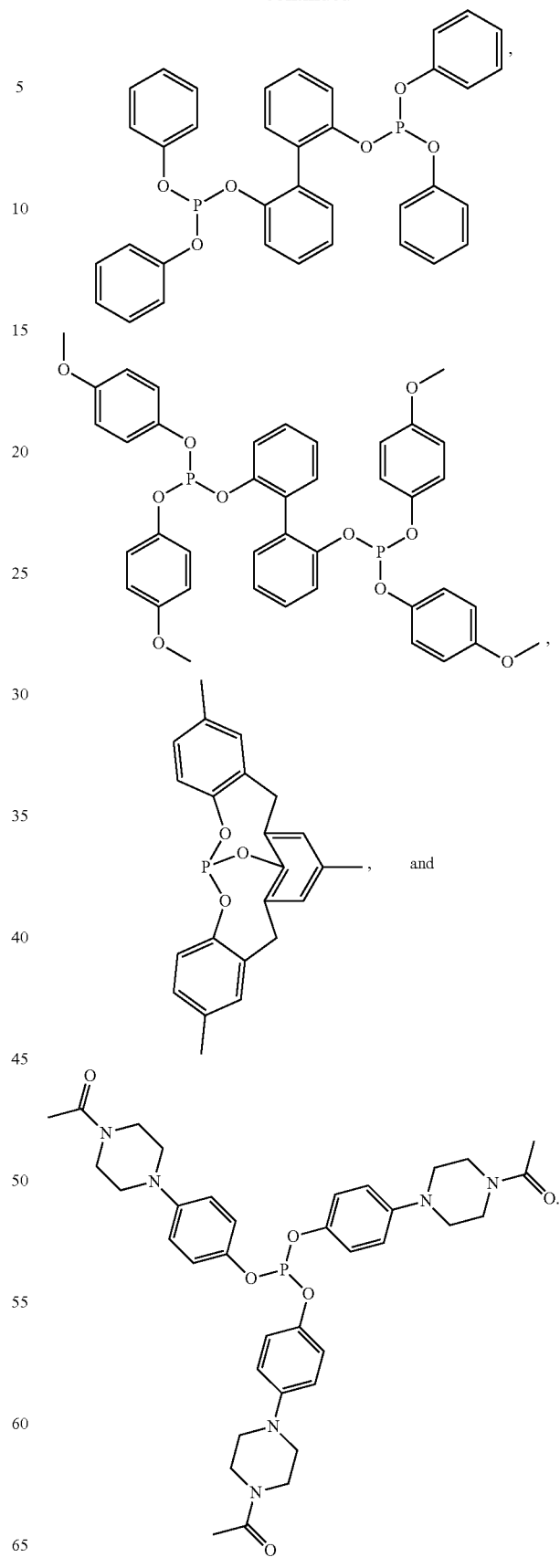

In some embodiments, the palladium-binding ligand is selected from the group consisting of:
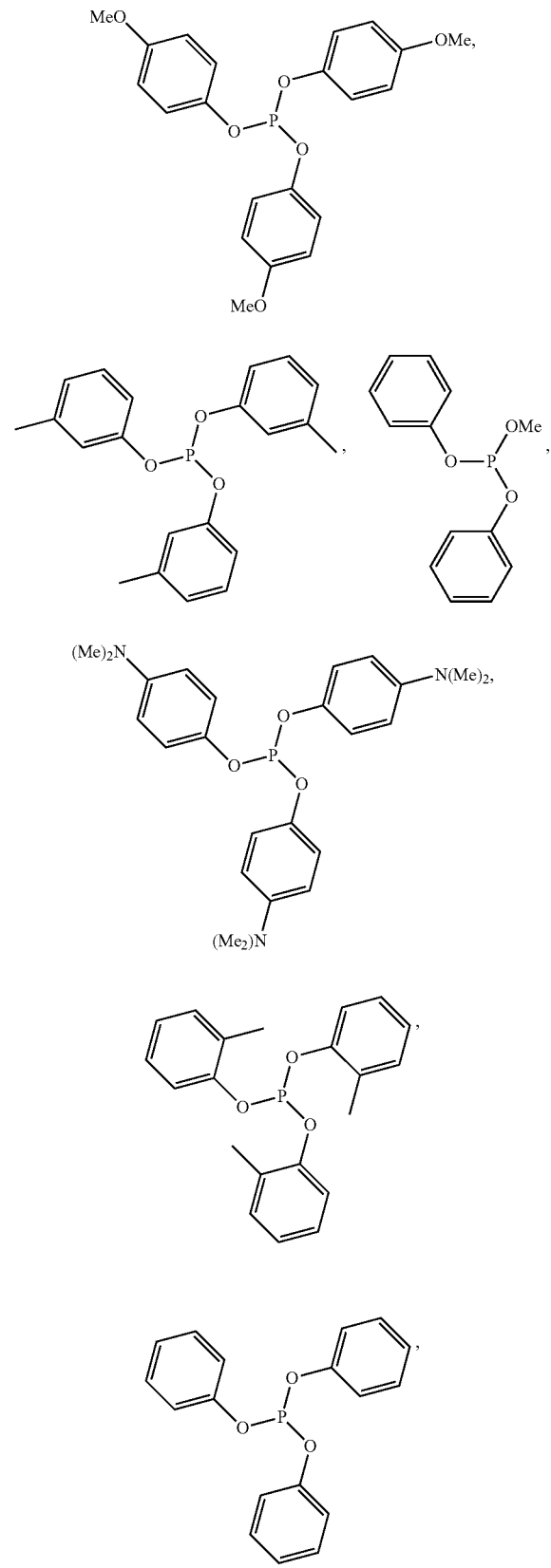
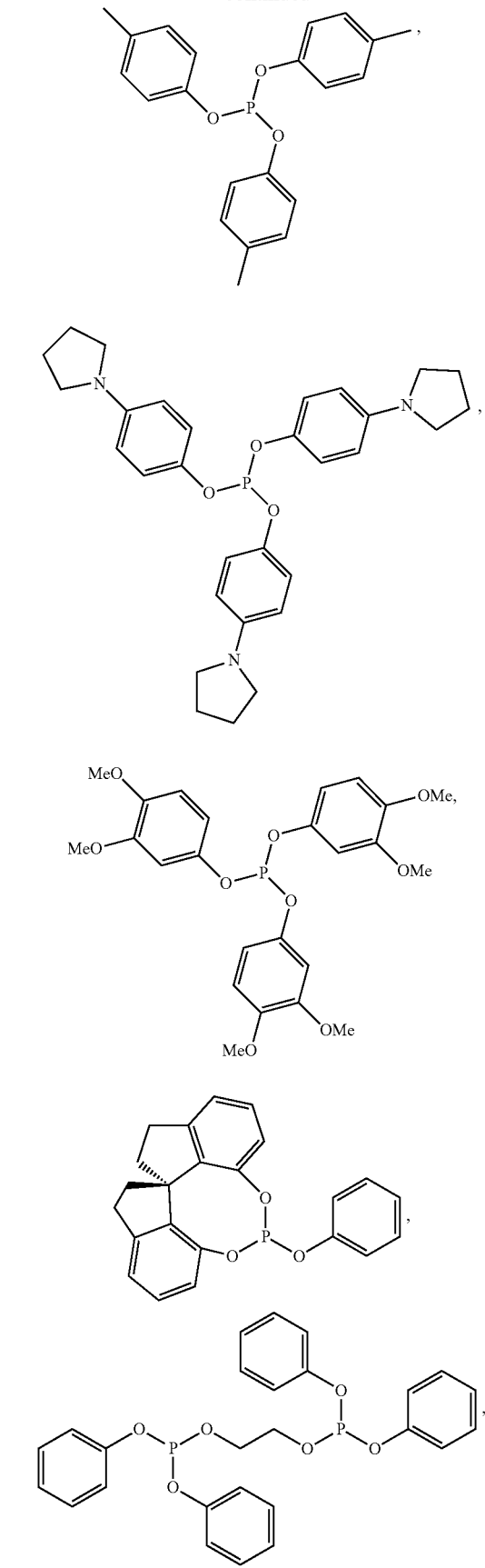

-continued

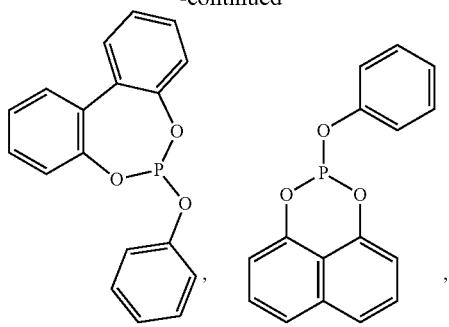

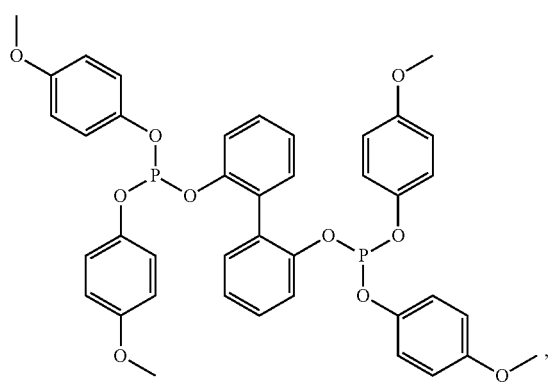

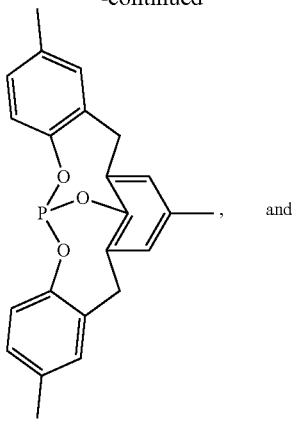

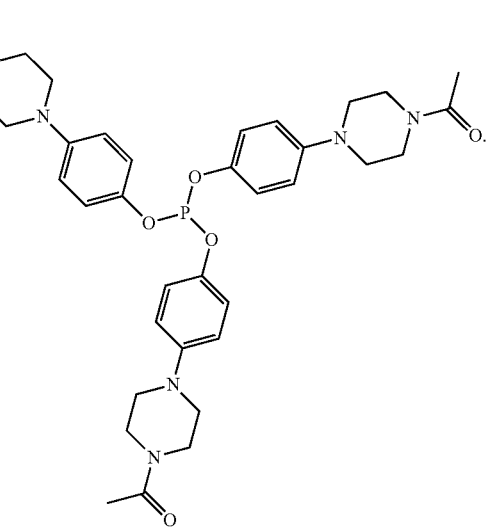

In a particular embodiment, the palladium-binding ligand is

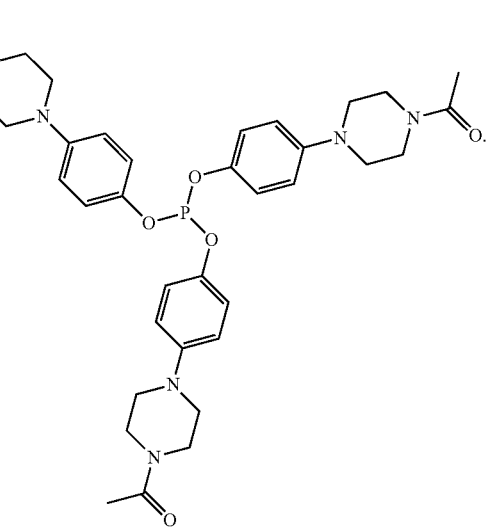

In an embodiment, the palladium-binding ligand is present in a molar ratio of between about 3:1 and about 10:1 with respect to the palladium source. In a further embodiment, the palladium-binding ligand is present in a molar ratio of about 3:1, about 4:1, about 5:1, about 6:1, about 7:1, about 8:1, about 9:1, or about 10:1 with respect to the palladium source.

In some preferred embodiments, the palladium-binding ligand is present in a molar ratio of between about 3:1 and about 6:1 with respect to the molar amount of palladium in the palladium source. In some preferred embodiments, the palladium-binding ligand is present in a molar ratio of about 3:1, about 4:1, about 5:1, or about 6:1 with respect to the molar amount of palladium in the palladium source.

In some embodiments, the palladium source and the palladium-binding ligand are included in one reagent as a pre-complexed palladium catalyst. In an illustrative example, tetrakis(triphenylphosphine)palladium(0) includes both a palladium(0) source and the palladium-binding ligand triphenylphosphine.

In some embodiments, the palladium source and the palladium-binding ligand comprise two reagents that are added to an admixture. In such cases, the palladium source and the palladium-binding ligand forms the active palladium catalyst within the admixture. In a preferred embodiment, the palladium source comprises tris(dibenzylideneacetone)dipalladium(0) and the palladium-binding ligand is

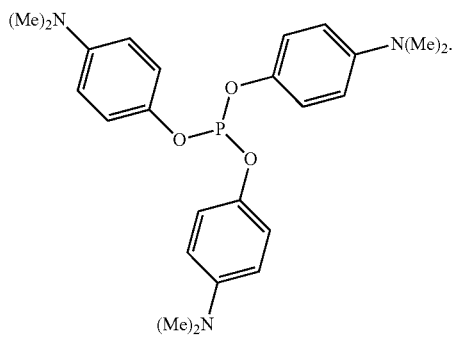

Salt Additive

The reagents of the method disclosed herein can also comprise a salt additive. The salt additive can be a potassium salt, sodium salt, lithium salt, silver salt, or copper salt. Suitable salts include, but are not limited to, potassium trifluoroacetate, sodium trifluoroacetate, lithium trifluoroacetate, potassium triflate, sodium triflate, lithium triflate, silver triflate and copper sulfate.

In an embodiment, the salt is selected from the group consisting of potassium trifluoroacetate, sodium trifluoroacetate, lithium trifluoroacetate, potassium triflate, sodium triflate, lithium triflate, silver triflate and copper sulfate.

In a particular embodiment, the salt is potassium trifluoroacetate.

In an embodiment, the salt additive is present in a molar ratio of between about 1:1 and about 5:1 with respect to the compound of formula (III). In another embodiment, the salt additive is present in a molar ratio of about 1:1, about 2:1 about 3:1, about 4:1 or about 5:1 with respect to the compound of formula (III). In a particular embodiment, the salt additive is present in a molar ratio of between about 2:1 and about 3:1 with respect to the compound of formula (III).

Anion ($A^\ominus$)

$A^\ominus$, for each occurrence, is independently a pharmaceutically acceptable anion. In some embodiments, $A^\ominus$ is chloride, bromide, iodide, sulfate, bisulfate, tosylate (i.e., tolenesulfanate) mesylate (i.e., methanesulfonate), edisylate, maleate, phosphate (e.g., monophosphate, biphosphate), ketoglutarate, trifluoroacetate, or triflate (i.e., tifluoromethanesulfonate). In certain embodiments, $A^\ominus$ is selected from chloride, acetate, trifluoroacetate and bisulfate (i.e., hydrogen sulfate). In a particular embodiment, $A^\ominus$ is trituroecetate or bisulfate (i.e., $HSO_4^-$). In certain embodiments, $A^\ominus$ is trifluoroacetate. In certain embodiments, $A^\ominus$ is bisulfate.

6.1. Definitions

The term "$C_{x-y}$ alkyl" refers to unsubstituted saturated hydrocarbon groups, including straight-chain alkyl and branched-chain alkyl groups that contain from x to y carbons in the chain. For example, $C_{1-6}$ alkyl is an alkyl group having one to six carbons.

The term "alkoxy" refers to an alkyl group having an oxygen attached thereto. Representative alkoxy groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxy.

The term "$C_{1-6}$ alkoxy" refers to an alkoxy group having one to six carbons.

The term "halo" or "halogen" as used herein refers to F, Cl, Br, or I.

The term "haloalkyl" refers to an alkyl group having one or more. e.g., one, two, or three, halogens. A "$C_{1-6}$ haloalkyl" is a haloalkyl with an alkyl group having one to six carbons. $C_{1-6}$ haloalkyls include chloroethyl ($ClCH_2CH_2$), fluoropropyl ($FCH_2CH_2$), and trifluoromethyl ($CF_3$).

The term "alkylidenyl" refers to the radical=$CR^aR^b$, wherein $R^a$ and $R^b$ are each independently hydrogen or alkyls.

The term "alkenyl" and "alkynyl" refer to unsubstituted unsaturated aliphatic groups analogous in length to the alkyls described above, but that contain at least one double or triple bond, respectively.

The terms "amine" and "amino" are art-recognized and refer to both unsubstituted and substituted amines and salts thereof, e.g., a moiety that can be represented by the general formulae:

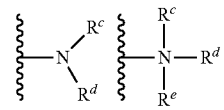

wherein $R^c$, $R^d$, and $R^e$ each independently represent a hydrogen, an alkyl, an alkenyl, —$(CH_2)_m$—$R^f$, or $R^c$ and $R^d$ taken together with the N atom to which they are attached complete a heterocycle having from 4 to 8 atoms in the ring structure; Rr represents an aryl, a cycloalkyl, a cycloalkenyl, a heterocyclyl or a polycyclyl; and m is zero or an integer from 1 to 8. In preferred embodiments, only one of $R^c$ and $R^d$ is a carbonyl. e.g., $R^c$, $R^d$, and the nitrogen together do not form an imide. In even more preferred embodiments, $R^c$ and $R^d$ (and optionally R) each independently represent a hydrogen, an alkyl, an alkenyl, or —$(CH_2)_m$—$R_f$. In certain embodiments, the amino group is basic, meaning the protonated form has a $pK_a \geq 7.00$.

The terms "amide", "amido", and "carboxamide" are art-recognized as an amino-substituted carbonyl and includes a moiety that can be represented by the general formula:

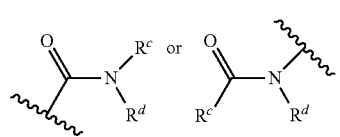

wherein $R^c$ and $R^d$ are as defined above. Preferred embodiment of the amide will not include imides which may be unstable.

The term "heteroatom" as used herein means an atom of any element other than carbon or hydrogen. Preferred heteroatoms are nitrogen, oxygen, phosphorus, and sulfur.

The term "hydroxyalkyl" refers to an alkyl group having one or more. e.g., one, two, or three, hydroxy (i.e., —OH) substituents.

The term "aminoalkyl" refers to an alkyl group having one or more, e.g., one, two, or three, amino substituents.

The term "carboxy" or "carboxyl" is art-recognized and refers to —COOH.

The term "carboxyalkyl" refers to carboxy substituents terminated by an alkyl group (i.e., an alkyl ester).

The term "urea" as used herein includes a moiety that can be represented by the general formula:

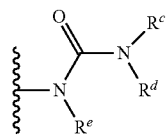

wherein $R^c$, $R^d$, and $R^e$ are as defined above.

The term "aryl" as used herein includes 5-, 6-, and 7-membered substituted or unsubstituted single-ring aromatic groups in which each atom of the ring is carbon. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The terms "carbocycle", "cycloalkyl", "carbocyclyl", as used herein, refer to a non-aromatic substituted or unsubstituted ring in which each atom of the ring is carbon.

The term "$C_{3-6}$ cycloalkyl" refers to a cycloalkyl having three to six carbons in the ring. Illustrative examples include a cyclopropyl ($C_3$ cycloalkyl) and a cyclopentyl ($C_5$ cycloalkyl).

The term "heteroaryl" includes substituted or unsubstituted aromatic 5- to 7-membered ring structures, more preferably 5- to 6-membered rings, whose ring structures include one to four heteroatoms. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, triazole, pyrazole, pyridine, pyrazine, pyridazine and pyrimidine, and the like.

Pharmaceutically acceptable salts are known to those of skill in the art. In some of the embodiments described herein, the compounds of formulae (II) and (III) are trifluoroacetate salts.

As used herein, a "protecting group" is a moiety that masks the chemical reactivity of a functional group during one or more reactions. In an illustrative example, a nitrogen protecting group such as tert-butoxycarbonyl (i.e., tert-butyloxycarbonyl, Boc, or BOC) can be introduced at one step to mask the chemical reactivity of a protected nitrogen during one reaction then removed under acidic conditions to allow the formerly protected nitrogen to undergo reaction, e.g., alkylation. A protecting group can be any one known in the at, such as those described in Wuts. P. G. M.; Greene. T. W. Greene's Protective Groups in Organic Synthesis, 4$^{th}$ ed; John Wiley & Sons: Hoboken, N.J., 2007.

Oxygen and nitrogen protecting groups are known to those of skill in the art. Oxygen protecting groups include, but are not limited to, methyl ethers, substituted methyl ethers (e.g., MOM (methoxymethyl ether), MTM (methylthiomethyl ether). BOM (benzyloxymethyl ether), PMBM or MPM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), to name a few), esters (e.g., formate, acetate, benzoate (Bz), trifluoroscetate, dichloroacetate, to name a few), carbonates, cyclic acetals and ketals. Nitrogen protecting groups include, but are not limited to, carbamates (including methyl, ethyl and substituted ethyl carbamates (e.g., Troc), to name a few), amides, cyclic imide derivatives. N-alkyl and N-aryl amine, benzyl amines, substituted benzyl amines, trityl amines, imine derivatives, and enamine derivatives, for example.

In some embodiments, the oxygen protecting group is a base-labile protecting group (i.e., one that can be removed under bask conditions), such as a methyl group when used as an ester to protect a carboxylic acid. In some embodiments the oxygen protecting group is an acid-labile oxygen protecting group (i.e., one that can be removed under acid conditions), such as tert-butyl, 4-methoxybenzyl, or triphenyhmethyl. In some embodiments, the oxygen protecting group is an oxidation-reduction sensitive oxygen protecting group, such as a benzyl ether which is removed under catalytic hydrogenation conditions. In some embodiments the oxygen protecting group is a silyl ether, such as TBDMS, TIPS, or TES, which is removed with nucleophilic fluoride.

In some embodiments, the nitrogen protecting group is a base-labile nitrogen protecting group (i.e., one that is removed under basic conditions), such as 9-fluorenylmethyl carbamate (Fmoc). In some embodiments, the nitrogen protecting group is an acid-labile nitrogen protecting group (i.e., one that is removed under acid conditions), such as triphenylmethyl, tert-butyl, tert-butoxycarbonyl, 2-trimethylsilylethoxycarbonyl (Teoc), or 4-methoxybenzyloxycarbonyl. In some embodiments, the nitrogen protecting group is an oxidation-reduction sensitive nitrogen protecting group, such as a benzyl, which can be removed under catalytic hydrogenation conditions.

Exemplary anions include, but are not limited to, carboxylates (e.g. acetate, benzoate, trifluoroacetate), halides (e.g., chloride, bromide, iodide), sulfate (e.g., monosulfate, bisulfate) and phosphate (e.g. monophosphate, biphosphate).

In some embodiments, alkyl groups and groups comprising an alkyl group (e.g., alkoxy, alkanoyl, alkylamino, aminoalkyl, heteroalkyl) comprise 1-6 carbon atoms. In some embodiments, aryl groups and groups comprising aryl groups (e.g., aroyl) comprise 6-12 carbon atoms. In some embodiments, heteroaryl groups and groups comprising heteroaryl groups (e.g., heteroaroyl) comprise 1-10 carbon atoms and 1-4 heteroatoms selected from oxygen, nitrogen and sulfur.

The term "heterocyclyl" refers to heterocyclic groups, and includes closed ring structures analogous to cycloalkyl groups in which one or more. e.g., 1, 2 or 3, of the carbon atoms in the ring is an element other than carbon, for example, nitrogen, sulfur, or oxygen. Heterocyclic groups may be saturated or unsaturated. The term heterocyclic group includes rings which are attached to the core structure via either a bond to one of the heteroatoms in the ring or a bond to one of the carbons in the ring. Heterocyclyl groups include, for example, piperidine, piperazine, pyrrolidine, morpholine, lactone lactams, and the like.

The term "$C_{3-6}$ heterocyclyl" refers to a heterocyclyl group having three to six carbons in the ring. In an illustrative example, a tetrahydrofuryl has four carbons in the ring in addition to the oxygen, and is thus a $C_4$ heterocyclyl.

As used herein, the term "optionally substituted" refers to optional substitution by one or more substituents selected independently from the group comprising, for example, alkyl, alkoxy, alkylamino, aminoalkyl, hydroxy, halo, cyano, nitro, carboxyl, carboxyalkyl, amido, urea, cycloalkyl, heterocyclyl (e.g., heterocycloalkyl), aryl and heteroaryl substituents.

6.2. Abbreviations

AP=4-aminophenol
AUC=are under the curve
BOC=Boc, tert-butyloxycarbonyl, or tert-butoxycarbonyl
DAP=4-(dimethylamino)phenol
DMF=N, N-dimethylformamide
EDTA=ethylenediaminetetraacetic acid
ESI=electron spray ionization
GC=gas chromatography
HPLC=high performance liquid chromatography
HRMS=high resolution mass spectrometry
KTFA=potassium trifluoroacetate
LOD=loss on drying
NMP=N-methylpyrrolidone
NMR=nuclear magnetic resonance
PMB=para-methoxybenzyl, 4-methoxybenzyl, or MPM
$Pd_2dba_3$=tris(dibenzylideneacetone)dipalladium(0)
TBME=tert-butyl methyl ether, methyl tert-butyl ether, or MTBE
TDAPP=tris(4-(dimethylamino)phenyl) phosphite
THF=tetrahydrofuran
TFA=trifluoroaceticacid

6.3. Methods of Making

In an aspect, provided herein is a method for preparing a compound of formula (II), or a salt thereof comprising the step of admixing. e.g., reacting, a compound of formula (II), or a salt thereof, with a nucleophile (Nuc) in the presence of reagents comprising:
(a) a palladium source; and
(b) a palladium-binding ligand:
to form a compound of formula (II), or a salt thereof.

In an aspect, provided herein is a method for preparing a compound of formula (II), or a salt thereof, (II)

comprising the step of admixing, e.g., reacting, a compound of formula (III), or a salt thereof, (III)

with a nucleophile (Nuc) in the presence of reagents comprising:
(a) a palladium source; and (b) a palladium-binding ligand; to form a compound of formula (II), or a salt thereof, wherein:
Nuc is $R^4$-M, wherein M is H, a metal cation, a non-metal cation, or lone pair of electrons:
$R^4$ is the radical resulting from addition of Nuc:
LG is a leaving group selected from the group consisting of halo or —OC(O)$R_8$, wherein $R_8$ is selected from the group consisting —of $C_{1-6}$-alkyl and haloalkyl:
$R^1$ is selected from the group consisting of Y is selected from the group consisting of:
—$CH_2$—, -continued

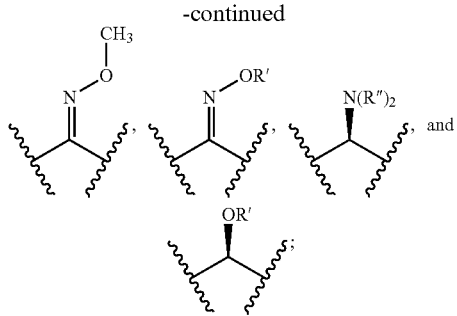

R² is hydrogen or alkoxy;
R³ is selected from the group consisting of hydrogen and an oxygen protecting group;
Z' is selected from the group consisting of hydrogen and an oxygen protecting group;
R' is selected from the group consisting of hydrogen and an oxygen protecting group; and
R'' is selected from the group consisting of hydrogen and a nitrogen protecting group.

In an embodiment, the step of admixing, e.g., reacting a compound of formula (III) in the presence of reagents comprising (a) a palladium source and (b) a palladium-binding ligand forms a palladium pi-allyl intermediate.

In some embodiments, a compound of formula (II) is a compound of formula (IIa).

In some embodiments, a compound of formula (III) is a compound of formula (IIIa).

In another aspect, provided herein is a method for preparing a compound of formula (IIa), or a salt thereof:

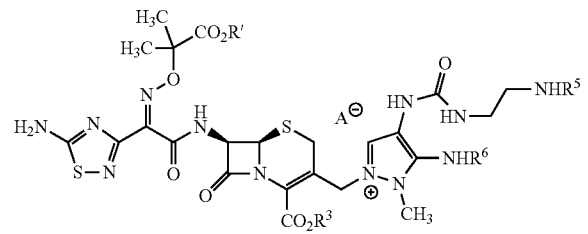

(IIa)

comprising the step of admixing, e.g., reacting, a compound of formula (IIIa), or a salt thereof,

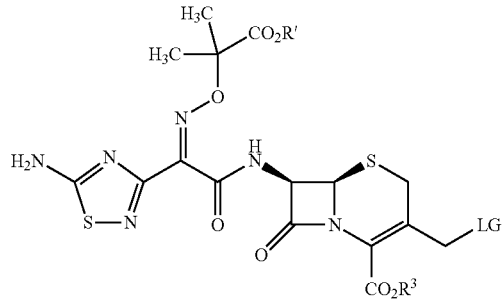

(IIIa)

with the nucleophile (Nuc) having the structure of a compound of formula (X):

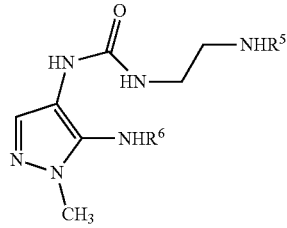

(X)

in the presence of reagents comprising:
(a) a palladium source; and (b) a palladium-binding ligand:
to form a compound of formula (IIa), or a salt thereof wherein
$A^{\ominus}$ is an anion selected from the group consisting of chloride, acetate, trifluoroacetate and bisulfate;
LG is a leaving group selected from the group consisting of halo or —OC(O)R₈, wherein R₈ is selected from the group consisting of $C_{1-6}$-alkyl and haloalkyl:
R³ is an oxygen protecting group,
R' is an oxygen protecting group;
R⁵ is a nitrogen protecting group; and
R⁶ is a nitrogen protecting group.

In an embodiment, the step of admixing. e.g., reacting, a compound of formula (Ia) in the presence of reagents comprising (a) a palladium source and (b) a palladium-binding ligand forms a pi-allyl (i.e., π-allyl) intermediate.

In another embodiment of the method, the reagents further comprise (c) a salt additive. In a further embodiment, the salt additive is selected from the group consisting of a potassium salt, sodium salt, lithium salt, silver salt, and copper salt. In yet a further embodiment, the salt additive is selected from the group consisting of potassium trifluoroacetate, sodium trifuoroacetate, lithium trifluoroacetate, potassium triflate, sodium triflate, lithium triflate, silver triflate and copper sulfate.

In an embodiment, R' is tert-butyl: R is 4-methoxy benzyl ether (i.e., 4-methoxybenzyl); R⁵ is tert-butyloxycarbonyl; and R⁶ is triphenylmethyl.

In an embodiment, LG is halo or —OC(O)R₈, wherein R₈ is selected from the group consisting of $C_{1-6}$-alkyl and haloalkyl. In a further embodiment, LG is chloride or —OC(O)CF₃.

In an embodiment, the palladium source is selected from the group consisting of bis(acetonitrile)dichloropalladium (II), bis(acetylacetonate)palladium(II), bis(benzonitrile)palladium(II) chloride, bis(dibenzylideneacetone)palladium, palladium(II) acetate, palladium(II) trifluoroacetate, palladium(II) chloride, palladium(II) bromide, tetrakis(acetonitrile)palladium(II)tetrafluoroborate, tris(dibenzylideneacetone)dipalladium(0), tris(dibenzylideneacetone)dipalladium (0)-chloroform adduct, [1,2-bis(diphenylphosphino)ethane]dichloropalladium(II), 1,1'-bis(diphenylphosphino)ferrocene-palladium(II)dichloride dichloromethane adduct, bis(tricyclohexylphosphine)palladium(0), bis(triethylphosphine) palladium(II) chloride, bis(triphenylphosphine)palladium (II) acetate, bis(triphenylphosphine)palladium(II) chloride, bis(tri-butylphosphine)palladium(0), bis[1,2-bis(diphenylphosphino)ethane]palladium(0) bis[tri(o-tolyl)phosphine] palladium(II) chloride, dichlorobis(tricyclohexylphosphine) palladium(II), tetrakis(triphenylphosphine)palladium(0), tetrakis(triethylylphosphine)palladium(0), and trans-benzyl(chloro)bis(triphenylphosphine)palladium(II).

In a further embodiment, the palladium source is selected from the group consisting of tris(dibenzylideneacetone)dipalladium(0), tri(dibenzylideneacetone)dipalladium(0)-Chloroform adduct, tetrakis(triphenylphosphine)palladium, palladium(II) acetate, palladium(II) trifluoroacetate, palladium(II) chloride, palladium(II) bromide, and bis(acetonitrile)dichloropalladium(II).

In another embodiment, the palladium source is present in an amount of from about 0.5 mol % to about 5 mole % with respect to the compound of formula (IIIa).

In an embodiment, the palladium-binding ligand is a phosphite ligand of formula (VI):

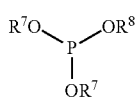

(VI)

wherein
$R^7$ is, at each occurrence, independently selected from phenyl, heteroaryl, heterocyclyl, and $C_{1-6}$ alkyl, wherein said phenyl, heteroaryl heterocyclyl, and $C_{1-6}$ alkyl are optionally substituted with one or more of halo, $C_{1-6}$ alkyl, $C_{1-6}$ alkoxy, or $N(R^9)_2$, and wherein said phenyl and heteroaryl are optionally further substituted with a fused $C_{3-6}$ cycloalkyl or $C_{3-6}$ heterocyclyl;
$R^8$ is selected from phenyl, heteroaryl, heterocyclyl, and $C_{1-6}$ alkyl, wherein said phenyl, heteroaryl, heterocyclyl, and $C_{1-6}$ alkyl are optionally substituted with one or more of halo, $C_{1-6}$ alkyl, $C_1$ alkoxy, or $N(R^9)_2$, and wherein said phenyl and heteroaryl are optionally substituted with a fused $C_{1-6}$ cycloalkyl or $C_{3-6}$ heterocyclyl, or
$R^8$ is

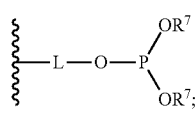

wherein
L is selected from the group consisting of $-(CH_2)_n-$,

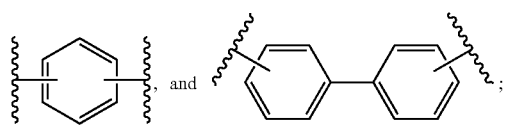

$R^8$ is optionally connected by a bond or $-(CH_2)_n-$ to one $R^7$ to form a ring, or to each $R^7$ to from two rings;
each $R^9$ is $C_{1-6}$ alkyl, or two $R^9$ can combine to form a 3-10 membered heterocyclyl, wherein heterocyclyl comprises 1-3 nitrogen atoms and is optionally substituted by Ca alkyl or $C(O)-C_{1-6}$ alkyl; and
n is 1, 2, or 3.

In another embodiment, the palladium-binding ligand is a phosphite ligand selected from the group consisting of:

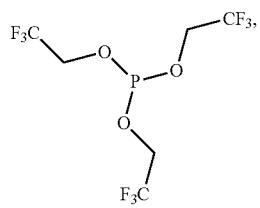

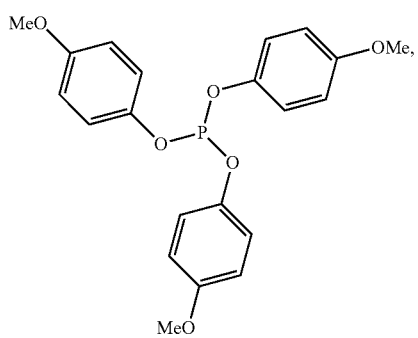

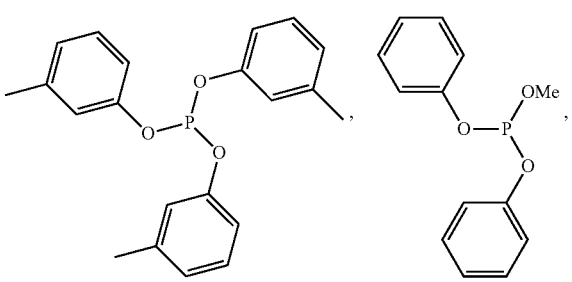

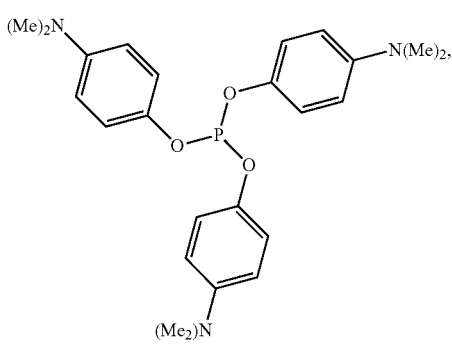

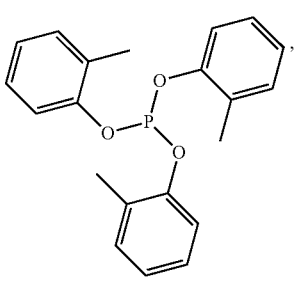

33
-continued
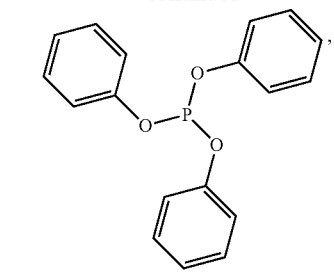
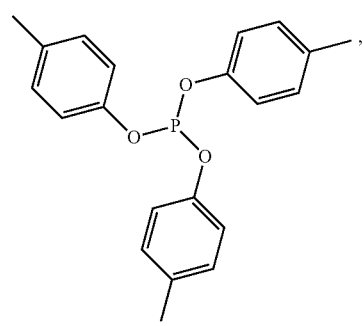
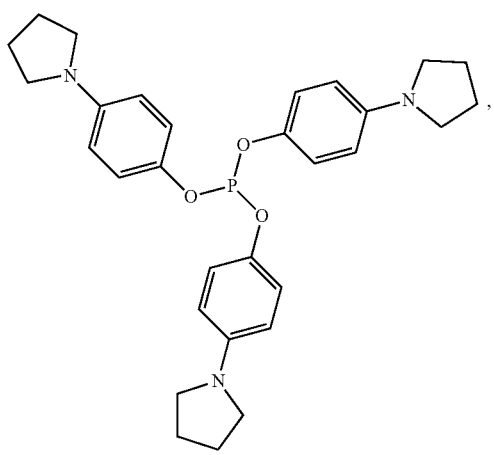
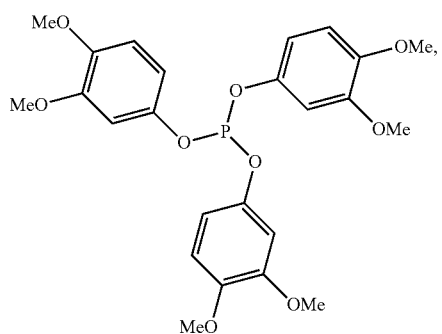
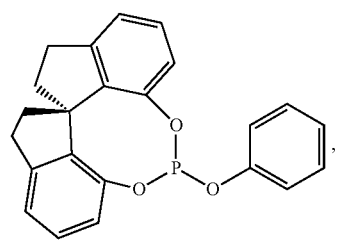
34
-continued
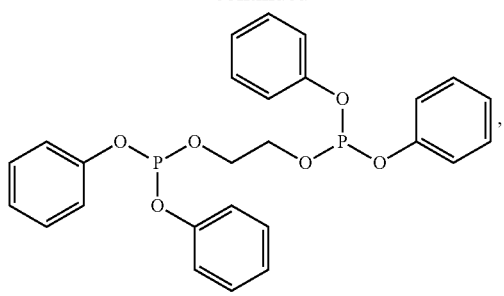
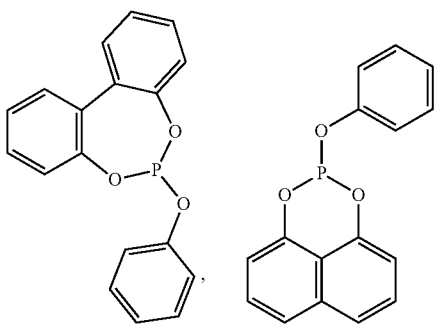
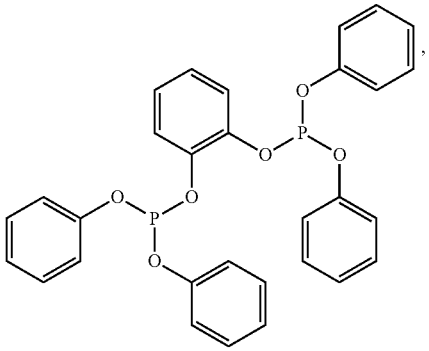
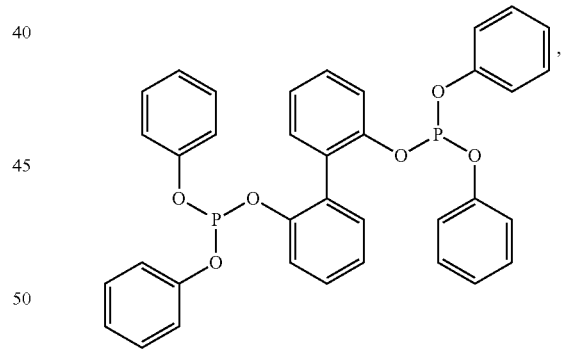
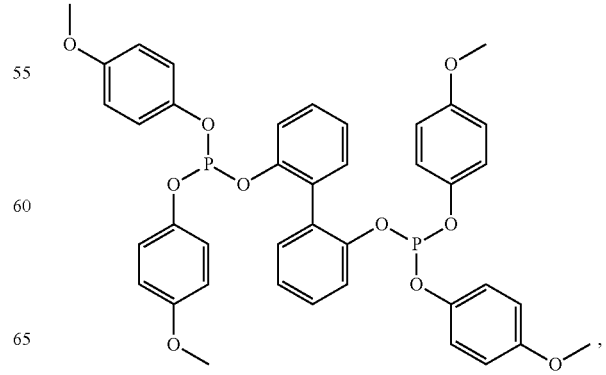

-continued

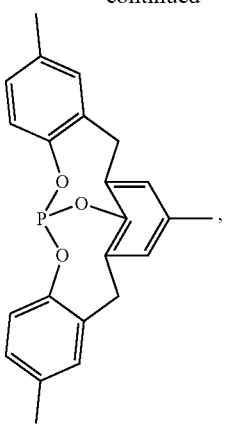

and

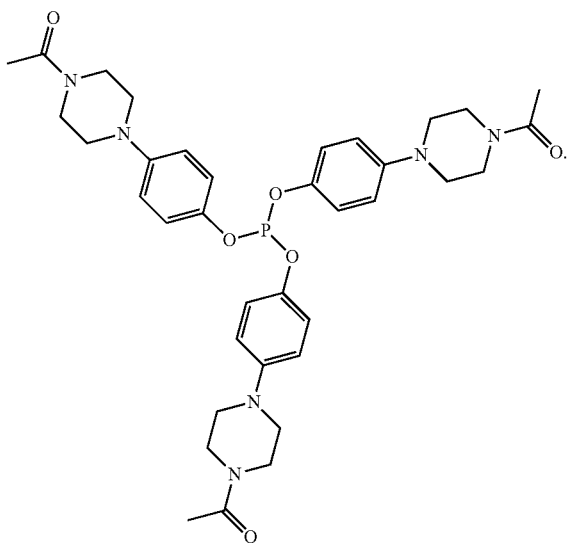 [SMILES: CC(=O)N1CCN(c2ccc(OP(Oc3ccc(N4CCN(C(C)=O)CC4)cc3)Oc3ccc(N4CCN(C(C)=O)CC4)cc3)cc2)CC1]

In an embodiment, the palladium-binding ligand is present in a molar ratio of between about 3:1 and about 10:1 with respect to the palladium source.

In an embodiment, the methods provided herein further comprise the step of admixing, e.g., reacting, the compound of formula (IIa), or a salt thereof, with a strong acid to form a compound of formula (Va):

(Va)

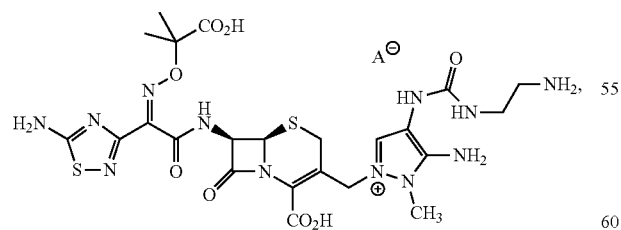

wherein $A^{\ominus}$ is a pharmaceutically acceptable anion. The strong acid can be a Bronsted acid (e.g., trifluoroacetic acid, hydrochloric acid), or a Lewis acid (e.g., $TiCl_4$). In a particular embodiment, the strong acid is trifluoroacetic acid.

In some embodiments, the method comprises the step of isolating the compound of formula (Va). In some embodiments, the step of isolating comprises extracting the admixture with a non-polar solvent, e.g., an aromatic solvent such as toluene, xylenes, or cumene, or a hydrocarbon solvent, such as pentanes, hexanes, or heptanes, or mixtures of one or more thereof. In some embodiments, the extracting the admixture with a non-polar solvent is performed at a temperature in a range of from about −25 to about −5° C. In some embodiments, the step of isolating comprises adding from about 2 to about 6 volumes, e.g., about 2, about 3, about 4, about 5, or about 6 volumes, of a solvent that provides kinetically favorable precipitation conditions. e.g., acetonitrile. In some embodiments, the step of isolating comprises filtering the solids to isolate the compound of formula (Va).

In some embodiments the compound of formula (Va) has the structure of compound (VII):

(VII)

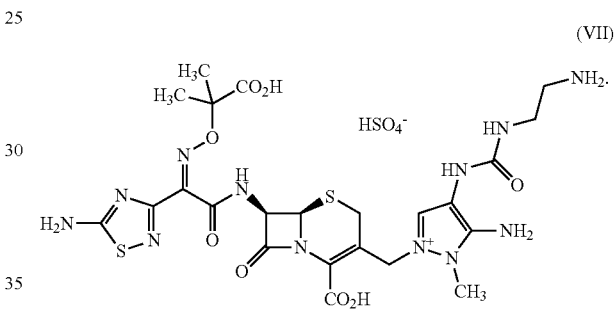

In some embodiments, a compound of formula (II), e.g., a compound of formula (IIa), is a compound of formula (IIb), or a salt thereof.

In some embodiments, a compound of formula (III), e.g., a compound of formula (IIIa), is a compound of formula (IIIb), or a salt thereof.

In some embodiments, a nucleophile (Nuc), e.g., a compound of formula (X), has the structure of the nucleophile (UBT).

In another aspect, provided herein is a method for preparing a compound of formula (IIb), or a salt thereof:

(IIb)

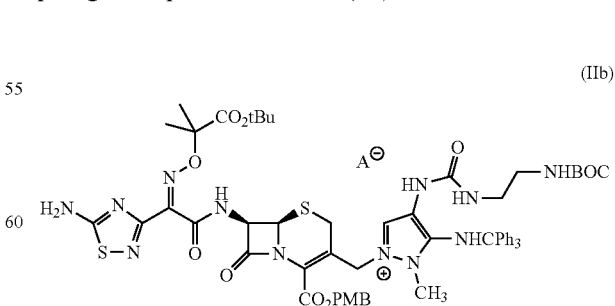

comprising the step of admixing, e.g., reacting, a compound of formula (IIIb), or a salt thereof, (IIIb)

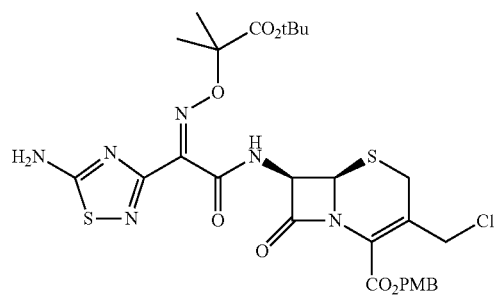

with the nucleophile (UBT):

(UBT)

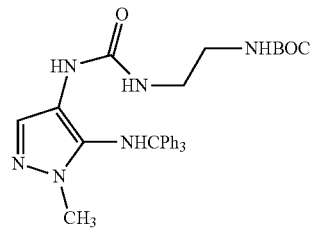

in the presence of reagents comprising:
(a) a palladium source; (b) a palladium-binding ligand; and (c) a salt additive to form a compound of formula (IIb), or a salt thereof, wherein $A^\ominus$ is a pharmaceutically acceptable anion;

the palladium source is selected from the group consisting of tris(dibenzylideneacetone) dipalladium(0), tris(dibenzylideneacetone)dipalladium(0)-chloroform adduct, tetrakis(triphenylphosphine)palladium, palladium(II) acetate, palladium(II) trifluoroacetate, palladium(II) chloride, palladium(II) bromide, and bis(acetonitrile)dichloropalladium(II):

the palladium-binding ligand is selected from the group consisting of

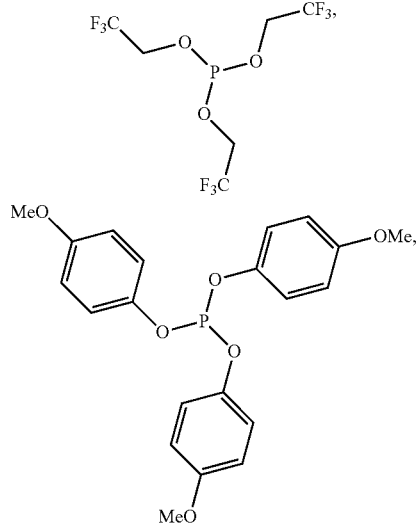

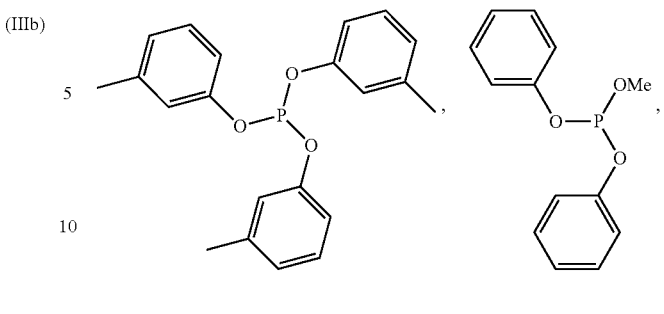

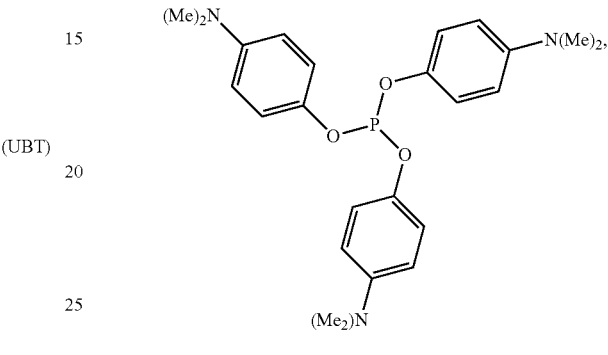

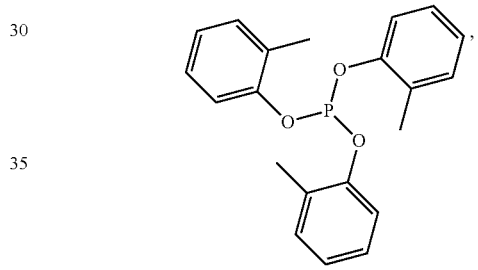

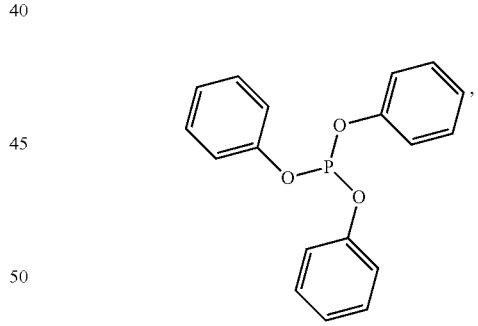

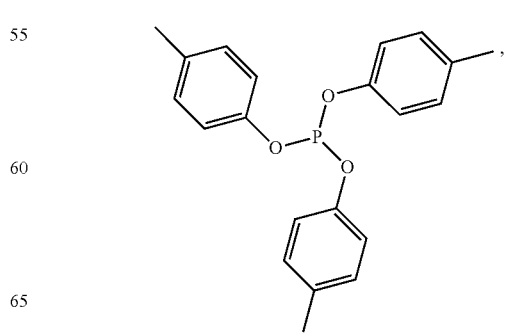

39
-continued
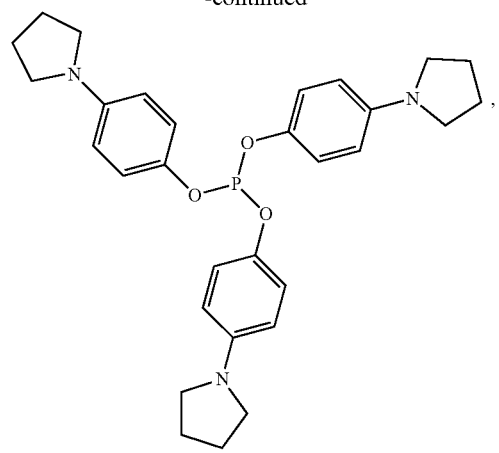
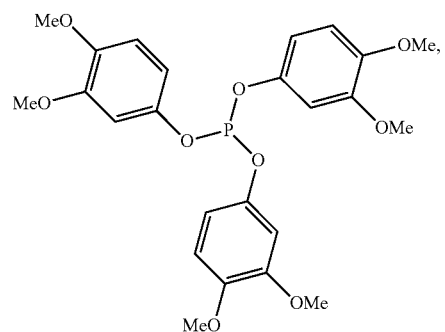
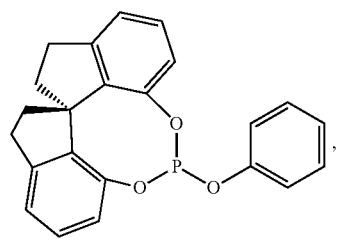
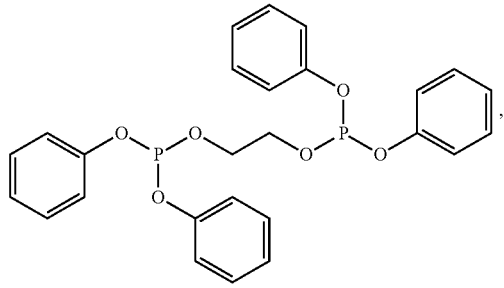
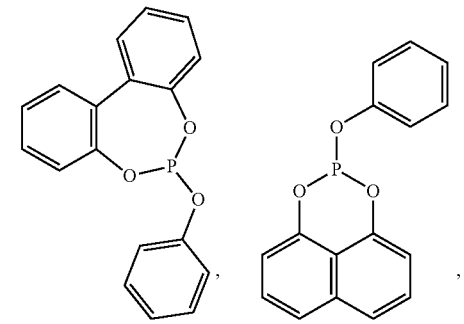
40
-continued
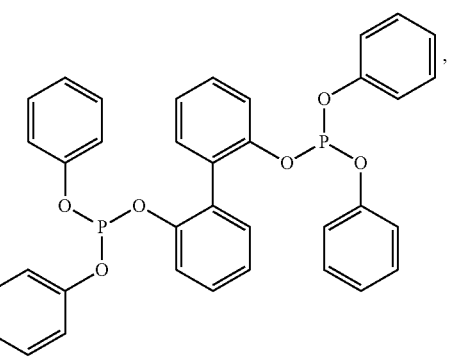
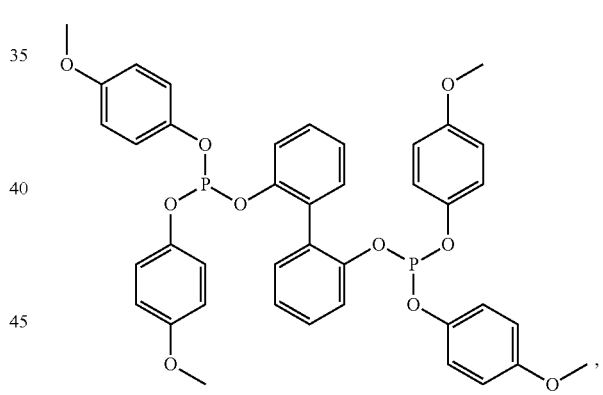
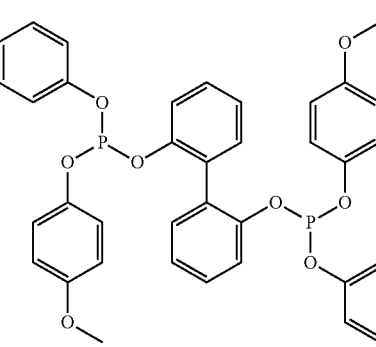
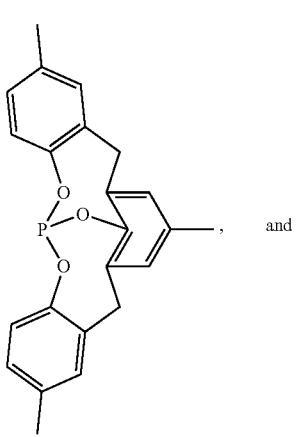, and -continued

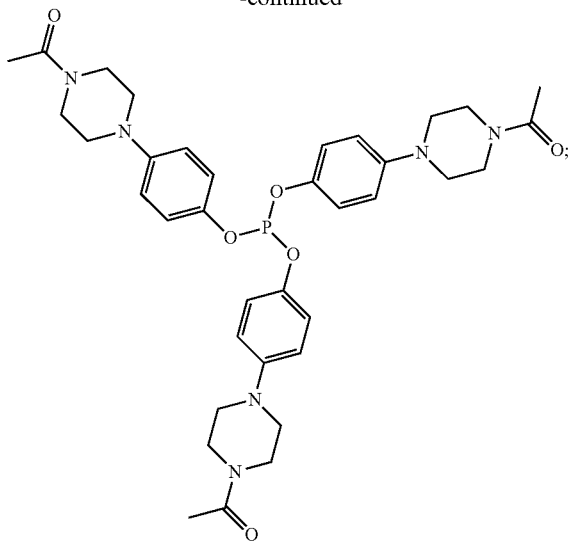

and
the salt additive is selected from the group consisting of potassium trifluoroacetate, sodium trifluoroacetate, lithium trifluoroacetate, potassium triflate, sodium triflate, lithium triflate, silver triflate, and copper sulfate.

In an embodiment, the method further comprises the step of admixing, e.g., reacting, the compound of formula (IIb), or a salt thereof, with a strong acid to form a compound of formula (Va):

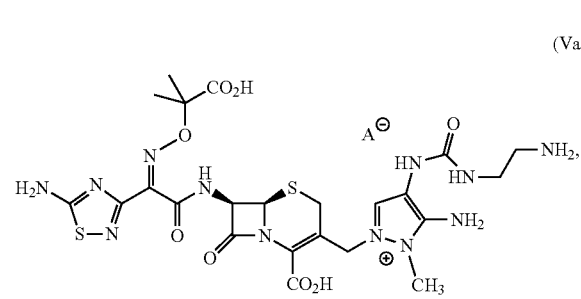

(Va)

wherein $A^\ominus$ is a pharmaceutically acceptable anion.

In certain embodiments of the methods disclosed herein, specific reactants, reagents and/or solvents (e.g., palladium source, palladium-binding ligand, salt additive), and amounts or equivalents, or ranges of amounts or equivalents, are selected from Table 1 and Table 2.

Exemplary methods are disclosed in the Examples.

In another aspect, provided herein is a method for preparing a compound of formula (VIII):

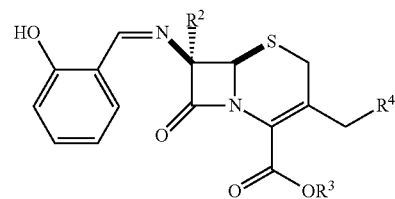

(VIII)

or a salt thereof comprising the step of admixing. e.g., reacting, a compound of formula (IX)

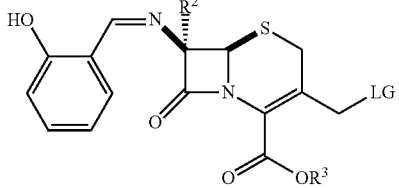

(IX)

or a salt thereof, with a nucleophile (Nuc)(e.g., $R^4$-M) in the presence of reagents comprising:
(a) a palladium source; and (b) a palladium-binding ligand; to form a compound of formula (VI), or a salt thereof.

The nucleophile, palladium source, palladium-binding ligand, and variables of compounds of formulae (VIII) and (IX) are as defined above.

The compound of formula (VIII) can be converted to a compound of formula (II) via methods described in PCT application, PCT/US2014/027706, which is hereby incorporated by reference in its entirety.

In some embodiments, the compound of formula (VIII) is a compound of formula (VIIIa).

In some embodiments, the compound of formula (IX) is a compound of formula (IXa).

In another aspect, provided herein is a method for preparing a compound of formula (VIIIa):

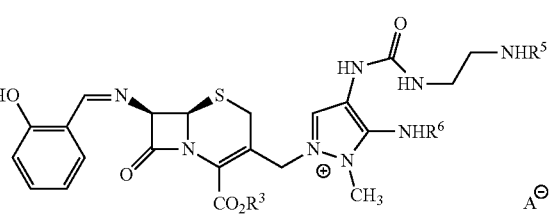

(VIIIa)

or a salt thereof comprising the step of admixing. e.g., reacting, a compound of formula (IXa)

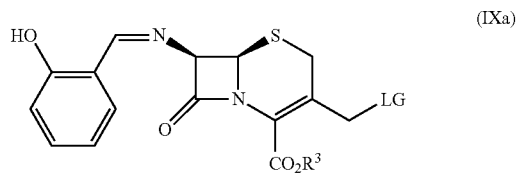

(IXa)

or a salt thereof, with a nucleophile, e.g., a compound of formula (X):

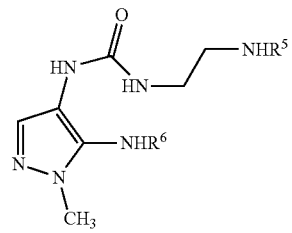

(X)

in the presence of reagents comprising:
(a) a palladium source; and (b) a palladium-binding ligand; to form a compound of formula (VIIa), or a salt thereof, wherein $A^\ominus$ is a pharmaceutically acceptable anion;

LG is halo. —O(C=O)N($R^{18}$)$_2$, —O(C=O)O$R^{18}$ or —OC(O)$R^{18}$, wherein $R^{18}$ is selected from the group consisting of $C_{1-6}$ alkyl and haloalkyl:

$R^3$ is an oxygen protecting group:

$R^5$ is a nitrogen protecting group; and $R^6$ is a nitrogen protecting group.

6.3.1. Solvents

Any organic solvent that does not inhibit the reaction is a suitable solvent. Suitable solvents include, but are not limited to: N-methyl pyrrolidinone, N,N-dimethylformamide. N,N-dimethylacetamide, tetrahydrofuran, methyl tetrahydrofuran, methyl tert-butyl ether, dioxane, acetonitrile, acetone, dichloromethane, propylene carbonate, methanol, ethanol, tert-butanol, tert-amyl alcohol, and any combinations thereof. In some embodiments, the solvent is tetrahydrofuran. In some embodiments, the solvent is a mixture of tetrahydrofuran and N-methyl pyrrolidone.

6.3.2. Temperature

The method for preparing a compound of formula (II), e.g., a compound of formula (IIa), as described herein can be performed at a range of temperatures. In some embodiments, the temperature at which the compound of formula (II), e.g., a compound of formula (IIa), is formed is in a range of from about 0 to about 65° C., such as about 10 to about 40, about 15 to about 35, about 20 to about 30, or about 23 to about 30° C. In some embodiments, the temperature at which the compound of formula (II). e.g., a compound of formula (IIa), is formed is at about 0, about 10, about 20, about 25, about 30, about 40, about 50, or about 60° C. In some embodiments, the temperature is ambient temperature in a range of from about 23 to about 30° C.

6.3.3. Time

The method for preparing a compound of formula (II). e.g., a compound of formula (IIa), as described herein can be performed at various lengths of time. In some embodiments, the reaction time at which the formation of compound of formula (II). e.g., a compound of formula (IIa), is completed is in a range of from about 10 min to about 7 days, such as about 10 min to about 2 days, about 15 min to about 24 hours, about 30 min to about 12 hours, about 1 to about 6 hours, or about 2 to about 5 hours. In some embodiments, the reaction time at which the formation of the compound of formula (II), e.g., a compound of formula (IIa), is completed is at about 0.25, about 0.5, about 1, about 2, about 4, about 6, about 8, about 12, or about 24 hours. In some embodiments, the reaction time is about 15 min. In some embodiments, the reaction time is about 4 hours.

6.3.4. Removal of Palladium

After completion of the reaction, palladium can be removed from the reaction mixture by any method known in the art including but not limited to adsorption, extraction, and crystallization methods. In an illustrative example, the palladium in solution after reaction can be adsorbed onto activated carbon and then the solution filtered through perlite for removal of the palladium from the desired organic product. In another example, the reaction mixture can be treated with a scavenging resin, e.g., a thiourea immobilized on a solid support, e.g., QuadraPure® TU (Johnson Matthey Finland Oy), and then filtered to remove the palladium species.

In some embodiments, following the palladium-mediated coupling, the reaction mixture is subjected to acidic aqueous washes. In some embodiments, the acidic aqueous washes have a pH in the range of from about 0.5 to about 2.5. The washes have the primary purpose of removing palladium from the process stream. This aqueous waste stream contains a significant majority of the palladium used in the process.

In certain embodiments, treatment of the process stream with a dithiocarbamate, e.g., sodium diethyldithiocarbamate or ammonium pyrrolidinedithiocarbamate, is used to provide a compound of the disclosure. e.g., a compound of formula (II)(such as a compound of formula (IIa), a compound of formula (IIb)) or a compound of formula (V)(such as a compound of formula (Va), e.g., ceftolozane sulfate), with palladium levels of 0.001-10 ppm. Typically, the compound of the disclosure. e.g., ceftolazane TFA, contains about 100 ppm palladium. To reduce the palladium levels to pharmaceutically acceptable levels, the compound of the disclosure, e.g., ceftolozane TFA, is first dissolved in an aqueous medium and treated with from about 0.1 to about 10 mole % of a dithiocarbamate, e.g., sodium diethyldithiocarbamate or sodium dimethyldithiocarbamate, resulting in a fine slurry of palladium-containing solids. These palladium-containing solids are filtered away from the batch, which undergoes salt exchange by the previously reported sequence to provide a compound of formula (Va), e.g., ceftolozane sulfate, with 0.001-10 ppm of residual palladium.

In some embodiments the removal of palladium comprises one or more. e.g., two, three, four, or five, methods that are performed in sequence to afford a compound of the disclosure containing a residual amount of palladium. The methods used can be the same method repeated one or more. e.g., two, three, four, or five, times or a combination of different methods. A combination of different methods can be performed in any order. In an illustrative example, an acidic aqueous wash of pH 1 of the organic reaction mixture from the palladium reaction removes about 90% of the palladium used in the reaction. In another illustrative example, an acidic aqueous wash (pH 1), followed by treatment with the dithiocarbamte ammonium pyrrolidinedithiocarbamate (APDTC) and filtration of the precipitated solids through a 0.4 μm filter, affords an organic solution comprising the compound of the disclosure, e.g., a compound of formula (II)(such as a compound of formula (IIa), a compound of formula (IIb)) or a compound of formula (V)(such as a compound of formula (Va)), and <10 ppm palladium.

Subsequent to the methods described herein, a compound of the disclosure, e.g., a compound of formula (II)(such as a compound of formula (IIa), a compound of formula (IIb)) or a compound of formula (V)(such as a compound of formula (Va)), contains a residual level of palladium. In some embodiments, the palladium is present in a range from about 0.01 parts per million (ppm) to about 50 ppm palladium, such as about 0.01 to about 40, about 0.01 to about 30, about 0.01 to about 10, about 0.01 to about 5, about 0.01 to about 3, about 0.01 to about 2, about 0.01 to about 1.5, about 0.01 to about 1, about 0.01 to about 0.5: about 0.02 to about 40, about 0.02 to about 30, about 0.02 to about 10, about 0.02 to about 5, about 0.02 to about 3, about 0.02 to about 2, about 0.02 to about 1.5, about 0.02 to about 1, about 0.02 to about 0.5: about 0.05 to about 40, about 0.05 to about 30, about 0.05 to about 10, about 0.05 to about 5, about 0.05 to about 3, about 0.05 to about 2, about 0.05 to about 1.5, about 0.05 to about 1, about 0.05 to about 0.5; about 0.1 to about 40, about 0.1 to about 30, about 0.1 to about 10, about 0.1 to about 5, about 0.1 to about 3, about 0.1 to about 2, about 0.1 to about 1.5, about 0.1 to about 1, about 0.1 to about 0.5; about 0.2 to about 40, about 0.2 to about 30, about 0.2 to about 10, about 0.2 to about 5, about 0.2 to about 3, about 0.2 to about 2, about 0.2 to about 1.5, about 0.2 to about 1, about 0.2 to about 0.5: about 0.5 to about 40, about 0.5 to about 30, about 0.5 to about 10, about 0.5 to about 5, about 0.5 to about 3, about 0.5 to about 2, or about 0.5 to about 1.5 ppm palladium. In some embodiments the palladium is present in about 0.01, about 0.02, about 0.05, about 0.1, about 0.2, about 0.3, about 0.4, about 0.5, about 1, about 1.5, about 2, about 5, about 10, about 20, or about 50 ppm palladium.

6.3.5. Recovery of Palladium

Palladium is an expensive rare earth metal. Spent . . . crude palladium mixtures recovered from the methods of the disclosure can be sold to metal processors for recycling. Recovery of palladium is desirable to defray the overall cost of a large scale manufacturing process comprising palladium, which involves both the purchase of the palladium catalyst but the cost in disposal of palladium-containing waste streams. In some cases, a palladium recovery method is critical to the economy of the method of the disclosure.

In some embodiments, the palladium is recovered, for recycling and processing after the palladium reaction is completed. In some embodiments, following the palladium-mediated coupling to form a compound of formula (II). e.g., a compound of formula (IIa). e.g., a compound of formula (IIb), the reaction mixture is subjected to acidic aqueous washes in a pH range of from about 0.5 to about 2.5 . . . which have the primary purpose of removing palladium from the process stream. In some embodiments, the pH of the acidic aqueous solution is increased from an initial pH in a range of from about 0.5 to about 5.5 to a final pH in a range of from about 5 to about 10. In some embodiments, an oxidant, e.g., bleach, is added. The recovery process results in the precipitation of solid palladium-containing solids, which can be filtered away from the solution.

In an example, the combined acidic aqueous layers (pH range of 0.5 to 2.5) are distilled (jacket temperature=40° C.) until about 10% of the volume is removed (the removed solvent being mostly THF). The solution is treated with NH$_4$OH until the pH is from about 5 to about 10 (target pH of about 7.5), while keeping the temperature below 20° C. This results in a dark slurry containing white solids. Following, the batch is treated with 0.4 equivalents (relative to the TATD-CLE input of the batch) of NaClO (i.e., bleach; 0.1-2 equivalents, with a target of about 0.4 equivalents relative to the TATD-CLE input). The solution immediately turns red and is stirred for 2 hours at room temperature. Then, cellulose is added to the batch and the slurry is filtered through a pad of cellulose, providing a palladium-rich cake. About 90% of the palladium initially present in the aqueous solutions is recovered, or about 80% of the palladium initially used in the process.

6.4. Compositions

In an aspect, provided herein are compositions comprising a compound of formula (Va).

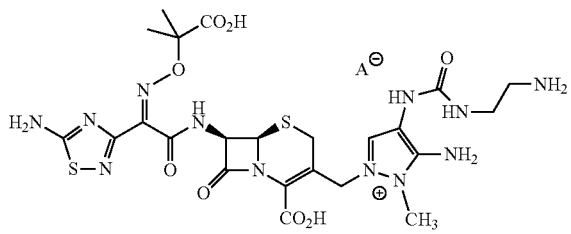

(Va)

wherein $A^\ominus$ is a pharmaceutically acceptable anion, prepared according to any of the methods described herein. In some embodiments. $A^\ominus$ is chloride, bromide, iodide, sulfate, toluenesulfonate, methanesulfonate, edisylate, maleate, phosphate, ketoglutarate . . . trifluoroacetate, or trifluoromethanesulfonate. In some preferred embodiments, $A^\ominus$ is sulfate.

In some embodiments, the compound of formula (Va) has the structure of compound (VII):

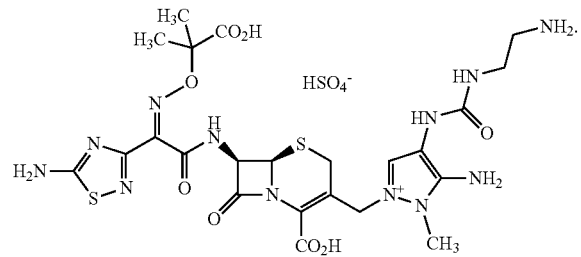

(VII)

In an aspect, provided herein are compositions comprising a compound of formula (Vb),

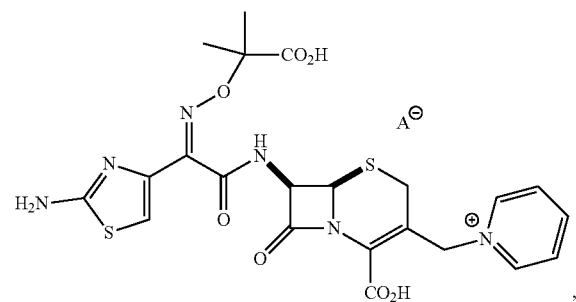

(Vb)

wherein $A^\ominus$ is a pharmaceutically acceptable anion, prepared according to any of the methods described herein.

In some embodiments the composition (e.g., comprising a compound of formula (Va) or a compound of formula (Vb)) comprises palladium. In some embodiments, the palladium is present in a range from about 0.01 parts per million (ppm) to about 50 ppm palladium . . . such as about 0.01 to about 40, about 0.01 to about 30, about 0.01 to about 10, about 0.01 to about 5, about 0.01 to about 3, about 0.01 to about 2, about 0.01 to about 1.5, about 0.01 to abot 1, about 0.01 to about 0.5: about 0.02 to about 40, about 0.02 to about 30, about 0.02 to about 10 . . . about 0.02 to about 5, about 0.02 to about 3, about 0.02 to about 2, about 0.02 to about 1.5, about 0.02 to about 1, about 0.02 to about 0.5: about 0.05 to about 40, about 0.05 to about 30, about 0.05 to about 10, about 0.05 to about 5, about 0.05 to about 3, about 0.05 to about 2, about 0.05 to about 1.5, about 0.05 to about 1, about 0.05 to about 0.5: about 0.1 to about 40, about 0.1 to about 30 . . . about 0.1 to about 10, about 0.1 to about 5, about 0.1 to about 3, about 0.1 to about 2, about 0.1 to about 1.5, about 0.1 to about 1, about 0.1 to about 0.5: about 0.2 to about 40, about 0.2 to about 30, about 0.2 to about 10, about 0.2 to about 5, about 0.2 to about 3, about 0.2 to about 2, about 0.2 to about 1.5, about 0.2 to about 1, about 0.2 to about 0.5; about 0.5 to about 40, about 0.5 to about 30, about 0.5 to about 10, about 0.5 to about 5, about 0.5 to about 3, about 0.5 to about 2, or about 0.5 to about 1.5 ppm palladium. In some embodiments, the palladium is present in about 0.01, about 0.02, about 0.05, about 0.1, about 0.2, about 0.3, about 0.4, about 0.5, about 1, about 1.5, about 2, about 5, about 10, about 20, or about 50 ppm palladium. In some preferred embodiments, the level of palladium in the composition is less than the pharmaceutically acceptable level of palladium, e.g., as specified in the United States Pharmacopeia (USP) General Chapter <232> Elemental Impurities—Limits. Revision Bulletin dated Feb. 1, 2013:

TABLE A

Elemental Impurities for Drug Products (excerpted from USP Chapter <232> Revision Bulletin dated Feb. 1, 2013)

| Element | Oral Daily Dose PDE[a] (µg/day) | Parenteral Daily Dose PDE (µg/day) | Inhalational Daily Dose PDE (µg/day) | LVP[b] Component Limit (µg/g) |
|---|---|---|---|---|
| Palladium | 100 | 10 | 1.5 | 1.0 |

[a]PDE = Permissible daily exposure based on a 50-kg person.
[b]LVP = Large volume parenteral.

TABLE B

Default Concentration Limits for Drug Substances and Excipients (excerpted from USP Chapter <232> Revision Bulletin dated Feb. 1, 2013)

| Element | Concentration Limits (µg/g) for Oral Drug Products with a Maximum Daily Dose of ≤ 10 g/day | Concentration Limits (µg/g) for Parenteral Drug Products with a Maximum Daily Dose of ≤ 10 g/day | Concentration Limits (µg/g) for Inhalation Drug Products with a Maximum Daily Dose of ≤ 10 g/day |
|---|---|---|---|
| Palladium | 10 | 1.0 | 0.15 |

In some embodiments, the level of palladium is determined in any one of the pharmaceutical compositions described herein. For example, the level of palladium can be measured when the composition is formulated in unit dosage form. e.g., in combination with tazobactam, e.g., in Zerbaxa®.

In another aspect, provided herein is a composition comprising:

(a) a compound of formula (IIIb):

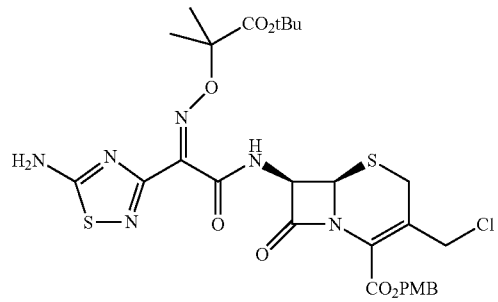

(IIIb)

or a salt thereof, (b) the nucleophile of formula (UBT):

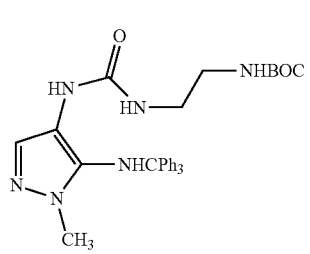

(UBT)

(c) a palladium source;
(d) a palladium-binding ligand; and
(e) a salt additive.

In an embodiment, the palladium source is selected from the group consisting of tris(dibenzylideneacetone)dipalladium(0), tris(dibenzylideneacetone)dipalladium(0)-chloroform adduct, tetrakis(triphenylphosphine)palladium, palladium(II) acetate, palladium(II) trifluoroacetate, palladium (II) chloride, palladium(II) bromide, and bis(acetonitrile)dichloropalladium(II).

In an embodiment, the palladium-binding ligand is selected from the group consisting of

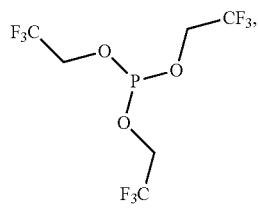

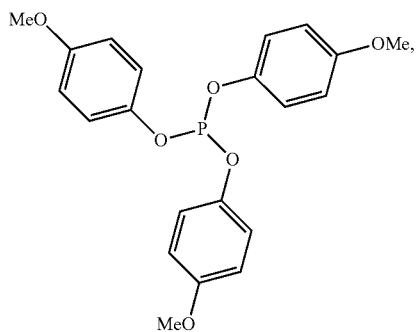

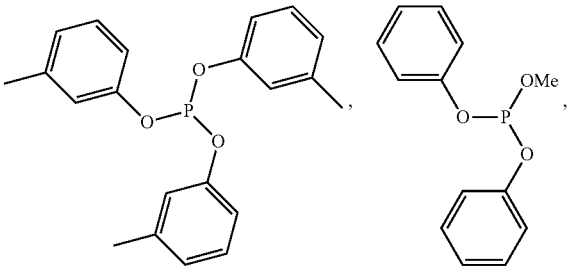

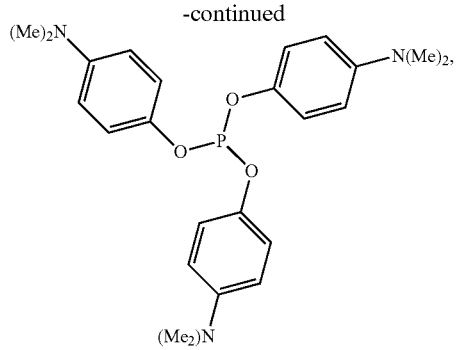
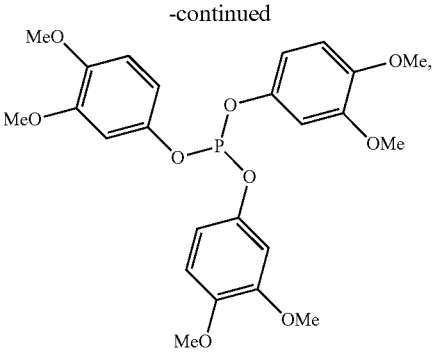
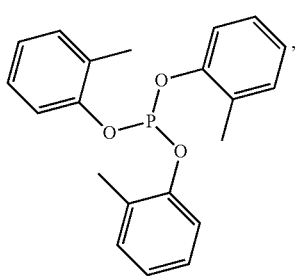
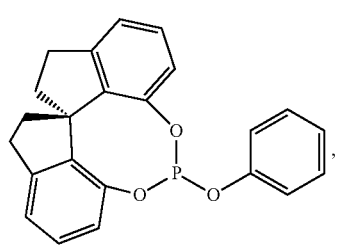
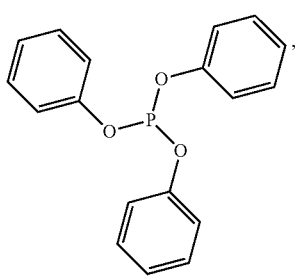
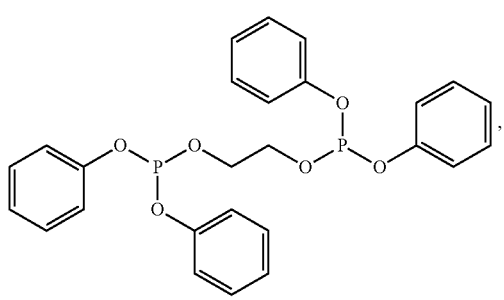
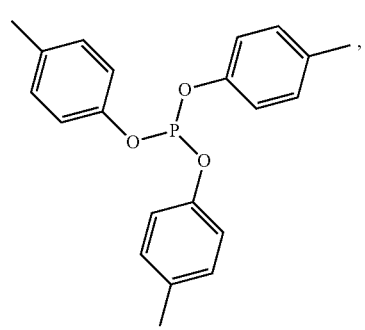
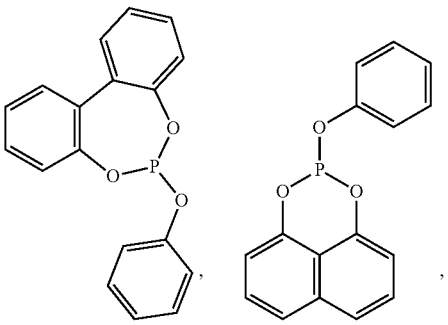
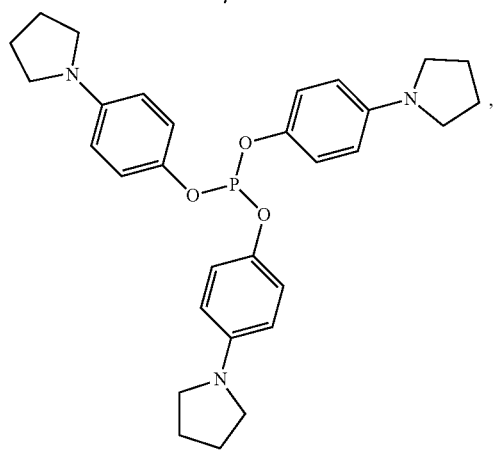
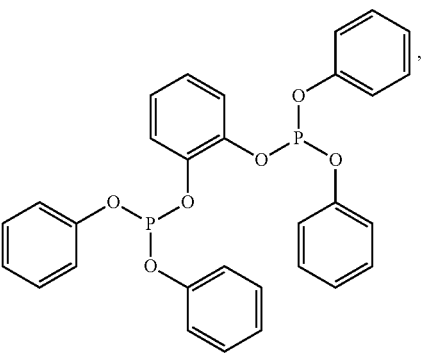

-continued

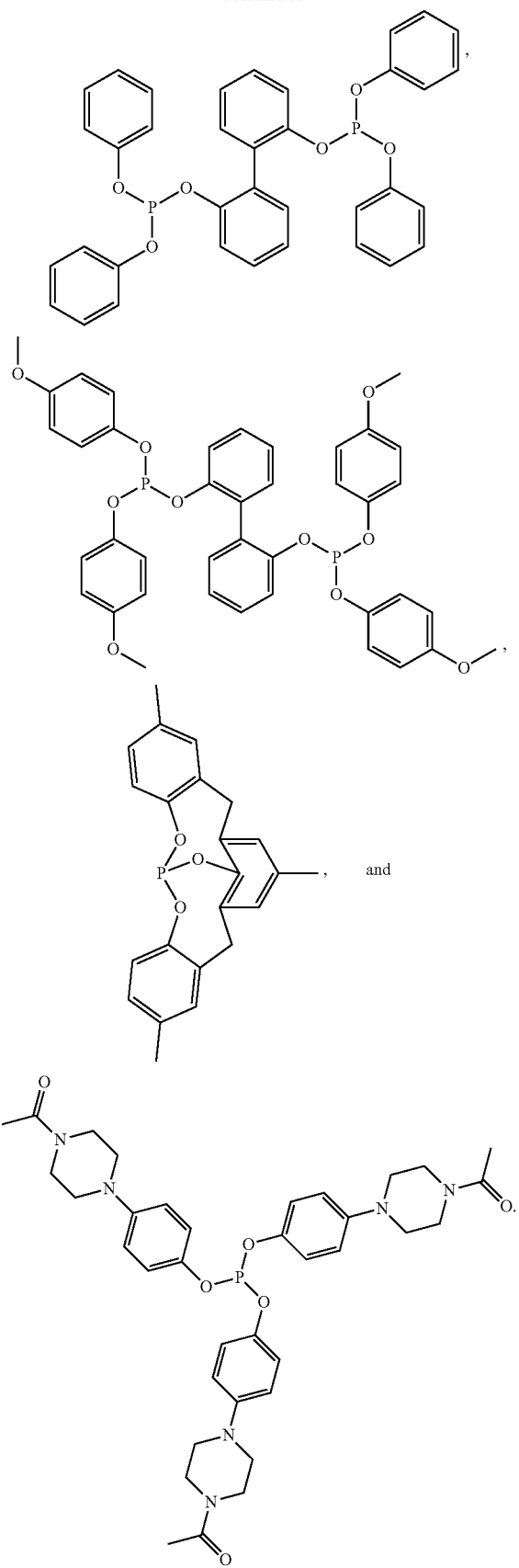

In an embodiment the salt additive is selected from the group consisting of potassium trifluoroacetate, sodium trifluoroacetate, lithium trifluoroacetate, potassium triflate, sodium triflate, lithium triflate, silver triflate, and copper sulfate.

In another embodiment, the composition further comprises a pi-allyl intermediate.

In another embodiment, the composition further comprises a compound of formula (IIb):

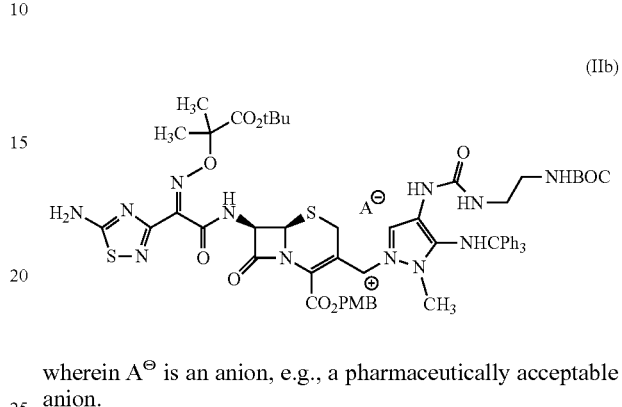

(IIb)

wherein $A^\ominus$ is an anion, e.g., a pharmaceutically acceptable anion.

In another embodiment, the salt additive is selected from the group consisting of potassium trifluoroacetate, sodium trifluoroacetate, and lithium trifluoroacetate, and the composition further comprises a compound of formula (IIIc).

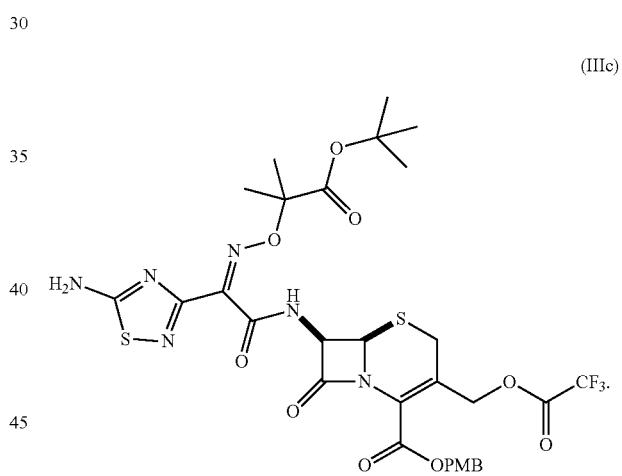

(IIIc)

6.4.1. Pharmaceutical Compositions

A compound as prepared by the method of the disclosure. e.g., a compound of formula (Va). e.g., compound (VI), can be formulated as a pharmaceutical composition. The pharmaceutical composition can optionally further include a beta-lactamase inhibitor such as tazobactam. The pharmaceutical composition can be obtained by processes described herein. In particular, pharmaceutical compositions can be obtained by a process comprising the step of forming an aqueous solution containing the compound of the disclosure. e.g., a compound of formula (Va), and lyophilizing the aqueous solution to obtain a pharmaceutical composition. The aqueous solution may additionally comprise excipients, stabilizers, pH adjusting additives (e.g., buffers) and the like. Non-limiting examples of these additives include sodium chloride, citric acid and L-arginine. For example, the use of sodium chloride can result in greater stability; L-arginine can be used to adjust pH and to increase the solubility of ceftolozane; and citric acid can be used to prevent discoloration of the product, due to its ability to chelate metal ions. In particular, the aqueous solution can include ceftolozane sulfate and additional components such as sodium chloride to stabilize the ceftolozane, and an alkalizing agent such as L-arginine to provide a pH of about 5-7 prior to lyophilization. The pharmaceutical compositions can be lyophilized (freeze-dried) and stored as a lyophilate for later reconstitution. Exemplary disclosures relating to lyophilization of pharmaceutical formulations include Konan et al., Int. J. Pharm. 2002 233 (1-2), 293-52; Quintanar-Guerrero et al., J. Microencapsulation 1998 15 (1), 107-119; Johnson et al., J. Pharmaceutical Sci. 2002, 91 (4), 914-922; and Tang et al., Pharmaceutical Res. 2004, 21 (4), 191-200; the disclosures of which are incorporated herein by reference. As an alternative to lyophilization, a pharmaceutical composition can be spray dried, or stored frozen and then thawed, reconstituted, and diluted before administration.

In some embodiments, the pharmaceutical composition of the disclosure. e.g., comprising a compound of formula (Va), e.g., compound (VII), is formulated as a pharmaceutically acceptable salt. The term "pharmaceutically acceptable salt" refers to the relatively non-toxic, inorganic and organic acid addition salts of a compound of formula (Va), e.g., compound (VII). These salts can be prepared in situ during the final isolation and purification of the compound, or by separately admixing. e.g., reacting, a purified compound in its free base form with a suitable organic or inorganic acid, and isolating the salt thus formed. Representative salts include the bromide, chloride, sulfate, bisulfate, phosphate, nitrate, acetate, valerate, oleate, palmitate, stearate, laurate, benzoate, lactate, phosphate, tosylate, citrate, maleate fumarate, succinate, tartrate, naphthylate, mesylate, glucoheptonate, lactobionate, laurylsulfonate salts, and amino acid salts, and the like. See, for example. Berge et al. 1977. "Pharmaceutical Salts," J. Pharm. Sci. 66: 1-19.

Pharmaceutical compositions of the cephalosporin compounds of the disclosure, e.g., a compound of formula (Va), e.g., compound (VII), can be prepared for storage as lyophilized formulations or aqueous solutions by admixing the pharmaceutically active ingredient having the desired degree of purity with optional pharmaceutically acceptable carriers, excipients or stabilizers typically employed in the art (all of which are referred to herein as "carriers"). i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980).

In some embodiments, buffering agents in amounts ranging from about 2 mM to about 50 mM are used to help to maintain the pH in the range that approximates physiological conditions. Suitable buffering agents for use with the present disclosure include both organic and inorganic acids and salts thereof, such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium gluconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

In some embodiments preservatives are added in amounts ranging from 0.01%-1% (w/v). Suitable preservatives for use with the present disclosure include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol.

In some embodiments, isotonifiers sometimes known as "stabilizers" added to ensure isotonicity of liquid compositions of the present disclosure and include polhydric sugar alcohols, for example trihydric or higher sugar alcohols, such as glycerin, erythritol, arabitol, xylitol sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine lysine, glycine, glutamine, asparagine, histidine, alanine, ornithine, L-leucine, 2-phenylalanine glutamic acid, threonine, etc., organic sugars or sugar alcohols, such as lactose, trehalose, stachyose, mannitol, sorbitol, xylitol ribitol, myoinisitol, galactitol, glycerol and the like, including cyclitols such as inositol; polyethylene glycol; amino acid polymers; sulfur containing reducing agents, such as thiourea, glutathione, thioctic acid, sodium thioglycolate, thioglycerol, α-monothioglycerol and sodium thiosulfate; low molecular weight polypeptides (e.g., peptides of 10 residues or fewer): proteins such as human serum albumin bovine serum albumin, gelatin or immunoglobulins: hydrophilic polymers, such as polyvinylpyrrolidone monosaccharides, such as xylose, mannose, fructose, glucose; disaccharides such as lactose, maltose, sucrose and trisaccacharides such as raffinose; and polysaccharides such as dextran. In some embodiments, stabilizers are present in the range from 0.1 to 10,000 weights per part of weight of pharmaceutically active ingredient.

The compositions will usually be supplied as part of a sterile, pharmaceutical composition that will normally include a pharmaceutically acceptable carrier. This composition can be in any suitable form (depending upon the desired method of administration). For example, the pharmaceutical composition can be formulated as an aqueous solution and administered by intravenous injection or intravenous infusion.

Pharmaceutical compositions can include a ceftolozane salt, e.g., compound (VII), obtained by methods described herein, combined with a beta-lactamase inhibitor, such as tazobactam (CAS #: 89786-04-9), avibactam (CAS #1192500-31-4), sulbactam (CAS #68373-14-8) and/or clavulanic acid (CAS #58001-44-8). The beta-lactamase inhibitor can be included in a crystalline or amorphous form, such as a lyophilized tazobacam or crystalline tazobactam (e.g., U.S. Pat. Nos. 8,476,425 and 5,763,603) to obtain the pharmaceutical composition.

Pharmaceutical compositions comprising a compound of formula (Va), e.g., compound (VII), can be formulated to treat infections by parenteral administration (including subcutaneous, intramuscular, and intravenous) administration. In one particular embodiment, the pharmaceutical compositions described herein are formulated for administration by intravenous injection or infusion. Pharmaceutical antibiotic compositions can include ceftolozane sulfate and stabilizing amount of sodium chloride (e.g., 125 to 500 mg of sodium chloride per 1,000 mg ceftolozane active) in a lyophilized unit dosage form (e.g., powder in a vial). The unit dosage form can be dissolved with a pharmaceutically acceptable carrier, and then intravenously administered. In another aspect, pharmaceutical antibiotic compositions can include ceftolozane sulfate obtained by a process comprising the steps of lyophilizing an aqueous solution containing ceftolozane and a stabilizing amount of sodium chloride, where the stabilizing amount of sodium chloride is about 125 to 500 mg of sodium chloride per 1.000 mg ceftolozane active in the aqueous solution prior to lyophilization.

6.5. Methods of Treatment

In one aspect, provided herein is a method for the treatment of bacterial infections in a mammal, comprising administering to said mammal a therapeutically effective amount of a pharmaceutical composition comprising a compound of formula (Va), e.g., compound (VII), prepared according to one or more of the methods described herein. A method for the treatment of bacterial infections in a mammal can comprise administering to said mammal a therapeutically effective amount of a pharmaceutical composition comprising ceftolozane sulfate and sodium chloride.

As used herein, a "mammal" can be any mammal such as a mouse, a rat, a dog, a cat, a horse, a pig, a cow, or a primate, such as a human. In certain embodiments the mammal is a human. The mammal can be an adult or a juvenile.

The pharmaceutical composition of a compound of formula (Va). e.g., compound (VII), can used in combination with metronidazole for the treatment of complicated intra-abdominal infections caused by the following Gram-negative and Gram-positive microorganisms such as: *Escherichia coli* (including strains producing CTX-M-14/15 ESBLs), *Klebsiella pneumoniae* (including strains producing CTX-M-15 ESBLs). *Pseudomonas aeruginosa, Enterobacter clocae, Kebsiella oxytoca, Proteus mirabilis, Bacteroides fragilis, Bacteroides ovatus, Bacteroides thetaiotaomicron, Bacteroides vulgatus, Streptococcus anginosus. Streptococcus constellatus*, and *Streptococcus salivarius*.

The pharmaceutical compositions can used for the treatment of complicated urinary tract infections, including pyelonephritis, with or without concurrent bacteremia, caused by the following Gram-negative microorganisms: *Escherichia coli* (including strains resistant to levofloxacin and/or producing CTX-M-14/15 ESBLs), *Klebsiella pneumoniae* (including strains resistant to levofloxacin and/or producing CTX-M-15 ESBLs), *Proteus mirabilis*, and *Pseudomonas aeruginosa*.

The recommended dosage regimen of pharmaceutical compositions comprising a compound of formula (Va). e.g., compound (VII), prepared by one or more methods disclosed herein, and tazobactam in an amount providing 1 g of ceftolozane active per 500 mg of tazobactam acid, is 1.5 g administered every 8 hors by intravenous (IV) infusion over 1 hour in patients ≥18 years of age. The duration of therapy should be guided by the severity and site of infection and the patient's clinical and bacteriological progress (e.g., every 8 hours for 4-14 days for complicated Intra-Abdominal Infections and 7 days for Complicated Urinary Tract Infections, including Pyelonephritis).

7. EXAMPLES

Examples have been set forth below for the purpose of illustration and to describe certain specific embodiments of the invention. However, the scope of the claim is not to be in any way limited by the examples set forth herein. Various changes and modifications to the disclosed embodiments will be apparent to those skilled in the art and such changes and modifications may be made without departing from the spirit of the invention and the scope of the claims.

7.1. Example 1: Coupling of TATD-CLE and UBT Via Palladium Catalysis

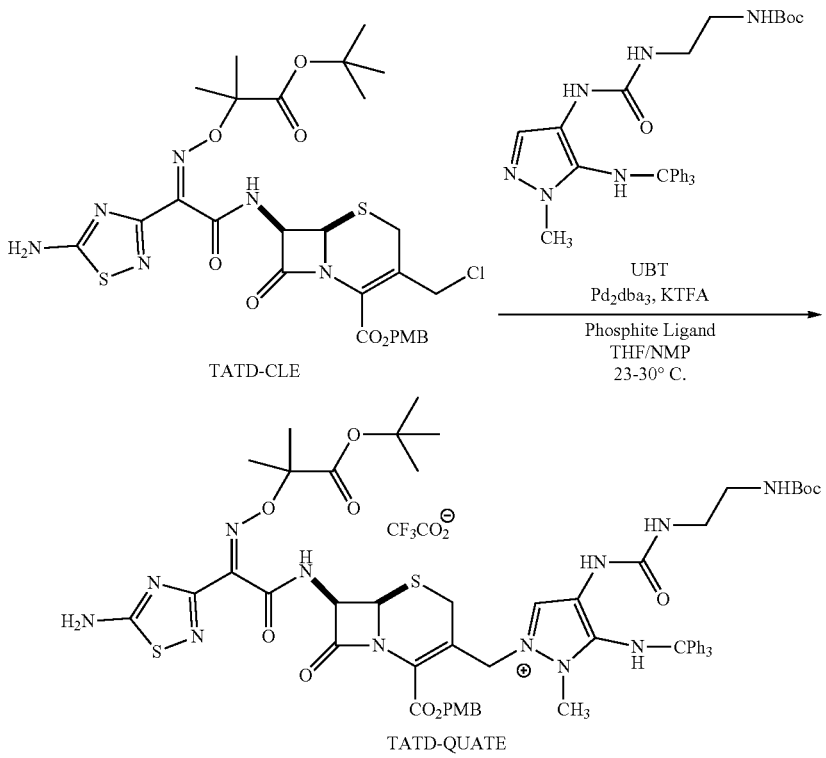

TATD-CLE (compound 3. FIG. 1A) (5 g gross, 92.3% potency, 4.615 g active, 6.775 mmol). UBT (compound 4. FIGS. 1A and 1B) (4.029 g, 7.453 mmol), and potassium trifluoroacetate (2.061 g, 13.55 mmol) were charged to the reaction vessel. THF (39.23 mL) was then added, forming an opaque, white suspension. The reaction mixture was stirred for 30 minutes at 30° C., remaining a white suspension. Tri(4-(dimethylamino)phenyl) phosphite (238 mg, 0.542 mmol) was added, followed by addition of Pd$_2$dba$_3$ (62 mg, 0.068 mmol). The reaction vessel was evacuated and back-filled with N$_2$ gas twice, allowing the solvent to boil in the process. Upon stirring, the reaction mixture turned dark purple and then light greenish yellow, indicating the presence of active catalyst. The reaction progress was monitored by HPLC sampling every hour. A typical reaction time at this catalyst loading is about 3.5 to 4 hours, as defined by less than 2% remaining of TATD-CLE and/or TATD-TFA with respect to TATD-QUATE.

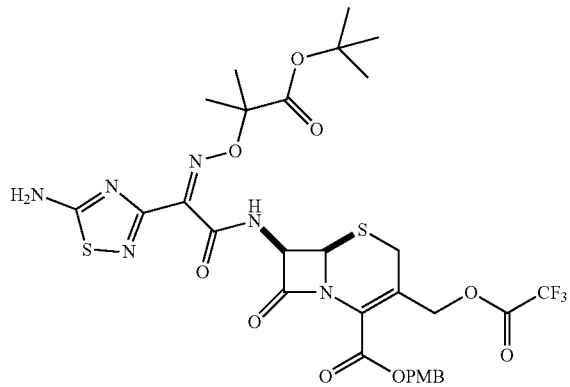

(IIIc)

7.2. Example 2: Coupling of SCLE and UBT Via Palladium Catalysis

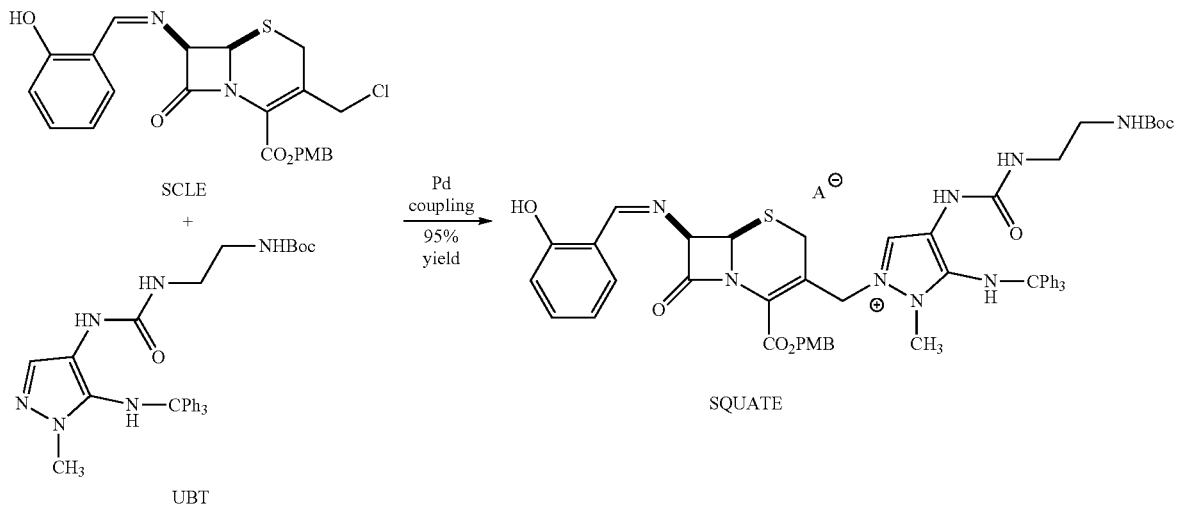

The yield of TATD-QUATE by the process described above was about 92-96%. The yield of TATD-QUATE by the process shown in FIG. 1A (compound 5a) was about 63-66%.

In the example above, a transient intermediate of formula (IIIc)(also referred to herein as "TATD-TFA") was formed. More specifically, TATD-CLE was partially converted to TATD-TFA. However, both TATD-CLE and TATD-TFA were converted to TATD-QUATE.

SQUATE was formed under coupling conditions similar to those described in Example 1.

7.3. Example 3: Screening of Catalysts

Several metal complexes were screened for use in the disclosed method. Metal complexes that do not perform well in the disclosed method include Fe$_2$(CO)$_9$, Rh(PPh$_3$)$_3$Cl, NiCl$_2$(PPh$_3$)$_2$, CuSO$_4$, AgOTf, Ni(acac)$_2$, Pt(PPh$_3$)$_2$ (H$_2$CCH$_2$), Ru$_4$(C$_{10}$H$_{15}$)$_4$Cl$_4$, and Ir$_2$(cod)$_4$C$_2$.

7.4. Example 4: Synthesis of tris(4-(dimethylamino)phenyl) phosphite (TDAPP), a palladium-binding ligand

Step 1: Preparation of 4-(dimethylamino)phenol (DAP)

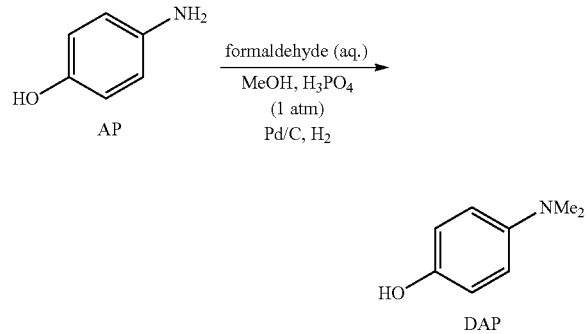

Step 2: Preparation of tris(4-(dimethylamino)phenyl) phosphite (TDAPP)

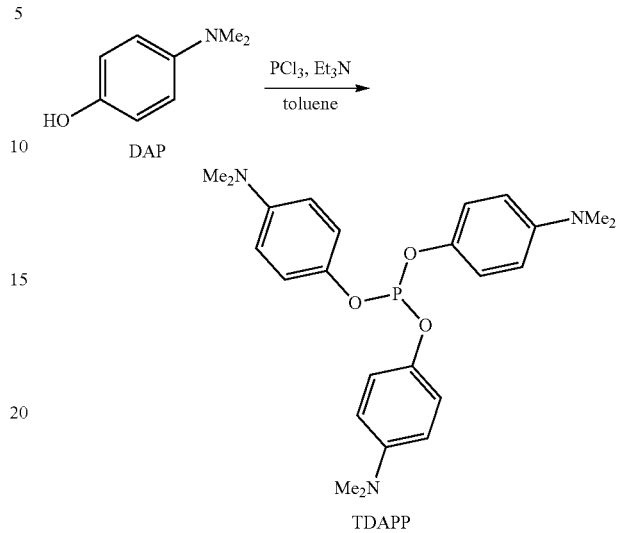

4-aminophenol (21.8 g, 200 mmol, 1.0 equiv) was charged to a 1 L 3-neck round bottom flask and the temperature was adjusted to 20° C. (about 15 to 20° C.). Methanol (218 mL, 10 vol.) was charged to the flask and agitated for 15 mm, at about 22° C. (about 20 to 25° C.). The 4-aminophenol did not fully dissolve in the MeOH, resulting in a suspension. $H_3PO_4$ (85%, 2.3 g, 20 mmol, 0.10 equiv) was slowly charged while maintaining the batch temperature at <25° C. The batch temperature was adjusted to about 12° C. (10 to 15° C.); then formaldehyde (36-38% aqueous solution, 45.9 mL, 300 mmol, 3.0 equiv) was charged slowly while keeping the batch temperature <20° C. The batch was agitated for 30 min at about 22° C. (20 to 25° C.) resulting in a clear, light yellow solution.

The solvent was then degassed with nitrogen and the reactor was filled with nitrogen. Pd/C (10% on activated carbon, 4.4 g, 0.2 wt. equiv) was charged to the batch. The batch was agitated vigorously under 1 atm hydrogen pressure using a balloon at 20 to 25° C. for three hours. An aliquot of the reaction mixture (10 μL) was withdrawn for HPLC analysis. When the amount of aminophenol (AP) was ≤2% with respect to DAP, the reaction is deemed complete. The reaction usually takes 3-5 hours, but can be stirred overnight at 20 to 25° C. without observation of degradation.

The reaction mixture was filtered through a pad of celite (21.8 g, 1.0 wt. equiv). The celite pad was washed with methanol (43.2 mL, 2 vol). The batch was concentrated to 4 volumes (86.2 mL) by distillation. Toluene (174.4 mL, 8 vol) was charged followed by the addition of water (130.8 mL, 6 vol). Aqueous 10NaOH (3 mL, 30 mmol, 0.15 equiv) was then slowly charged, and the batch was agitated for 30 min. The phases were separated and the upper organic phase was concentrated under vacuum to 6 volumes (130.8 mL). Toluene (86.4 mL, 4 vol) was charged and the batch was concentrated to 8 volumes (174.4 mL) by distillation. An aliquot of the reaction mixture (10 μL) was withdrawn for analysis of the level of methanol and water.

$Et_3N$ (39.03 mL, 280 mmol, 1.40 equiv) was charged to the reaction mixture obtained in step 1. The batch temperature was adjusted to 2° C. (0 to 5° C.). A solution of $PCl_3$ (7.00 mL, 80 mmol, 0.40 equiv) in toluene (43.2 mL, 2 vol) was slowly charged to the reactor while maintaining the reaction temperature <12° C. The reaction is exothermic and the mixture becomes thick. Vigorous stirring was required for efficient mixing. The batch was agitated for 30 minutes at 15° C. (10 to 20° C.). An aliquot of the reaction was withdrawn for HPLC analysis. The reaction is deemed complete when the amount of DAP is ≤2% with respect to TDAPP. TBME (174.4 ml, 8 vol) was charged and the batch was agitated for 2 hours at 23° C. (20 to 25° C.) to ensure thorough precipitation of the $Et_3N.HCl$ from the solution.

The batch was filtered through a pad of celite (21.8 g, 1 wt. equiv)/silica gel (10.8 g, 0.5 wt. equiv). The pad of celite/silica gel was washed with TBME (43.2 ml, 2 vol). Precipitation of white crystals ($Et_3N.HCl$ salt) may form in the filtrate. If precipitation occurs, the filtrate should be filtered through a pad of celite/silica gel.

The batch was concentrated under reduced pressure to 3 volumes (65.4 mL) at 43° C. (40 to 45° C.), 2-Methyl-2-butanol (174.4 mL, 8 vol) was charged to the batch. A precipitate may form during addition of the alcohol. The batch was then concentrated undereduced pressure to 6 vol (130.8 mL). Next, 2-methyl-2-butanol (43.2 mL, 2 vol) was charged to the batch. A thick slurry is formed after 2-methyl-2-butanol addition. An aliquot of the batch was removed to determine residual toluene content by GC-FID. The toluene content may affect the following crystallization.

The batch temperature was adjusted to 63° C. (60 to 65° C.), resulting in a clear solution. The batch temperature was then adjusted to 40-45° C. and seeded with TDAPP seed crystals (200 mg). Following, the batch was cooled to 20-25° C. and agitated for 2 hours. The batch was filtered and the wet cake was washed with cold 2-methyl-2-butanol (43.2 mL, 2 vol). The batch was dried under reduced pressure to obtain TDAPP as a white solid. A sample was removed to monitor the drying by GC. The batch is deemed dry when the amount of 2-methyl-2-butanol is ≤5,000 ppm.

The overall yield for Steps 1 and 2 was 17.5 g (60% of theoretical), isolated as a white to light yellow solid. The overall purity was 97.8% AUC (by HPLC analysis) and the structure was confirmed by $^1$H NMR.

7.5. Example 5: Preparation of Ceftolozane TFA from TATD-CLE

7.5.1. Preparation of TATD-QUATE

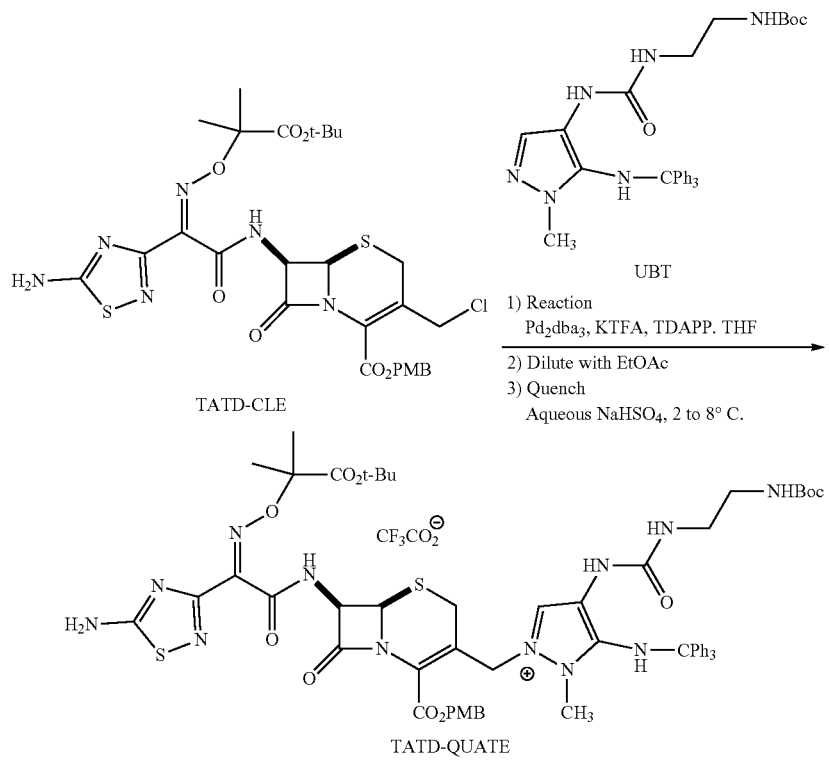

7.5.1(a) Equipment

Two 1 L jacketed glass bottom-drain reactors and an internal temperature probe were used.

7.5.1(b) Material Chares and Reaction Parameters for the Preparation of TATD-QUATE

TABLE 1

Materials used during the preparation of TATD-QUATE

| Process Step | Material | MW (g/mol) | Equivalents or volumes | Amount Used |
|---|---|---|---|---|
| 1 | THF | 72.11 | 7.0 vol | 420.0 mL |
| 2 | UBT | 540.66 | 1.1 mol equiv | 52.4 g |
| 2 | TATD-CLE* | 681.18 | 1.0 mol equiv | 66.6 g |
| 2 | KTFA | 152.11 | 1.5 mol equiv | 20.1 g |
| 2 | TDAPP | 439.49 | 0.08 vol | 3.10 g |
| 3 | THF | 72.11 | 0.5 vol | 30.0 mL |
| 5 | Pd$_2$dba$_3$ | 915.70 | 0.01 mol equiv | 0.81 g |
| 6 | THF | 72.11 | 1.0 vol | 60.0 mL |
| 10 | EtOAc | 88.11 | 6.0 vol | 360.0 mL |
| 11 | Water | 18.02 | 14.0 vol | 600.0 mL |
| 11 | NaHSO$_4$ | 120.06 | 0.5 wt. equiv | 42.0 g |
| 18 | Harborlite 800 | 114.02 | 0.08 wt. equiv | 4.8 g |
| 19 | EtOAc | 88.11 | 0.5 vol | 30.0 mL |

*TATD-CLE active amount of 60.0 grams (90.1% potency) was used for all volume and molar equivalent calculations.

7.5.1(c) Stepwise Process for the Preparation of TATD-QUATE

1. Charge THF [tetrahydrofuran] (373.5 g, 420.0 mL, 7.0 volumes) at 15 to 25° C. to reactor 1.
2. Charge UBT (52.4 g, 9.99 mmol, 1.1 equiv), TATD-CLE (66.6 g, 88.1 mmol, 1.0 equiv). KTFA [potassium trifluoroacetate](20.1 g, 132.1 mmol, 1.5 equiv) and TDAPP [tris(4-(dimethylamino)phenyl)phosphite] (3.10 g, 7.0 mmol, 0.08 equiv) to reactor 1.
3. Charge THF [tetrahydrofuran](26.7 g, 30.0 mL, 0.5 volumes) to reactor 1 by spray ball.
4. Adjust the batch temperature to 30° C. and agitate the batch for 30 minutes.
5. Charge TDAPP [tris(4-(dimethylamino)phenyl)phosphite] (3.10 g, 7.0 mmol, 0.06 equiv) followed by Pd$_2$dba$_3$ [tris(dibenzylideneacetone)dipalladium(0)] (0.81 g, 0.9 mmol, 0.01 equiv) to the batch.
6. Charge THF [tetrahydrofuran](53.4 g, 60.0 mL, 1.0 volume) to reactor 1 by spray ball and stir the batch at 30° C.
7. Collect a sample after 4 hours and analyze it for reaction completion. The reaction is deemed complete when ≤2.0% of TATD-CLE+TATD-TFA remain with respect to TATD-QUATE.
8. If >2.0% of TATD-CLE+TATD-TFA remains with respect to TATD-QUATE, then the batch should be stirred for an additional 0.5 to one hour and repeat Step 7.

7.5.1(d) Stepwise Procedure for Quench and Aqeuous Work-Up of TATD-QUATE

9. Cool the batch in reactor 1 to 5 to 15° C.
10. Charge EtOAc [ethyl acetate](322.9 g, 360.0 mL, 6.0 volumes) to the batch in reactor 1, while maintaining the batch temperature at 2 to 15° C. then cool to 2 to 8° C.

11. Prepare an aqueous solution of 5.0% (w/v) sodium bisulfate [NaHSO$_4$] in reactor 2 by first dissolving (21.0 g) NaHSO$_4$ in water (420.0 mL, 7.0 volumes) and adjust the solution temperature of 2 to 8° C.
12. Charge the batch in reactor 1 to the 5% NaHSO$_4$ solution prepared in Step 11 and stir the batch for 25 to 35 minutes, while maintaining the batch temperature at 2 to 8° C. through Step 18.
13. Discontinue stirring and allow the phases to separate for at least 20 minutes.
14. Separate the lower aqueous layer and transfer it to a holding tank for disposal.
15. Prepare an aqueous solution of 5.0% (w/v) sodium bisulfate [NaHSO$_4$] in reactor 1 by first dissolving (21.0 g) NaHSO$_4$ in water (420.0 mL, 7.0 volumes) and adjust the solution temperature to 2 to 8° C.
16. Charge the aqueous solution in reactor 1 (step 15) to the batch in reactor 2 and stir the batch for 25 to 35 minutes.
17. Discontinue stirring and allow the phases to separate for 20 to 40 minutes.
18. Separate the lower aqueous layer and transfer it to a holding tank for disposal.
19. Filter the organic layer through Harborlite 800 (4.8 g, 0.08 wt. equivalents) or equivalent filtration material to remove palladium (0).
20. Wash the Harborite with EtOAc (26.9 g, 30.0 mL, 0.5 volumes) and combine organic layers in reactor 2.

7.5.2. Preparation and Isolation of Ceftolozane TFA 7.5.2(a) Material Charges and Reaction Parameters for the Preparation of Ceftolozane TFA (Ceftolozane Trifluoroacetate)

TABLE 2

Materials used during the preparation of ceftolozane TFA crude

| Process Step | Material | MW (g/mol) | Molar equivalents or volumes | Amount Used |
|---|---|---|---|---|
| 22 | Anisole | 108.14 | 1.5 vol | 90.0 mL |
| 25 | CF$_3$CO$_2$H | 136.01 | 4.5 vol | 270.0 mL |
| 29 | Toluene | 92.14 | 10.0 vol | 600.0 mL |
| 33 | ACN | 41.05 | 1.5 vol | 75.0 mL |
| 34 | MTBE | 88.15 | 10.0 vol | 600.0 mL |
| 36, 37 | MTBE | 88.15 | 5.0 vol | 300.0 mL |

7.5.2(b) Stepwise Process for the Preparation of Ceftolozane TFA

21. Reduce the volume of the batch in reactor 2 by vacuum distillation to 4.0 volumes (240.0 mL), while maintaining the batch temperature at <20° C. during distillation.
22. Charge anisole (89.6 g, 90.0 mL, 1.5 volumes) to reactor 2.
23. Reduce the batch volume in reactor 2 by vacuum distillation to 3.5 volumes (210.0 mL), while maintaining the batch temperature at <20° C.
24. Cool the batch to <10° C.
25. Charge CF$_3$CO$_2$H (402.0 g, 240.0 mL, 4.5 volumes) slowly, while maintaining the batch temperature at <20° C.

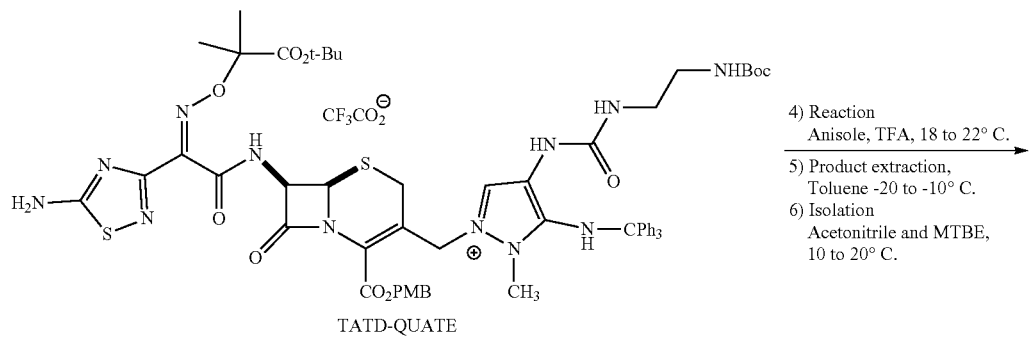

TATD-QUATE

4) Reaction
   Anisole, TFA, 18 to 22° C.
5) Product extraction,
   Toluene -20 to -10° C.
6) Isolation
   Acetonitrile and MTBE,
   10 to 20° C.

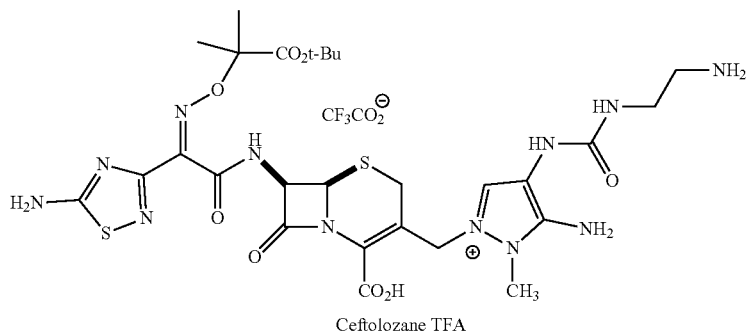

Ceftolozane TFA t-Bu: t-butyl
Boc: t-butyloxycarbonyl
PMB: para-methoxybenzyl

Figure 3:
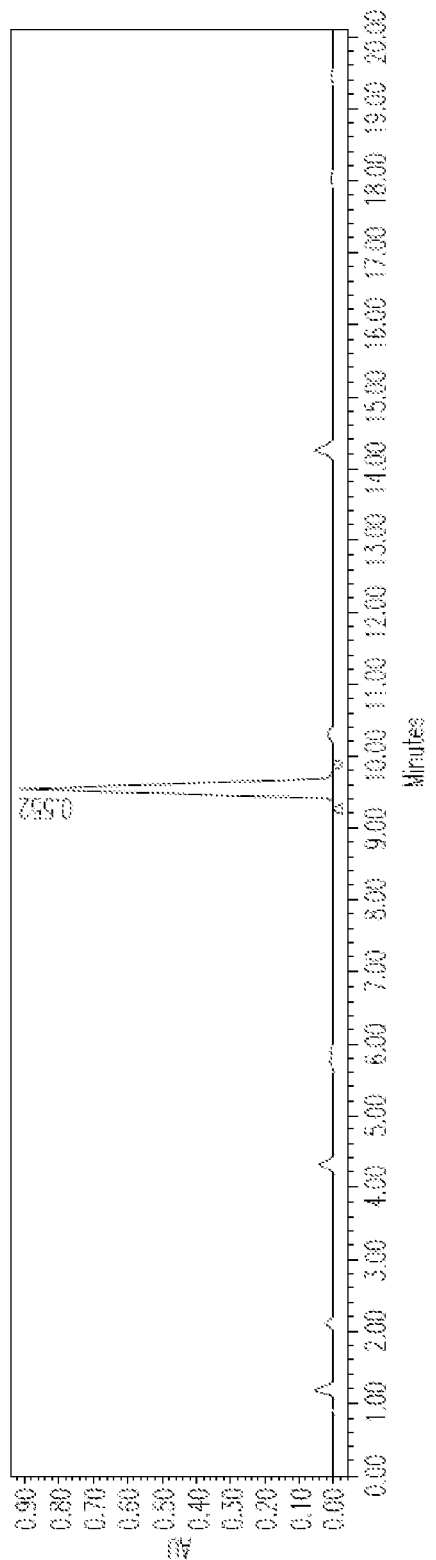
FIG. 3 is an HPLC chromatograph of compound 3z. A major peak at 9.552 min is shown.

26. Stir the batch at 18 to 22° C. for 4 to 10 hours. The temperature should be continuously monitored. A recommended monitoring interval is 1 hour.
27. Collect a sample after 4 hours and analyze it for reaction completion. The reaction is deemed complete when ≤2.0% of Ceftolozane t-butyl ester remains with respect to Ceftolozane (see, e.g., FIG. 3).
28. If ceftolozane t-butyl ester is >2.0%, continue the reaction for 0.5 to 1 hour and repeat Step 27.
29. Charge toluene (522.0 g, 600.0 mL, 10.0 volumes) to reactor 2 and adjust the batch temperature to −15° C.
30. Stir the mixture for 30 to 40 minutes at −15° C.
31. Discontinue stirring and allow the phases to separate for at least 20 minutes.
32. Collect the viscous lower phase in reactor 1.
33. Charge ACN [acetonitrile](71.1 g, 90.0 mL, 1.5 volumes) to reactor 1 and adjust the batch temperature to 10 to 20° C.
34. Charge MTBE [methyl t-butyl ether](444.2 g, 600.0 mL, 10.0 volumes) to reactor 1 over 30 to 60 minutes (10-20 vol/h), while maintaining the batch temperature at 15° C.
35. Stir the resulting slurry for 2 to 4 hours at 15° C.
36. Filter the slurry and wash the cake with MTBE (111.1 g, 150.0 mL, 2.5 volumes).
37. Wash the cake a second time with MTBE (111.1 g, 150.1 mL, 2.5 volumes).
38. Dry the cake under reduced pressure with a flow of nitrogen. The drying process is deemed complete when the final LOD [loss on drying] value is ≤19%. Typically, the batch is dry with a final LOD of 7.0 to 9.0%.

As used herein, "t-butyl ceftolozane," "t-butyl ceftolozane ester," or "t-buty ceftolozane" refer to a compound of formula (INT-Va):

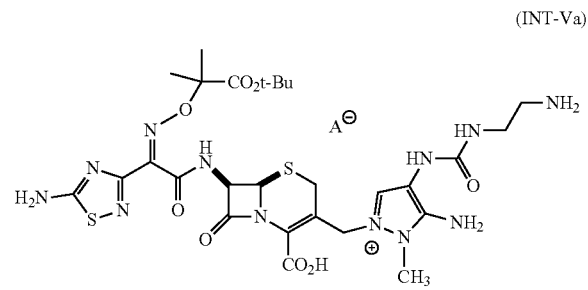

(INT-Va)

wherein $A^{\ominus}$ is a pharmaceutically acceptable anion.

Perhaps owing to the significant increase in yield realized in the palladium-mediated coupling reaction, previously developed methods of isolating ceftolozane TFA did not provide an isolable solid.

To improve the isolation, two operations in the process were improved following the TFA-mediated deprotection reaction. The first was the low temperature phase separation; the second was the precipitation of ceftolozane TFA.

Product Extraction—Low Temperature Phase Separation

A low temperature phase separation that can be used to isolate ceftolozane TFA consists of diluting the deprotection reaction mixture with dichloromethane and cooling the batch to −40 to −25° C. This protocol results in a biphasic mixture, where the lower, ceftolozane-rich phase is separated (based on solvent density; measured using a mass flow meter) and carried forward in the process. When this protocol was applied to the process stream following the palladium mediated coupling significant product losses were realized (10-20% on average) due to the distribution of ceftolozane TFA into the upper layer of the biphasic mixture.

To circumvent this issue, a new protocol was developed, as follows. Upon completion of the TFA-mediated deprotection reaction, the batch is diluted with 8-14 volumes of toluene (target of 10 volumes). The resulting biphasic mixture is then cooled to a temperature in the range of from about −25 to about −5° C., resulting in a biphasic mixture with a phase separation that is easily visualized (i.e., no flow meter is required to monitor the separation). The lower, ceftolozane-rich phase is easily separated from the upper layer, resulting in a significant upgrade in purity of the process stream. In addition, very little yield loss occurs during this operation, with <1% of the ceftolozane TFA remaining in the upper layer, which is discarded. In addition to toluene, other non-polar solvents are acceptable, such as hydrocarbon solvents (e.g., pentanes, hexanes heptanes), other aromatic solvents (e.g. xylenes, cumene), and mixtures of one or more thereof.

Isolation—Precipitation of Ceftolozane TFA

When trying to precipitate solid ceftolozane TFA following the palladium-mediated coupling using known methods, a typical result is the formation of a gel-like substance that could not be filtered or isolated in a usable fashion. This may be attributed to the propensity of ceftolozane TFA to agglomerate under the isolation conditions, or the poor stability of the ceftolozane TFA solution during isolation.

These issues are addressed in two ways. First, additional acetonitrile (solvent) is added to the batch prior to the precipitation event. This is counterintuitive in that adding additional solvent would not typically improve a precipitation, as the additional solvent would solubilize the material to be isolated. However, in this case, additional acetonitrile stabilizes the ceftolozane TFA solution during precipitation, contributing to an orderly and controlled precipitation. Without wishing to be bound by theory, the addition of acetonitrile is believed to provide a solvent mixture exhibiting kinetically favorable conditions for precipitation. Preferably, from about 2 to about 6 volumes of acetonitrile present during the precipitation ensure the formation of filterable solids. Since volumes of solvent are typically determined relative to the limiting reagent (in this case. TATD-CLE as shown in Table 1), for each 100 g of limiting reagent, about 200 to about 600 mL acetonitrile is preferably used for this purpose.

The second protocol change to the isolation is the lowering of the isolation temperature to from about 0 to about 15° C. Subsequent to the lowering of the solution temperature, an antisolvent, such as a hydrocarbon or ethereal antisolvent, e.g., methyl tert-butyl ether, is added to precipitate the desired product. The decrease in temperature, together with the additional acetonitrile noted above, combines to provide a controlled and orderly precipitation of highly-filterable solids, without the formation of gel-like materials, thus maximizing the isolated yield of ceftolozane TFA upon filtration.

7.5.3. Notes

Figure 4:
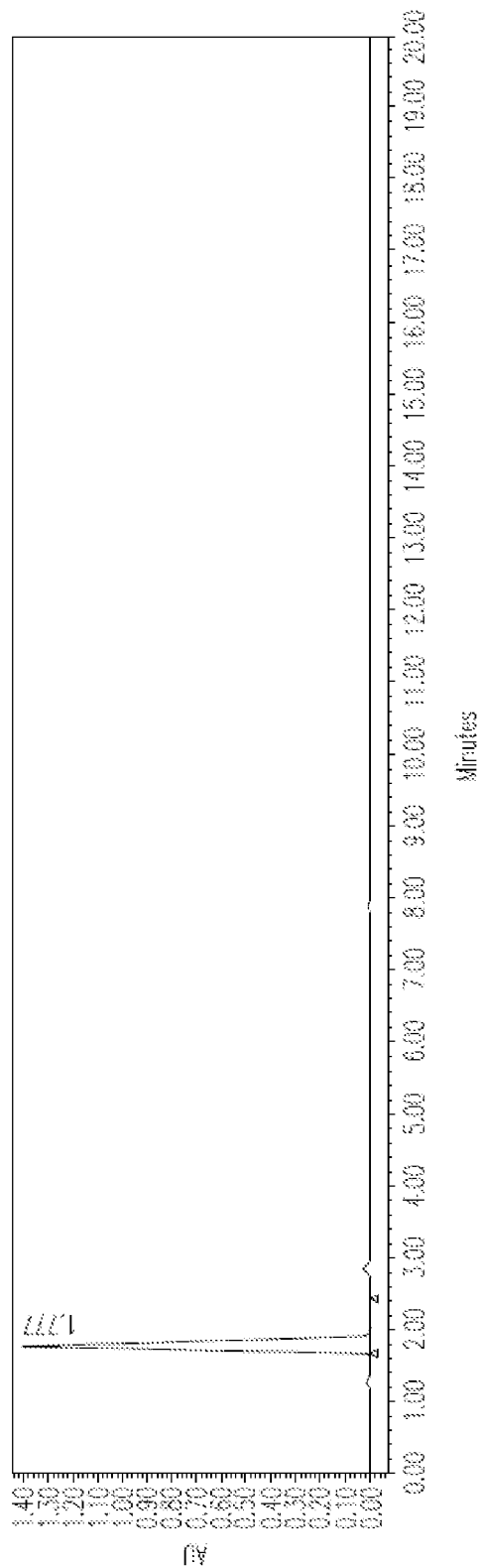
FIG. 4 is an HPLC chromatograph of the reaction admixture to form compound 5taz from compound 3taz, after 15 minutes of reaction time. A major peak at 1.777 min is shown.

The overall yield for the process was 78% (46.4 g active, 85.9 g total), isolated as a light tan to yellow solid. The overall purity was 90.0% AUC ("area under the curve" measurement), with a weight assay of 52.0%. The identity of the product can be confirmed by comparison to a reference NMR spectrum of ceftolozane TFA such as that shown in FIG. 4.

All molar equivalents and volumes (mL/g) are relative to the amount of active of TATD-CLE.

All reactions were performed under nitrogen atmosphere. The molar yield of Ceftolozane TFA is 78%. The molecular weight of Ceftolozane TFA is calculated without a counter ion.

Storage of Product and Stability: The material was stored at −20° C. in a clear glass container. No degradation was observed under these conditions, as determined by HPLC analysis.

Cleaning Procedure: Reactors were typically cleaned with water, then acetone, followed by acetone boil out and drying. The reactor then appeared to be clean by visual inspection.

7.5.4. Analytical Methods and Chromatograms

TABLE 3

In-Situ Monitoring

| Process Step | Analytical Test | Analytical Method | Preferred Composition |
|---|---|---|---|
| 7 | Reaction progress TATD-CLE and TATD-TFA to TATD-QUATE (3-5 h) | HPLC | ≤2.0% |
| 27 | Consumption of t-Butyl Ceftolozane TFA (4-8 h) | HPLC | ≤2.0% |
| 38 | Monitor residual volatiles during Ceftolozane TFA drying | HPLC | LOD value ≤ 19% |

TABLE 4

Analytical Testing for Process Characterization

| Process Step | Analytical Test | Analytical Method |
|---|---|---|
| 1 | Water content of THF in reactor | Karl Fischer titration |
| 2 | Water content of potassium trifluoroacetate | Karl Fischer titration |
| 14 | Residual TATD-QUATE in first aqueous layer | HPLC |
| 17 | Residual TATD-QUATE in second aqueous layer | HPLC |
| 20 | Solution yield of TATD-QUATE in final EtOAc layer | HPLC |
| 20 | % Peak area analysis of TATD-QUATE final EtOAc layer | HPLC |
| 20 | Water content of final ethyl acetate solution | Karl Fischer titration |
| 22 | GC Analysis for residual ethyl acetate in final anisole solution of TATD-QUATE | GC |
| 31 | Ceftolozane concentration in toluene layer | HPLC |
| 34 | Ceftolozane concentration in MTBE layer before filtration | HPLC |
| 38 | Residual palladium in ceftolozane TFA isolated intermediate | |
| 38 | Residual dibenzylideneacetone (dba) in ceftolozane TFA isolated intermediate | |
| 38 | Residual TDAPP in ceftolozane TFA isolated intermediate | |
| 38 | Residual DAP in ceftolozane TFA isolated intermediate | |
| 38 | Total phosphorus content in ceftolozane TFA isolated intermediate | |
| 38 | Residual BHT in ceftolozane TFA isolated intermediate | |

The sampling plan of Table 4 was used for process characterization. These analytical tests were not required during process validation and subsequent commercial production, but was used for investigation and/or additional process characterization.

7.6. Example 6: Preparation of Ceftazidime

The below experimental protocols (compound 1taz→compound 3taz, and compound 3taz→compound 5taz) demonstrate an approach to the antibiotic ceftazidime using the palladium catalysis technology described above. The key transformation is compound 3taz→compound 5taz, where compound 5taz was ceftazidime containing conventional protecting groups. A standard chemical deprotection of compound 5taz would provide ceftazidime.

7.6.1. Preparation of Compound 3Taz

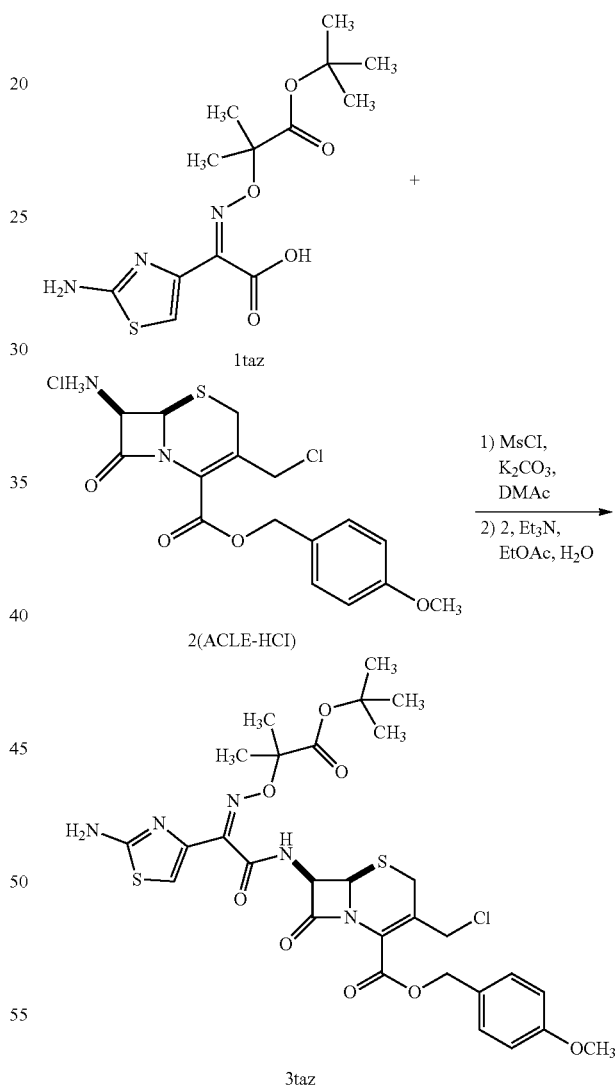

A solution of 1taz (3.98 g, 12.08 mmol) in dimethylacetamide (26.7 mL) was treated with methanesulfonyl chloride (1.87 mL, 24.16 mmol) at 0° C. Potassium carbonate (1.67 g, 12.08 mmol) was added and the reaction mixture was stirred at 0° C. After 2 h, EtOAc was charged to the reaction mixture followed by an aqueous solution of 2.4% HCl. The aqueous layer was removed and discarded and the remaining organic layer was washed with a 10% (w/v)

solution of NaCl. The aqueous layer was removed and discarded, and the organic layer was slowly added to a solution of 2 (ACLE.HCl, 4.45 g, 10.98 mmol) in H$_2$O (13.4 mL) and EtOAc (13.4 mL) at 0° C. The pH was maintained between 3.2-3.8 using a solution of triethylamine (3.83 mL) in EtOAc (5.78 mL). Once the addition was finished, the reaction mixture was stirred at 0° C. for 30 mins until the reaction was complete, as indicated by HPLC analysis. Solid NaCl (0.445 g) was added to the reaction, which was stirred for 20 minutes. The reaction mixture was then filtered, and the organic layer was separated and washed with 20% (w/v) NaCl. The organic layer was dried (NaSO$_4$), concentrated and the residue purified by chromatography on SiO$_2$ (7:1 EtOAc/Hexane) to provide taz as a white solid. $^1$H NMR (CDCl$_3$, 400 MHz) 7.95 (s, 1H), 7.35 (d, 2H, J=8.8 Hz), 6.94 (s, 1H), 6.90 (d, 2H, J=8.8 Hz), 6.32 (s, 2H), 5.99 (d, 1H, J=5.2 Hz), 5.27 (d, 1H J=11.6 Hz), 5.20 (d, 1H, J=11.6 Hz), 5.05 (d, 1H, J=4.8 Hz), 4.55 (d, 1H, J=12.0 Hz), 4.45 (d, 1H, J=12.0 Hz), 3.81 (s, 3H), 3.65 (d, 1H, J=18.0 Hz), 3.48 (d, 1H, J=18.0 Hz), 1.63 (s, 3H), 1.60 (s, 3H), 1.42 (s, 9H); HRMS ESI m/z calcd for C$_{29}$H$_{35}$ClN$_5$O$_8$S$_2$ 680.1537 [M+H]$^+$, found 680.1577.

An HPLC chromatograph of compound 3taz is shown in FIG. 5.

7.6.2. Preparation of Compound 5taz

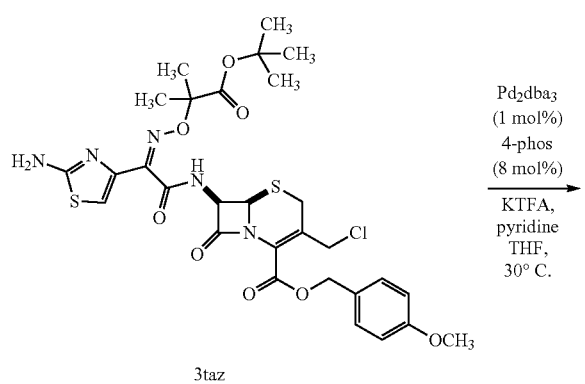

3taz

Pd$_2$dba$_3$ (1 mol%)
4-phos (8 mol%)
KTFA, pyridine
THF, 30° C.

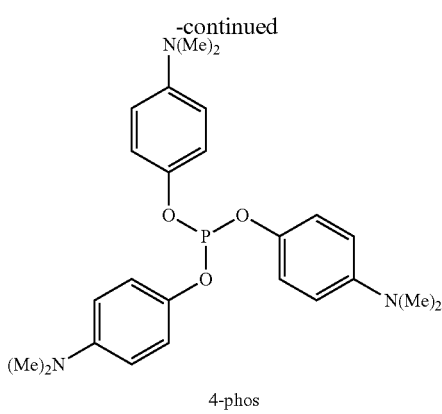

4-phos

To a solution of 3taz (0.250 g, 0.371 mmol) in THF (2.15 mL) was added KTFA (potassium trifluoroacetate, 0.085 g, 0.556 mmol), pyridine (0.033 mL, 0.408 mmol), 4-phos (0.013 g, 0.030 mmol) and Pd$_2$dba$_3$ (0.003 g, 0.004 mmol) at 30° C. After 15 min, HPLC analysis indicated 99% conversion (FIG. 5 and FIG. 6). The reaction mixture was filtered to afford a yellow solution of 5taz. $^1$H NMR (CD$_3$OD, 400 MHz) δ 9.01 (d, 2H, J=6.0 Hz), 8.61 (t, 1H, J=7.8 Hz), 8.10 (dd, 2H, J=6.8, 7.6 Hz), 7.34 (d, 2H, J=8.8 Hz), 6.89 (d, 2H, J=8.8 Hz), 6.85 (s, 1H), 5.98 (d, 1H, J=4.8 Hz), 5.74 (d, 1H, J 14.8 Hz), 5.40 (d, 1H, J=14.8 Hz), 5.26 (dd, 2H, J=12, 21.2 Hz), 5.25 (d, 1H, J=5.2 Hz), 3.79 (a, 3H), 3.70 (d, 1H, J=18.4 Hz), 3.40 (d, 1H, J=18.4 Hz), 1.54 (s, 3H), 1.53 (s, 3H), 1.45 (s, 9H); $^{13}$C NMR (CD$_3$OD. 101 MHz) δ 175.20, 171.41, 165.60, 165.21, 162.93, 161.61, 149.69, 147.64, 146.00, 142.92, 131.90, 131.11, 129.65, 127.89, 121.76, 114.98, 111.65, 84.24, 83.20, 69.84, 62.21, 60.74, 59.29, 55.76, 28.22, 27.40, 24.59, 24.49: HRMS ESI m/z calcd for C$_{34}$H$_{39}$N$_6$O$_8$S$_2$ 723.2265 [M]$^+$, found 723.2233.

An HPLC chromatograph of the reaction forming compound 5taz from compound 3taz is shown in FIG. 6.

7.7. Example 7: Aqueous Workup to Remove Palladium

Upon completion of the palladium-mediated coupling reactions described above, the aqueous workup was used to reduce the level of Pd remaining in the product stream. Examples of this include:

1. Dilute the reaction mixture with 7 volumes of ethyl acetate. Wash the resulting slurry for 30 minutes with 7 volumes of a 5% aqueous solution of EDTA. The Pd content of the organic layer is reduced from 461 ppm to 370 ppm.

2. Dilute the reaction mixture with 7 volumes of ethyl acetate. Wash the resulting slurry for 30 minutes with 7 volumes of a 5% aqueous solution of citric acid. The Pd content of the organic layer is reduced from 461 ppm to 208 ppm.

3. Dilute the reaction mixture with 7 volumes of ethyl acetate. Wash the resulting slurry for 30 minutes with 7 volumes of a 1 N aqueous solution of trifluoroacetic acid. The Pd content of the organic layer is reduced from 700 ppm to 237 ppm.

4. Dilute the reaction mixture with 7 volumes of ethyl acetate. Wash the resulting slurry for 30 minutes with 7 volumes of a 5% aqueous solution of sodium chloride. Treat the organic layer with 13 weight % Darco G-60 activated charcoal for 30 minutes. The Pd content of the organic layer is reduced from 461 ppm to 269 ppm.

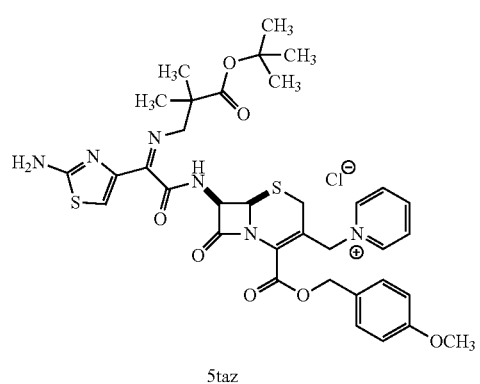

5taz

5. Ceftolozane TFA (100.0 g free base equivalent, 1 equiv) with about 100 ppm palladium level is charged in one portion to 2 liters of water and the batch is stirred for 30 minutes, resulting in a brown solution with a pH of about 1.6. Subsequently, a 5% ammonium hydroxide solution (165-170 mL) is added to the batch until the pH of the solution is 6.0 to 7.0, with a target pH of about 6.5. After reaching the target pH, a 5% aqueous solution of sodium diethyldithiocarbamate is charged. The solution is prepared by dissolving sodium diethyldithiocarbamate trihydrate (0.5 g, 0.5% weight/weight compared with ceftolozane free base) in water (95.0 g, 9.5 mL). The batch is then stirred for 30 to 60 minutes (target time of 45 minutes) and filtered through a 0.4 micron filter to remove palladium-containing solids. Following, the batch is treated with 15% hydrochloric acid (105 mL) until the pH of the solution is 1.2 to 2.0 (target pH of 1.5). The batch is then stirred for 20 to 40 min (target of 30 min) and filtered using a 0.2 micron filter to remove palladium-containing solids. The resulting solution comprising ceftolozane and a residual palladium level of 0.001-10 ppm is then converted as previously described to ceftolozane sulfate having the same residual level of palladium.

8. EQUIVALENTS AND INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A process for preparing a compound of the formula (IIa):

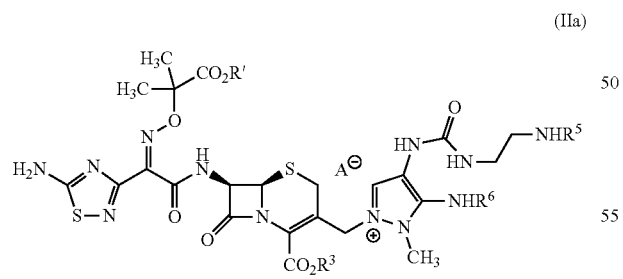

(IIa)

wherein $A^\ominus$ is a pharmaceutically acceptable anion, selected from the group consisting of chloride, bromide, iodide, sulfate, bisulfate, toluenesulfonate, methanesulfonate, edisylate, maleate, monophosphate, biphosphate, ketoglutarate, trifluoroacetate, and trifluoromethanesulfonate;

comprising the step of admixing a compound of the formula (IIIa), or a salt thereof,

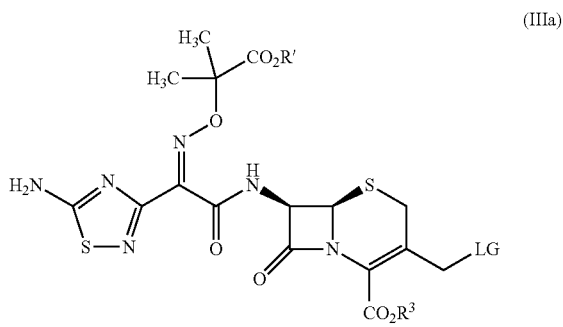

(IIIa)

with a compound of the formula (X):

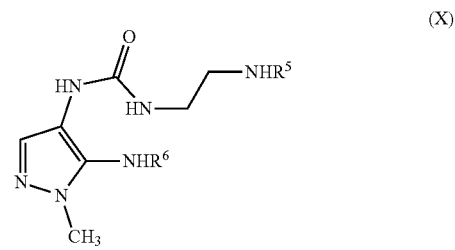

(X)

wherein:
R' is tert-butyldimethylsilyl, tert-butyl, 4-methoxybenzyl, 2-methoxybenzyl, or triphenylmethyl;
$R^3$ is tert-butyldimethylsilyl, tert-butyl, 4-methoxybenzyl, 2-methoxybenzyl, or triphenylmethyl;
$R^5$ is triphenylmethyl, tert-butyl, tert-butoxycarbonyl, 2-trimethylsilylethoxycarbonyl, or 4-methoxybenzyloxycarbonyl;
$R^6$ is triphenylmethyl, tert-butyl, tert-butoxycarbonyl, 2-trimethylsilylethoxycarbonyl, or 4-methoxybenzyloxycarbonyl; and
LG is halo or —OC(O)$R^{18}$, wherein $R^{18}$ is selected from the group consisting of $C_{1-6}$ alkyl and $C_{1-6}$ haloalkyl;
in the presence of reagents comprising:
(a) a palladium source, wherein the palladium source is selected from the group consisting of: bis(acetonitrile)dichloropalladium(II), bis(acetylacetonate)palladium(II), bis(benzonitrile)palladium(II) chloride, bis(dibenzylideneacetone)palladium, allylpalladium (II) chloride dimer, palladium(II) acetate, palladium (II) trifluoroacetate, palladium(II) chloride, palladium(II) bromide, tetrakis(acetonitrile)-palladium(II)tetrafluoroborate, tris(dibenzylideneacetone)dipalladium(0), tris(dibenzylideneacetone)dipalladium(0)-chloroform adduct, [1,2-bis(diphenylphosphinoethane] dichloropalladium(II), 1,1'-bis(diphenyl- phosphino)ferrocene-palladium(II)dichloride dichloromethane adduct, bis(tricyclohexylphosphine)palladium(0), bis(triethylphosphine)palladium(II) chloride, bis(triphenylphosphine)palladium(II) acetate, bis(triphenylphosphine)palladium(II) chloride, bis (tri-t-butylphosphine)palladium(0), bis[1,2-bis(diphenylphosphino)ethane]palladium(0), bis[tri(o-tolyl)phosphine]palladium(II) chloride, dichlorobis (tricyclohexylphosphine)palladium(II), tetrakis (triphenylphosphine)palladium(0), and trans-benzyl (chloro)bis(triphenylphosphine)palladium(II); and (b) a palladium-binding ligand selected from the group consisting of:
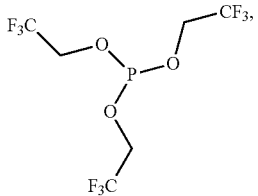
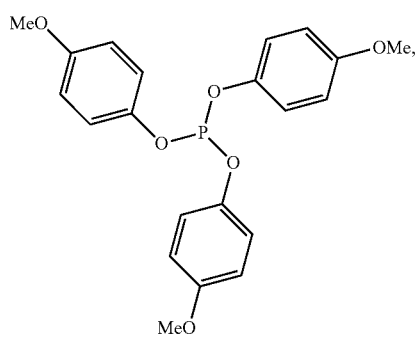
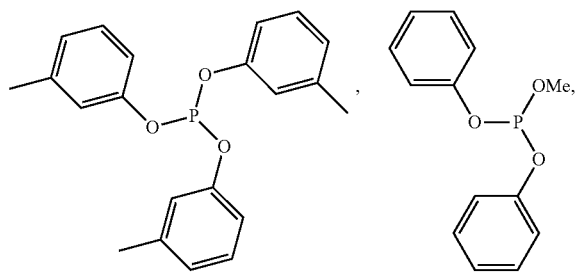
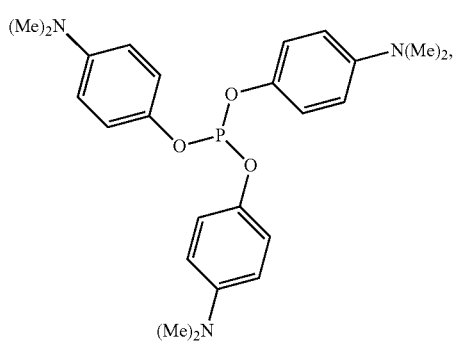
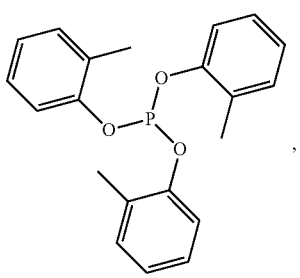
-continued
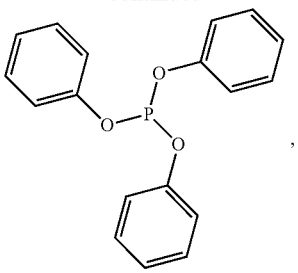
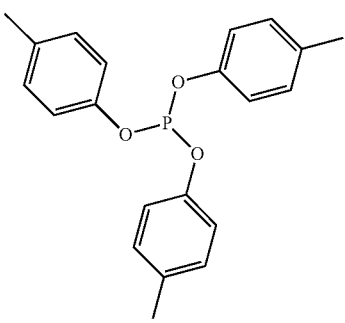
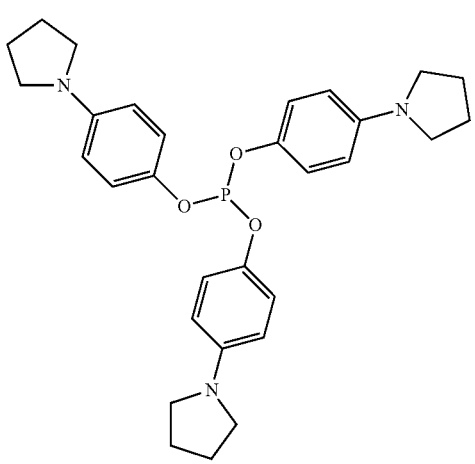
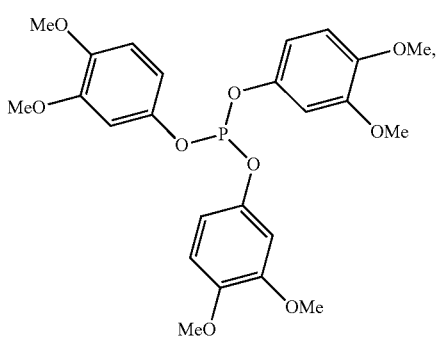
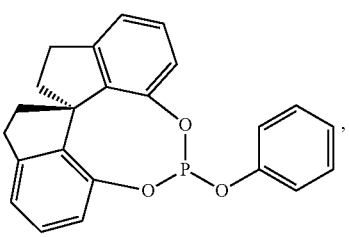

-continued

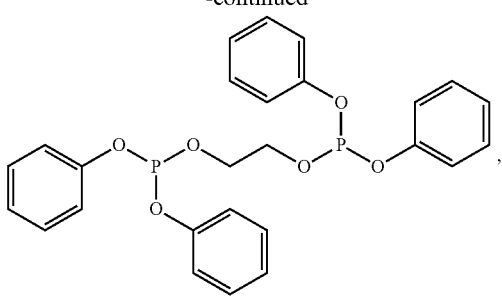

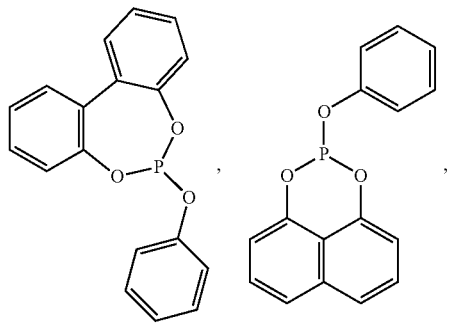

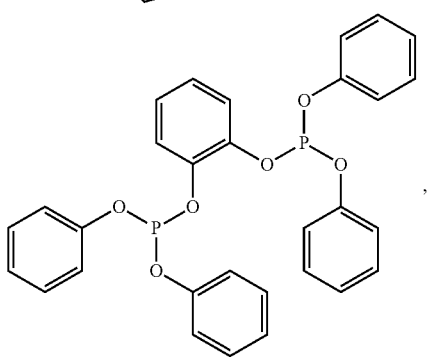

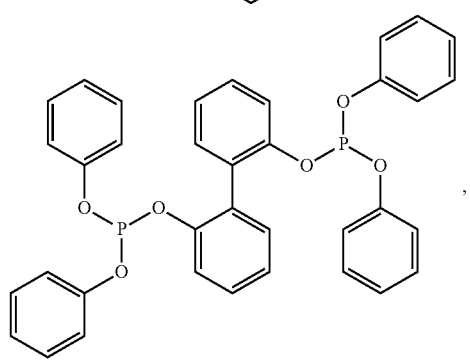

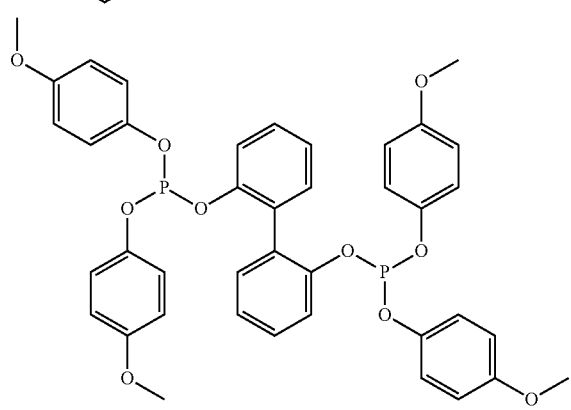

-continued

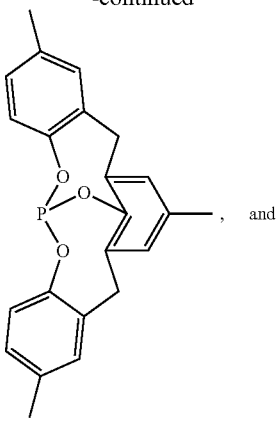, and

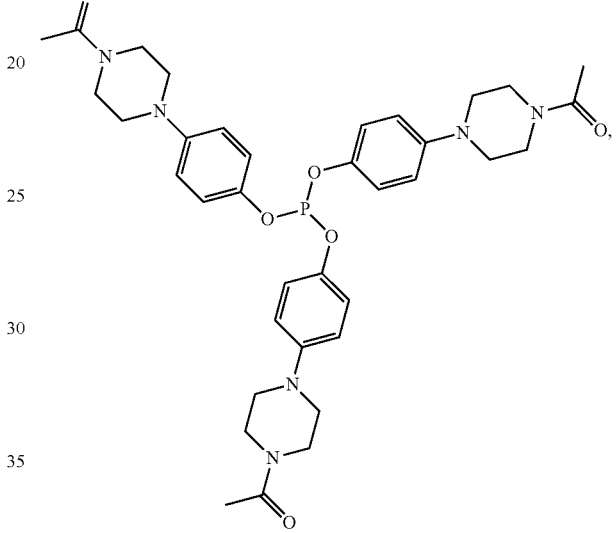

to provide the compound of formula (IIa), or a salt thereof.

2. The process of claim 1, wherein:
R' is tert-butyl; and
$R^3$ is 4-methoxybenzyl.

3. The process of claim 1, wherein:
$R^5$ is tert-butyloxycarbonyl; and
$R^6$ is triphenylmethyl.

4. The process of claim 1, wherein LG is chloro or —OC(O)CF$_3$.

5. The process of claim 1, wherein $A^\ominus$ is selected from chloride, acetate, trifluoroacetate and bisulfate.

6. The process of claim 1, wherein $A^\ominus$ is trifluoroacetate or bisulfate.

7. The process of claim 1, wherein $A^\ominus$ is trifluoroacetate.

8. The process of claim 1, wherein the palladium source is selected from the group consisting of: tris(dibenzylideneacetone) dipalladium(0), tris(dibenzylideneacetone)dipalladium(0)-chloroform adduct, tetrakis(triphenylphosphine) palladium, palladium(II) acetate, palladium(II) trifluoroacetate, palladium(II) chloride, palladium(II) bromide, and bis(acetonitrile)dichloropalladium(II).

9. The process of claim 1, wherein the palladium source is tris(dibenzylideneacetone)dipalladium(0).

10. The process of claim 1, wherein the palladium-binding ligand is selected from the group consisting of:

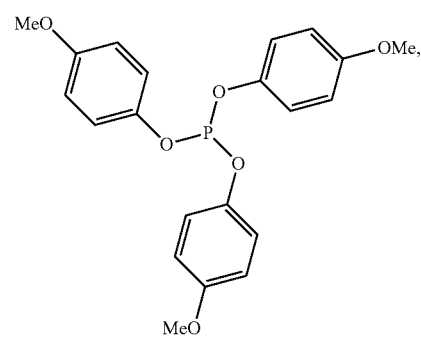
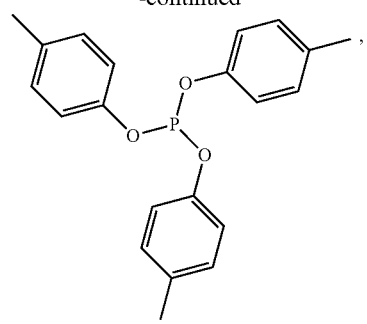
-continued
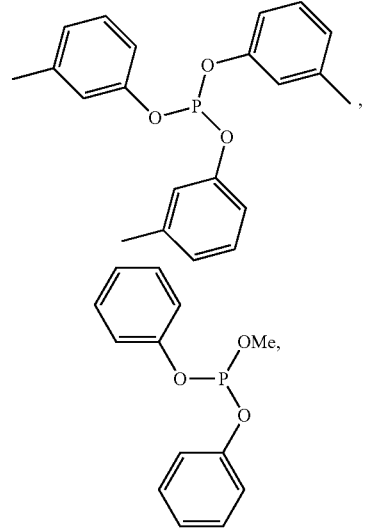
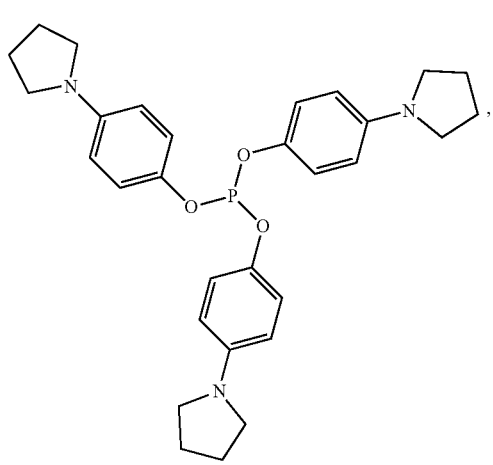
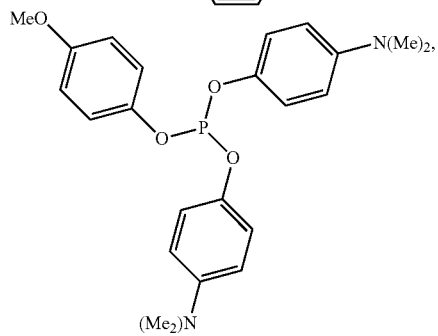
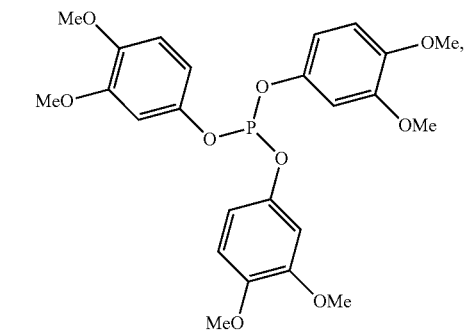
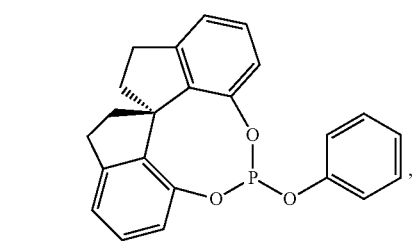

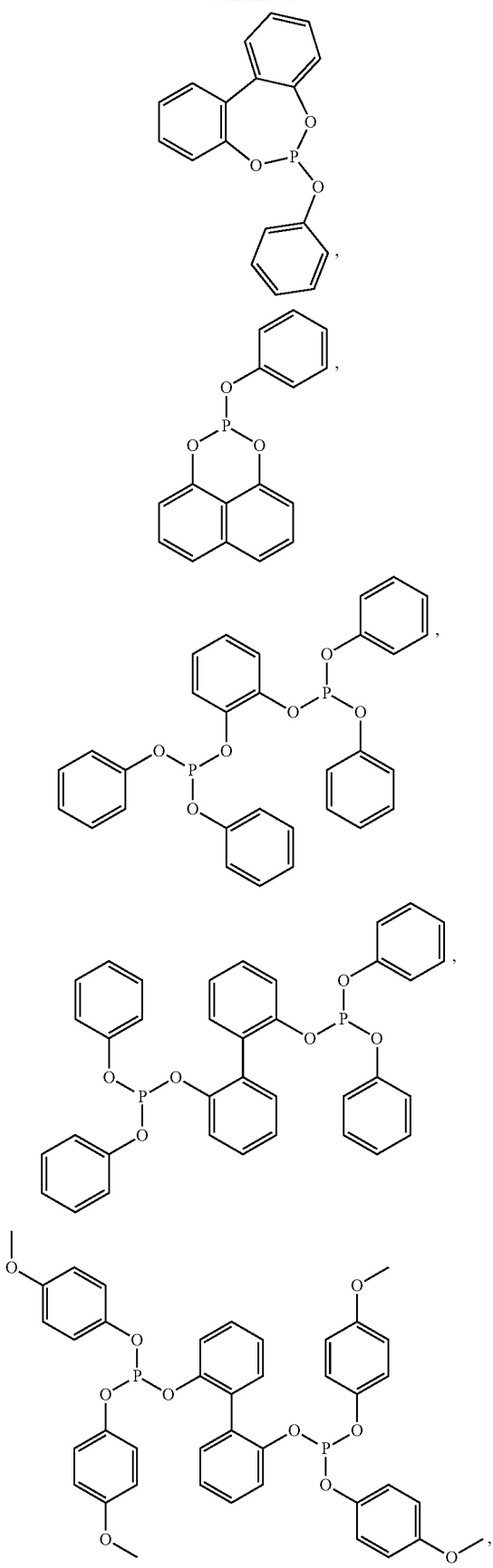

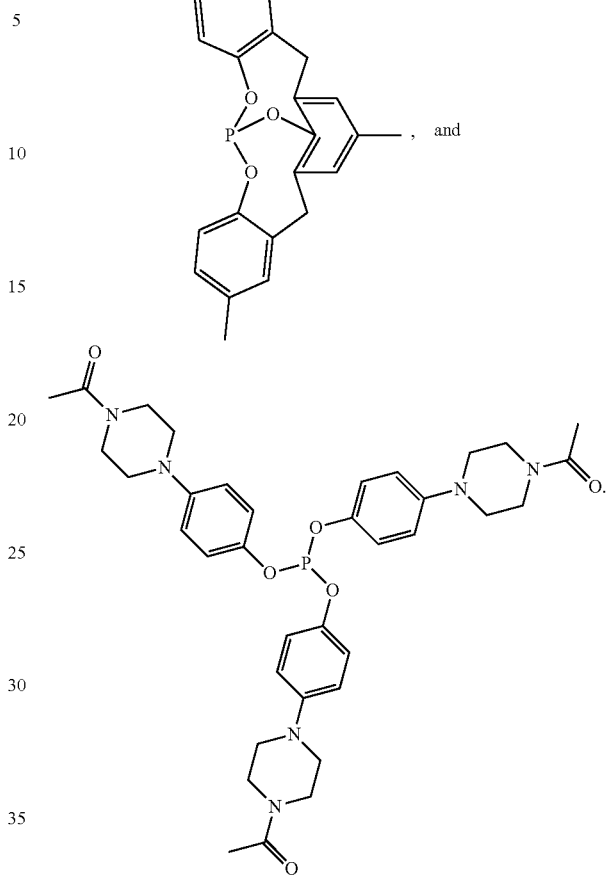

11. The process of claim 1, wherein the palladium-binding ligand is:

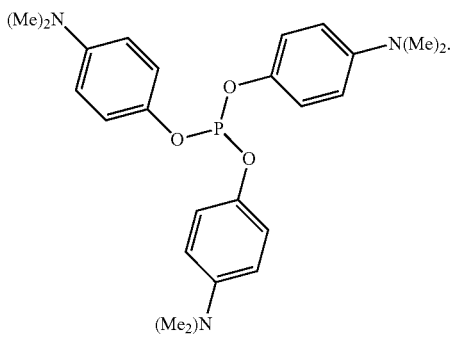

12. The process of claim 1, wherein the step of admixing a compound of formula (IIa) in the presence of reagents comprising (a) a palladium source and (b) a palladium-binding ligand forms a pi-allyl intermediate.

13. The process of claim 1, wherein the palladium-binding ligand is present in a molar ratio of between about 1:1 to about 10:1 with respect to the molar amount of palladium in the palladium source.

14. The process of claim 1, wherein the palladium-binding ligand is present in a molar ratio of between about 3:1 and about 10:1 with respect to the molar amount of palladium in the palladium source.

15. The process of claim 1, wherein the palladium-binding ligand is present in a molar ratio of between about 4:1 and about 10:1 with respect to the molar amount of palladium in the palladium source.

16. The process of claim 1, wherein the palladium-binding ligand is present in a molar ratio of between about 5:1 and about 10:1 with respect to the molar amount of palladium in the palladium source.

17. The process of claim 1, wherein the palladium-binding ligand is present in a molar ratio of between about 6:1 and about 10:1 with respect to the molar amount of palladium in the palladium source.

18. The process of claim 1, wherein the palladium source is present in an amount of from about 0.2 mole % to about 5 mole % with respect to the compound of formula (IIIa).

19. The process of claim 1, wherein the palladium source is present in an amount of from about 0.5 mole % to about 5 mole % with respect to the compound of formula (IIIa).

20. The process of claim 1, further comprising the step of removing the palladium by washing with an aqueous acidic solution after forming the compound of formula (II).

21. The process of claim 20, further comprising the step of recovering the palladium, after the step of removing the palladium, by increasing the pH of the aqueous acidic solution and adding an oxidant to the aqueous acidic solution, thereby recovering the palladium.

22. The process of claim 1, wherein the reagents further comprise (c) a salt additive which is selected from the group consisting of potassium trifluoroacetate, sodium trifluoroacetate, lithium trifluoroacetate, potassium triflate, sodium triflate, lithium triflate, silver triflate and copper sulfate.

23. The process of claim 1, wherein the reagents further comprise (c) a salt additive which is potassium trifluoroacetate.

24. The process of claim 1, further comprising the step of admixing the compound of formula (IIa):

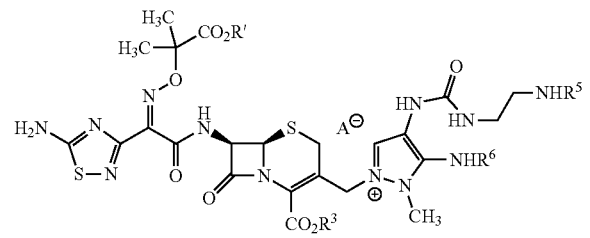

(IIa)

wherein $A^\ominus$ is a pharmaceutically acceptable anion, selected from the group consisting of chloride, bromide, iodide, sulfate, bisulfate, toluenesulfonate, methanesulfonate, edisylate, maleate, monophosphate, biphosphate, ketoglutarate, trifluoroacetate, and trifluoromethanesulfonate;

with a strong acid selected from trifluoroacetic acid and hydrochloric acid, to form an admixture comprising a compound of formula (Va):

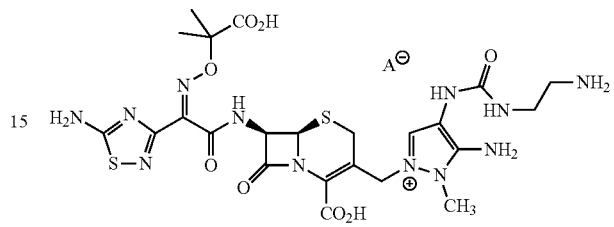

(Va)

wherein $A^\ominus$ is trifluoroacetate or chloride.

25. The process of claim 24, further comprising the step of isolating the compound of formula (Va) wherein $A^\ominus$ is trifluoroacetate or chloride comprising the steps of:
  (a) extracting the admixture with a non-polar solvent; and
  (b) adding from about 2 to about 6 volumes of acetonitrile to isolate the compound of formula (Va).

26. The process of claim 24, wherein the strong acid is trifluoroacetic acid, and wherein the compound of formula (Va):

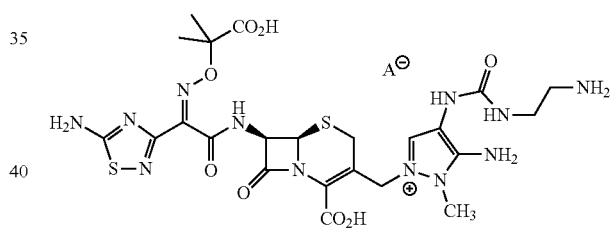

(Va)

$A^\ominus$ is trifluoroacetate.

27. The process of claim 26, further comprising the step of isolating the compound of formula (Va) wherein $A^\ominus$ is trifluoroacetate comprising the steps of:
  (a) extracting the admixture with a non-polar solvent; and
  (b) adding from about 2 to about 6 volumes of acetonitrile to isolate the compound of formula (Va).

28. The process of claim 27, further comprising the step of filtering the solids to isolate the compound of formula (Va) wherein $A^\ominus$ is trifluoroacetate.

* * * * *